United States Patent
Hutchens et al.

(10) Patent No.: US 7,491,549 B2
(45) Date of Patent: *Feb. 17, 2009

(54) APPARATUS FOR DESORPTION AND IONIZATION OF ANALYTES

(75) Inventors: T. William Hutchens, Mountain View, CA (US); Tai-Tung Yip, Cupertino, CA (US)

(73) Assignee: Baylor College of Medicine, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 11/503,565

(22) Filed: Aug. 10, 2006

(65) Prior Publication Data

US 2007/0065949 A1 Mar. 22, 2007

Related U.S. Application Data

(60) Continuation of application No. 10/887,552, filed on Jul. 7, 2004, now abandoned, which is a continuation of application No. 10/700,297, filed on Oct. 31, 2003, now Pat. No. 7,294,515, which is a continuation of application No. 09/848,512, filed on May 3, 2001, now abandoned, which is a continuation of application No. 09/215,380, filed on Dec. 18, 1998, now abandoned, which is a division of application No. 08/556,951, filed as application No. PCT/US94/06064 on May 27, 1994, now Pat. No. 6,020,208, which is a continuation-in-part of application No. 08/068,896, filed on May 28, 1993, now abandoned.

(51) Int. Cl.
*G01N 33/537* (2006.01)

(52) U.S. Cl. .................. 436/178; 436/174; 436/173; 436/63; 436/155; 250/287

(58) Field of Classification Search ............... 436/178, 436/63, 155, 173, 174; 250/287
See application file for complete search history.

(56) References Cited

U.S. PATENT DOCUMENTS

| | | | |
|---|---|---|---|
| 3,896,661 A | 7/1975 | Parkhurst et al. | |
| 4,022,876 A | 5/1977 | Anbar | |
| 4,295,046 A | 10/1981 | Gruter et al. | |
| 4,296,332 A | 10/1981 | Hill | |
| 4,454,233 A | 6/1984 | Wang | |
| 4,468,468 A | 8/1984 | Benninghoven et al. | |
| 4,665,192 A | 5/1987 | Cerami | |
| 4,686,366 A | 8/1987 | Stuke | |
| 4,694,167 A | 9/1987 | Payne et al. | |
| 4,705,616 A | 11/1987 | Andresen et al. | |
| 4,902,627 A | 2/1990 | Kidwell | |
| 4,988,879 A | 1/1991 | Zare et al. | |
| 5,003,059 A | 3/1991 | Brennan | |
| 5,045,694 A | 9/1991 | Beavis et al. | |
| 5,073,713 A | 12/1991 | Smith et al. | |
| 5,078,135 A | 1/1992 | Caprioli et al. | |
| 5,118,937 A | 6/1992 | Hillenkamp et al. | |
| 5,124,267 A | 6/1992 | Humpel et al. | |
| 5,171,989 A | 12/1992 | Williams et al. | |
| 5,209,919 A | 5/1993 | Turteltaub et al. | |
| 5,260,571 A | 11/1993 | Cottrell et al. | |
| 5,317,932 A | 6/1994 | Westlake, III et al. | |
| 5,547,835 A | 8/1996 | Koster | |
| 5,622,824 A | 4/1997 | Koster | |
| 5,719,060 A | 2/1998 | Hutchens et al. | |
| 5,894,063 A | 4/1999 | Hutchens et al. | |
| 6,020,208 A | 2/2000 | Hutchens et al. | |
| 6,027,942 A | 2/2000 | Hutchens et al. | |
| 6,060,237 A | 5/2000 | Nygren et al. | |
| 6,124,137 A | 9/2000 | Hutchens et al. | |
| 6,225,047 B1 | 5/2001 | Hutchens et al. | |
| 6,579,719 B1 | 6/2003 | Hutchens et al. | |
| 7,074,619 B2 * | 7/2006 | Hutchens et al. | ............... 436/63 |
| 7,413,909 B2 * | 8/2008 | Hutchens et al. | ............. 436/178 |

FOREIGN PATENT DOCUMENTS

| | | |
|---|---|---|
| DE | 3221681 A1 | 12/1983 |
| EP | 0 084 086 | 7/1983 |
| EP | 0 333 912 | 9/1989 |
| GB | 2235528 | 3/1991 |
| GB | 2235529 | 3/1991 |

(Continued)

OTHER PUBLICATIONS

American Biotechnology Laboratory, Feb. 1994 cover, cover-page 2 (1994).

(Continued)

*Primary Examiner*—Lyle A Alexander
(74) *Attorney, Agent, or Firm*—Townsend and Townsend and Crew LLP

(57) ABSTRACT

This invention relates generally to methods and apparatus for desorption and ionization of analytes for the purpose of subsequent scientific analysis by such methods, for example, as mass spectrometry or biosensors. More specifically, this invention relates to the field of mass spectrometry, especially to the type of matrix-assisted laser desorption/ionization, time-of-flight mass spectrometry used to analyze macromolecules, such as proteins or biomolecules. Most specifically, this invention relates to the sample probe geometry, sample probe composition, and sample probe surface chemistries that enable the selective capture and desorption of analytes, including intact macromolecules, directly from the probe surface into the gas (vapor) phase without added chemical matrix.

10 Claims, 42 Drawing Sheets

FOREIGN PATENT DOCUMENTS

| | | |
|---|---|---|
| GB | 2236184 | 3/1991 |
| GB | 2236185 B | 3/1994 |
| WO | WO 91/02961 | 3/1991 |
| WO | WO 92/13629 | 8/1992 |
| WO | WO 96/37777 | 11/1996 |
| WO | WO 96/40888 | 12/1996 |
| WO | WO 99/06833 A1 | 2/1999 |

OTHER PUBLICATIONS

Beavis, R. et al., "Epitaxial protein inclusion in sinapic acid crystals" J. Phys. D: Appl. Phys. 26:442-447 (1993).

Brockman, A. et al., "Probe-immobilized affinity chromatography/mass spectrometry" Anal. Chem. 67(24):4581-5 (1995) [Abstract].

Brodbelt et al., "In vivo mass spectrometric determination of organic compounds in blood with a membrane probe" Anal. Chem. 59:454-458 (1987).

Dwyer, J. et al., "A novel sample preparation device for MALDI-MS" Intn'l Lab. 13A-13F (1997).

Fitzgerald, M. et al., "Direct characterization of solid phase resin-bound molecules by mass spectrometry" Bioorg. Med. Chem. Lett. 6(8):979-982 (1996) [Abstract].

Hillenkamp, F., "Laser desorption mass spectrometry: Mechanisms techniques and applications" Bordeaux Mass Spect. Conference Report 11A:354-362 (1988).

Hutchens, T. et al., "Differences in the confrontational state of a zinc-finger DNA-binding protein domain occupied by zinc and copper revealed by electrospray ionization mass spectrometry" Rapid Comm. in Mass Spect. 6:469-473 (1992).

Hutchens, T. et al., "New desorption strategies for the mass spectrometric analysis of macromolecules" Rapid Comm. in Mass Spect. 7:576-580 (1993).

Jonsson, G., et al., "Plasma desorption mass spectrometry of peptides and proteins adsorbed on nitrocellulose" Anal. Chem. 58(6):1084-1087 (1986).

Karas, M. et al., "Laser desorption ionization of proteins with molecular masses exceeding 10,000 daltons" Anal. Chem. 60:2299-2301 (1988).

Karas, M. et al., "Ultraviolet laser desorption of proteins up to 120,000 daltons" Bordeaux Mass Spect. Conference Report 11A:416-417 (1988).

Karas, M. et al., "UV laser desorption/ionization mass spectrometry of femtomol amounts of large proteins" Biomed. Environ. Mass Spectr. 18:841-843 (1989).

Mock, K. et al., "Sample Immobilization protocols for matrix-assisted laser desorption mass spectrometry" Rapid Comm. in Mass Spec. 6:233-238 (1994).

Nelson et al., "Mass spec. analysis of a trans-metal-binding peptide using MALDTOFMS: A demonstration of probe tip chemistry" Rapid Comm. Mass Spec. 6:4-8 (1992).

Nelson et al., "Mass spectrometric immunoassay" Anal. Chem. 67:1153-58 (1995).

Rivera, A., "A summary statement: Probes for affinity mass spectrometry of phophoproteins" Apr. 16, 1994.

Siuzdak, G. et al., "Applications of mass spectrometry in combinatorial chemistry" Biotech. Bioeng. 61(2):127-134 (1998) [Abstract].

Speir, J. et al., "Substrater-assisted laser desorption of neutral peptide molecules" Anal. Chem. 64:1041-1045 (1992).

Strupat, K. et al., "2,5-Dihydroxybenzoic acid: A new matrix for laser desorption-ionization mass spectrometry" Int'l J. Mass Spectr. and Ion Proc. 111:89-102 (1991).

Van Breemen et al., "Time-resolved laser desorption mass spectrometry. I. Desorption of performed ions" Interntnl. J. Mass Spectro. Ion Phys. 49: 36-51 (1983).

Xiang, F. et al., "A method to increase contaminant tolerance in protein matrix-assisted laser desorption/ionization by the fabrication of thin protein-doped polycrystalline films" Rapid Comm. in Mass Spec. 8:199-204 (1994).

Yip, T. et al., Protein Expression and Purification 2:355-362 (1991).

* cited by examiner

SEND

SEND

SEND

SEND

SEND

SEND

APPARATUS FOR DESORPTION AND IONIZATION OF ANALYTES

CROSS-REFERENCES TO RELATED APPLICATIONS

This application is a continuation of application Ser. No. 10/887,552, filed Jul. 7, 2004, now abandoned, which is a continuation of application Ser. No. 10/700,297, filed Oct. 31, 2003, now U.S. Pat. No. 7,294,515, which is a continuation of application Ser. No. 09/848,512, filed May 3, 2001, now abandoned, which is a continuation of application Ser. No. 09/215,380, filed Dec. 18, 1998, now abandoned, which is a division of application Ser. No. 08/556,951, filed Nov. 27, 1995, now U.S. Pat. No. 6,020,208, issued Feb. 1, 2000, which is a national phase of International Application No. PCT/US94/06064, filed May 27, 1994, which is a continuation-in-part of application Ser. No. 08/068,896, filed May 28, 1993, now abandoned, the disclosures of which are hereby incorporated by reference in their entirety for all purposes.

STATEMENT AS TO RIGHTS TO INVENTIONS MADE UNDER FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

This invention relates generally to methods and apparatus for desorption and ionization of analytes for the purpose of subsequent scientific analysis by such methods, for example, as mass spectrometry (MS) or biosensors. Generally, analysis by mass spectrometry involves the vaporization and ionization of a small sample of material, using a high energy source, such as a laser, including a laser beam. The material is vaporized from the surface of a probe tip into the gas or vapor phase by the laser beam, and, in the process, some of the individual molecules are ionized by the gain of a proton. The positively charged ionized molecules are then accelerated through a short high voltage field and let fly (drift) into a high vacuum chamber, at the far end of which they strike a sensitive detector surface. Since the time-of-flight is a function of the mass of the ionized molecule, the elapsed time between ionization and impact can be used to determine the molecule's mass which, in turn, can be used to identify the presence or absence of known molecules of specific mass.

All known prior art procedures which present proteins or other large biomolecules on a probe tip for laser desorption/ionization time-of-flight mass spectrometry (TOF) rely on the preparation of a crystalline solid mixture of the protein or other analyte molecule in a large molar excess of acidic matrix material deposited on the bare surface of a metallic probe tip. (The sample probe tip typically is metallic, either stainless steel, nickel plated material or platinum). Embedding the analyte in such a matrix was thought to be necessary in order to prevent the destruction of analyte molecules by the laser beam. The laser beam strikes the solid mixture on the probe tip and its energy is used to vaporize a small portion of the matrix material along with some of the embedded analyte molecules. Without the matrix, the analyte molecules are easily fragmented by the laser energy, so that the mass, and identity, of the original macromolecule is very difficult or impossible to determine.

This prior art procedure has several limitations which have prevented its adaptation to automated protein or other macrobiological molecular analysis. First, in a very crude sample it is necessary to partially fractionate (or otherwise purify the sample as much as possible) to eliminate the presence of excessive extraneous materials in the matrix/analyte crystalline or solid mixture. The presence of large quantities of components may depress the ion signal (either desorption, ionization and/or detection) of the targeted analyte. Such purification is time-consuming, expensive, typically results in low recovery (or complete loss) of the analyte, and would be very difficult to do in an automated analyzer.

Second, while the amount of analyte material needed for analysis by the prior art method is not large (typically in a picomole range), in some circumstances, such as tests on pediatric patients, analyte fluids are available only in extremely small volumes (microliters) and may be needed for performing several different analyses. Therefore, even the small amount (i.e., volume) needed for preparation of the analyte/matrix crystalline mixture for a single analysis may be significant. Also, only a tiny fraction (a few thousandths or less) of analyte used in preparing the solid analyte/matrix mixture for use on the probe tip is actually consumed in the desorption or mass spectrometric analysis. Any improvement in the prior art procedure which would make it possible to 1) use much less analyte, 2) to locate the analyte or multiple analytes on the probe tip or surface in a predetermined location, 3) to perform repeated analyses of the same aliquot of analyte (e.g., before and after one or more chemical and or enzymatic reactions), and 4) to conduct the test in a more quantitative manner, would be highly advantageous in many clinical areas.

Third, the analyte protein, or other macromolecule, used in preparing the solid solution of analyte/matrix for use on the probe tip is not suitable for any subsequent chemical tests or procedures because it is bound up (i.e., embedded) in the matrix material. Also, all of the matrix material used to Date is strongly acidic, so that it would adversely affect many chemical reactions which might be attempted on the mixture in order to modify the analyte molecules for subsequent examination. Any improvement in the procedure which made it possible to conduct subsequent chemical modifications or reactions on the analyte molecules, without removing them from the matrix or the probe tip or without "matrix" altogether, would be of enormous benefit to researchers and clinicians.

The first successful molecular mass measurements of intact peptides and small proteins (only up to about 15 kDa) by any form of mass spectrometry were made by bombarding surfaces with high energy particles (plasma desorption and fast atom bombardment mass spectrometry); this breakthrough came in 1981 and 1982. Improvements came in 1985 and 1986, however, yield (signal intensities), sensitivity, precision, and mass accuracy remained relatively low. Higher molecular mass proteins (about 20 to 25 kDa) were not observed except on rare occasions; proteins representing average molecular weights (approximately 70 kDa) were not ever observed with these methods. Thus, evaluation of most proteins by mass spectrometry remains unrealized.

In 1988, Hillenkamp and his coworkers used UV laser desorption time of-flight mass spectrometry and discovered that when proteins of relatively high molecular mass were deposited on the probe tip in the presence of a very large molar excess of an acidic, UV absorbing chemical matrix (nicotinic acid) they could be desorbed in the intact state. This new technique is called matrix-assisted laser desorption/ionization (MALDI) time-of-flight mass spectrometry. Note that laser desorption time-of-flight mass spectrometry (without the chemical matrix) had been around for some time, however, there was little or no success determining the molecular weights of large intact biopolymers such as proteins and nucleic acids because they were fragmented (destroyed) upon desorption. Thus, prior to the introduction of a chemical matrix, laser desorption mass spectrometry was essentially useless for the detection of specific changes in the mass of intact macromolecules. Note that the random formation of matrix crystals and the random inclusion of analyte molecules in the solid solution is prior art.

There are a number of problems and limitations with the prior art methods. For example, previously, it has been found that it is difficult to wash away contaminants present in analyte or matrix. Other problems include formation of analyte-salt ion adducts, less than optimum solubility of analyte in matrix, unknown location and concentration of analyte molecules within the solid matrix, signal (molecular ion) suppression "poisoning" due to simultaneous presence of multiple components, and selective analyte desorption/ionization. Prior investigators, including Karas and Hillenkamp have reported a variety of techniques for analyte detection using mass spectroscopy, but these techniques suffered because of inherent limitations in sensitivity and selectivity of the techniques, specifically including limitations in detection of analytes in low volume, undifferentiated samples. (Hillenkamp, Bordeaux Mass Spectrometry Conference Report, pp. 354-62 (1988); Karas and Hillenkamp, Bordeaux Mass Spectrometry Conference Report, pp. 416-17 (1988); Karas and Hillenkamp, Analytical Chemistry, 60:2299 (1988); Karas, et al., Biomed. Environ. Mass Spectrum (in press).) The use of laser beams in time-of-flight mass spectrometers is shown, for example, in U.S. Pat. Nos. 4,694,167; 4,686,366, 4,295,046, and 5,045,694, incorporated by reference.

The successful volatilization of high molecular weight biopolymers, without fragmentation, has enabled a wide variety of biological macromolecules to be analyzed by mass spectrometry. More importantly perhaps, it has illustrated the potential of using mass spectrometry more creatively to solve problems routinely encountered in biological research. Most recent attention has been focused on the utility of matrix-assisted laser desorption/ionization (MALDI) time-of-flight (TOF) mass spectrometry (MS), largely because it is rapid (min), sensitive (<pmol sample required), and permits complex mixtures to be analyzed.

Although MALDI-TOF MS continues to be useful for the static determination/verification of mass for individual analytes, in the case of biopolymers, it is often differences in mass that provide the most important information about unknown structures. Thus, for routine use in structural biology, an unfortunate limitation of the MALDI-TOF MS technique relates to sample preparation and presentation (deposition) on an inert probe element surface, specifically, the requirement that analytes be embedded (i.e., co-solidified) on the probe surface in a freshly prepared matrix of crystalline organic acid. The random distribution of analyte in a heterogeneous display of crystal matrix on the probe element surface requires the deposition of far more analyte or sample than is needed for the laser desorption process, even for the collection of more than adequate mass spectra (e.g., multiple sets of 100 shots each). The remaining portion of the analyte is usually not recovered for additional analyses or subsequent characterizations. Even though 1 to 10 pmol (sometimes less) of analyte are typically required for deposition on the probe surface, it has been estimated that less than a few attomoles are consumed during laser desorption. Thus, only 1 part in $10^5$ or $10^6$ of the applied analyte may be necessary; the rest is lost.

Another important loss of potential Data associated with the embedding of analyte in a solid matrix is the reduction or the complete elimination of ability to perform subsequent chemical and/or enzymatic modifications to the embedded analyte (e.g., protein or DNA) remaining on the probe surface.

Only another aliquot of analyte, or the ability to recover the embedded analyte free of matrix (difficult with low recovery), allows what we now refer to as differential mass spectrometry to be performed to derive structural Data.

In addition, there has been limited application of MS in biological fields, likely due to the fact that many biologists and clinicians are intimidated by MS and/or skeptical in regard to its usefulness. Further, MS is perceived as inaccessible or too costly, particularly because SDS polyacrylamide gel electrophoresis is an adequate substitute in some instances where MALDI would be applied (e.g., separation of crude biological fluids).

In addition, MALDI has had little exposure in biological and clinical journals.

BRIEF SUMMARY OF THE INVENTION

An object of the invention is to provide improved methods, materials composition and apparatus for coupled adsorption, desorption and ionization of multiple or selected analytes into the gas (vapor) phase.

Another object is to provide a method and apparatus for affinity-directed detection of analytes, including desorption and ionization of analytes in which the analyte is not dispersed in a matrix solution or crystalline structure but is presented within, on or above an attached surface of energy absorbing "matrix" material through molecular recognition events, in a position where it is accessible and amenable to a wide variety of chemical, physical and biological modification or recognition reactions.

Another object is to provide such a method and apparatus in which the analyte material is chemically bound or physically adhered to a substrate forming a probe tip sample presenting surface.

A further object is to provide means for the modification of sample presenting surfaces with energy-absorbing molecules to enable the successful desorption of analyte molecules without the addition of exogenous matrix molecules as in prior art.

A further object is to provide the appropriate density of energy-absorbing molecules bonded (covalently or noncovalently) in a variety of geometries such that mono layers and multiple layers of attached energy-absorbing molecules are used to facilitate the desorption of analyte molecules of varying masses.

A further object is to provide multiple combinations of surfaces modified with energy-absorbing molecules, affinity-directed analyte capture devices, phototubes, etc.

An additional object is to provide such a method and apparatus in which the substrate forming the probe tip or other sample presenting surface is derivatized with one or more affinity reagents (a variety of densities and degrees of amplification) for selective bonding with predetermined analytes or classes of analytes.

A further object is to provide such a system in which the affinity reagent chemically bonds or biologically adheres to the target analyte or class of analytes.

A still further object is to provide a method and apparatus for desorption and ionization of analytes in which unused portion of the analytes contained on the presenting surface remain chemically accessible, so that a series of chemical, enzymatic or physical treatments of the analyte may be conducted, followed by sequential analyses of the modified analyte.

A further object is to provide a method and apparatus for the combined chemical or enzymatic modifications of target analytes for the purpose of elucidating primary, secondary, tertiary, or quaternary structure of the analyte and its components.

Another object is to provide a method and apparatus for desorption and ionization of analyte materials in which cations other than protons ($H^+$) are utilized for ionization of analyte macromolecules.

Thus, in accomplishing the foregoing objects, there is provided in accordance with the present invention, an apparatus for measuring the mass of an analyte molecule of an analyte sample by means of mass spectrometry, said apparatus comprising a spectrometer tube; a vacuum means for applying a vacuum to the interior of said tube; electrical potential means within the tube for applying an accelerating electrical potential to desorbed analyte molecules from said analyte sample; sample presenting means removably insertable into said spectrometer tube, for presenting said analyte sample in association with surface associated molecule for promoting desorption and ionization of said analyte molecules, wherein said surface molecule is selected from the group consisting of energy absorbing molecule, affinity capture device, photolabile attachment molecule and combination thereof; an analyte sample deposited on said sample presenting means in association with said surface associated molecules, whereby at least a portion of said analyte molecules not consumed in said mass spectrometry analysis will remain accessible for subsequent chemical, biological or physical analytical procedures; laser beam means for producing a laser beam directed to said analyte sample for imparting sufficient energy to desorb and ionize a portion of said analyte molecules from said analyte sample; and detector means associated with said spectrometer tube for detecting the impact of accelerated ionized analyte molecules thereon.

In addition, in accomplishing the foregoing objects, there is provided in accordance with the present invention, a method in mass spectrometry to measure the mass of an analyte molecule, said method comprising the steps of: derivitizing a sample presenting surface on a probe tip face with an affinity capture device having means for binding with an analyte molecule; exposing said derivitized probe tip face to a source of said analyte molecule so as to bind said analyte molecule thereto; placing the derivitized probe tip with said analyte molecules bound thereto into one end of a time-of-flight mass spectrometer and applying a vacuum and an electric field to form an accelerating potential within the spectrometer; striking at least a portion of the analyte molecules bound to said derivitized probe tip face within the spectrometer with one or more laser pulses in order to desorb ions of said analyte molecules from said tip; detecting the mass of the ions by their time of flight within said mass spectrometer; and displaying such detected mass.

Further, in accomplishing the foregoing objects, there is provided in accordance with the present invention, a method of measuring the mass of analyte molecules by means of laser desorption/ionization, time-of-flight mass spectrometry in which an energy absorbing material is used in conjunction with said analyte molecules for facilitating desorption and ionization of the analyte molecules, wherein the improvement comprises presenting the analyte molecules on or above the surface of the energy absorbing material, wherein at least a portion of the analyte molecules not desorbed in said mass spectrometry analysis remain chemically accessible for subsequent analytical procedures.

Additionally, in accomplishing the foregoing objects, there is provided in accordance with the present invention, an apparatus for facilitating desorption and ionization of analyte molecules, said apparatus comprising: a sample presenting surface; and surface associated molecules, wherein said surface associated molecules are selected from the group consisting of energy absorbing molecule, affinity capture device, photolabile attachment molecule and combination thereof, said surface associated molecules associated with said sample presenting surface and having means for binding with said analyte molecules.

Further, there is provided a method for capturing analyte molecules on a sample presenting surface and desorbing/ionizing said captured analyte molecules from said sample presenting surface for subsequent analysis, said method comprising: derivitizing said sample presenting surface with an affinity capture device or photolabile attachment molecule having means for binding with said analyte molecules; exposing said derivitized sample present surface to a sample containing said analyte molecules; capturing said analyte molecules on said derivitized sample presenting surface by means of said affinity capture device or photolabile attachment molecule; and exposing said analyte molecules, while bound to said derivitized sample presenting surface by means of said affinity capture device or photolabile attachment molecule, to an energy or light source to desorb at least a portion of said analyte molecules from said surface.

Additionally, in accordance with the present invention, there is provided a method for preparing a surface for presenting analyte molecules for analysis, said method comprising: providing a substrate on said surface for supporting said analyte; derivitizing said substrate with an affinity capture device or photolabile attachment molecule having means for selectively bonding with said analyte; and a means for detecting said analyte molecules bonded with said affinity capture device or photolabile attachment molecule.

Further, in accomplishing the foregoing objects, there is provided in accordance with the present invention, a sample probe for promoting desorption of intact analytes into the gas phase comprising: a sample presenting surface; and an energy absorbing molecule associated with said sample presenting surface, wherein said sample probe promotes desorption of an intact analyte molecule positioned on, above or between the energy absorbing molecules when said sample probe is impinged by an energy source. Further, the energy absorbing molecule in the probe is selected from the group consisting of cinnamamide, cinnamyl bromide, 2,5-dihydroxybenzoic acid and α-cyan-4-hydroxycinnamic acid.

Additionally, in accomplishing the foregoing objects, there is provided in accordance with the present invention, a sample probe for desorption of intact analyte into the gas phase, comprising: a sample presentation surface; and a surface associated molecule wherein said surface associated molecule is a photolabile attachment molecule having at least two binding sites, wherein at least one site is bound to the sample presentation surface and at least one site is available to bind an analyte and wherein the analyte binding site is photolabile.

In addition, in accomplishing the foregoing objects there is provided in accordance with the present invention, a sample probe for promoting desorption of intact analytes into the gas phase comprising: a sample presentation surface; and either a mixture of at least two different molecules selected from the group consisting of an affinity capture device, an energy absorbing molecule and a photolabile attachment molecule associated with said sample presentation surface; wherein when an analyte is associated with said sample probe, said sample probe promotes the transition of the analyte into the gas phase when said sample probe is impinged by an energy source; or at least two different affinity capture devices associated with said sample presentation surface; wherein, when said sample probe is impinged by an energy source, said sample probe promotes the transition of an analyte molecule into the gas phase at different rates depending on the affinity capture device associated with said analyte molecule.

In addition, in accomplishing the foregoing objects there is provided in accordance with the present invention, a sample probe for promoting desorption of intact analyte into the gas phase, comprising: a sample presentation surface; and either a surface associated molecule, wherein said surface associated molecule can function both as an energy absorbing molecule and as an affinity capture device; or a surface associated molecule wherein said surface associated molecule is a photolabile attachment molecule having at least two binding sites, wherein at least one site is bound to the sample presentation surface and at least one site is available to bind an analyte and wherein the analyte binding site is photolabile.

Additionally, there is provided in the present invention, a method in mass spectrometry to measure the mass of an analyte molecule, said method comprising the steps of: derivitizing a sample presenting surface on a probe tip face with a photolabile attachment molecule (PAM), wherein said PAM has at least two binding sites, one binding site binds to the sample presenting surface and at least one binding site is available for binding with an analyte molecule; exposing said derivitized probe tip face to a source of said analyte molecule so as to bind said analyte molecule thereto; placing the derivitized probe tip with said analyte molecules bound thereto into one end of a time-of flight mass spectrometer and applying a vacuum and an electric field to form an accelerating potential within the spectrometer; striking at least a portion of the analyte molecules bound to said derivitized probe tip face within the spectrometer with one or more laser pulses in order to desorb ions of said analyte molecules from said tip; detecting the mass of the ions by their time of flight within said mass spectrometer; and displaying such detected mass.

In addition, there is provided a method of measuring the mass of analyte molecules by means of laser desorption/ionization, time-of-flight mass spectrometry in which a photolabile attachment molecule (PAM) is used in conjunction with said analyte molecules for facilitating desorption and ionization of the analyte molecules, the improvement comprising: presenting the analyte molecules on or above the surface of the PAM, wherein at least a portion of the analyte molecules not desorbed in said mass spectrometry analysis remain chemically accessible for subsequent analytical procedures.

There is further provided in accordance with the present invention, a sample probe for promoting of differential desorption of intact analyte into the gas phase, comprising: a sample presentation surface; and at least two different photolabile attachment molecules associated with said sample presentation surface; wherein, when said sample probe is impinged by an energy source, said sample probe promotes the transition of an analyte molecule into the gas phase at different rates depending on the photolabile attachment molecule associated with said analyte molecule.

Additionally, there is provided in accordance with the present invention, a sample probe for promoting desorption of intact analytes into the gas phase comprising: a sample presenting surface; and a photolabile attachment molecule associated with said sample presenting surface; wherein, when said sample probe is impinged by an energy source, said sample probe promotes the transition of an intact analyte molecule into the gas phase.

Further, there is provided in accordance with the present invention, a method for biopolymer sequence determination comprising the steps of: binding a biopolymer analyte to probe tip containing a sample presenting surface having a surface selected molecule selected from the group consisting of an energy absorbing molecule, an affinity capture device, a photolabile attachment molecule and a combination thereof; desorption of biopolymer analyte in mass spectrometry analysis, wherein at least a portion of said biopolymer is not desorbed from the probe tip; analyzing the results of the desorption modifying the biopolymer analyte still bound to the probe tip; and repeating the desorption, analyzing and modifying steps until the biopolymer is sequenced.

Other and further objects, features and advantages will be apparent and the invention more readily understood from a reading of the following specification and by reference to the accompanying drawings forming a part thereof, wherein the examples of the presently preferred embodiments of the invention are given for the purposes of disclosure.

BRIEF DESCRIPTION OF THE DRAWINGS

The foregoing and other objects and advantages of the invention will be apparent from the following specification and from the accompanying drawings.

FIG. 1 (lower profile) shows the sequential in situ metal (Cu)-binding of the peptides in the presence of neutral energy absorbing molecules.

FIG. 2 (second from top profile) shows the sequential in situ 5 min alkaline phosphatase digestion to remove phosphate groups from the phosphopeptide. FIG. 2 (third from top profile) shows the mass spectrum of the phosphopeptide after further in phosphatase digestion in the presence of acidic energy absorbing molecules (2,5 dihydroxybenzoic acid, pH 2) as described in prior art.

SEAC

Figure 5A:
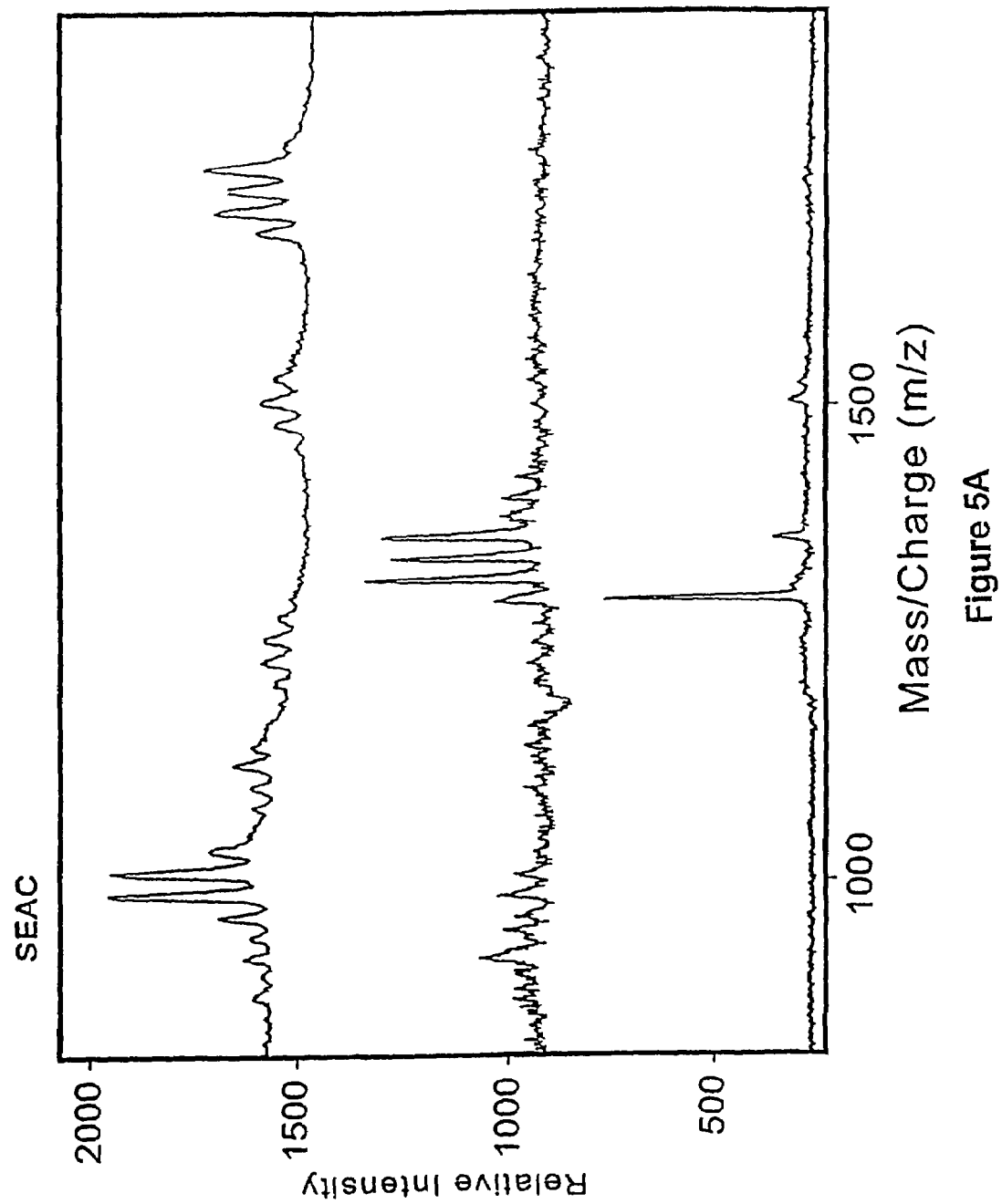
Figure 5B:
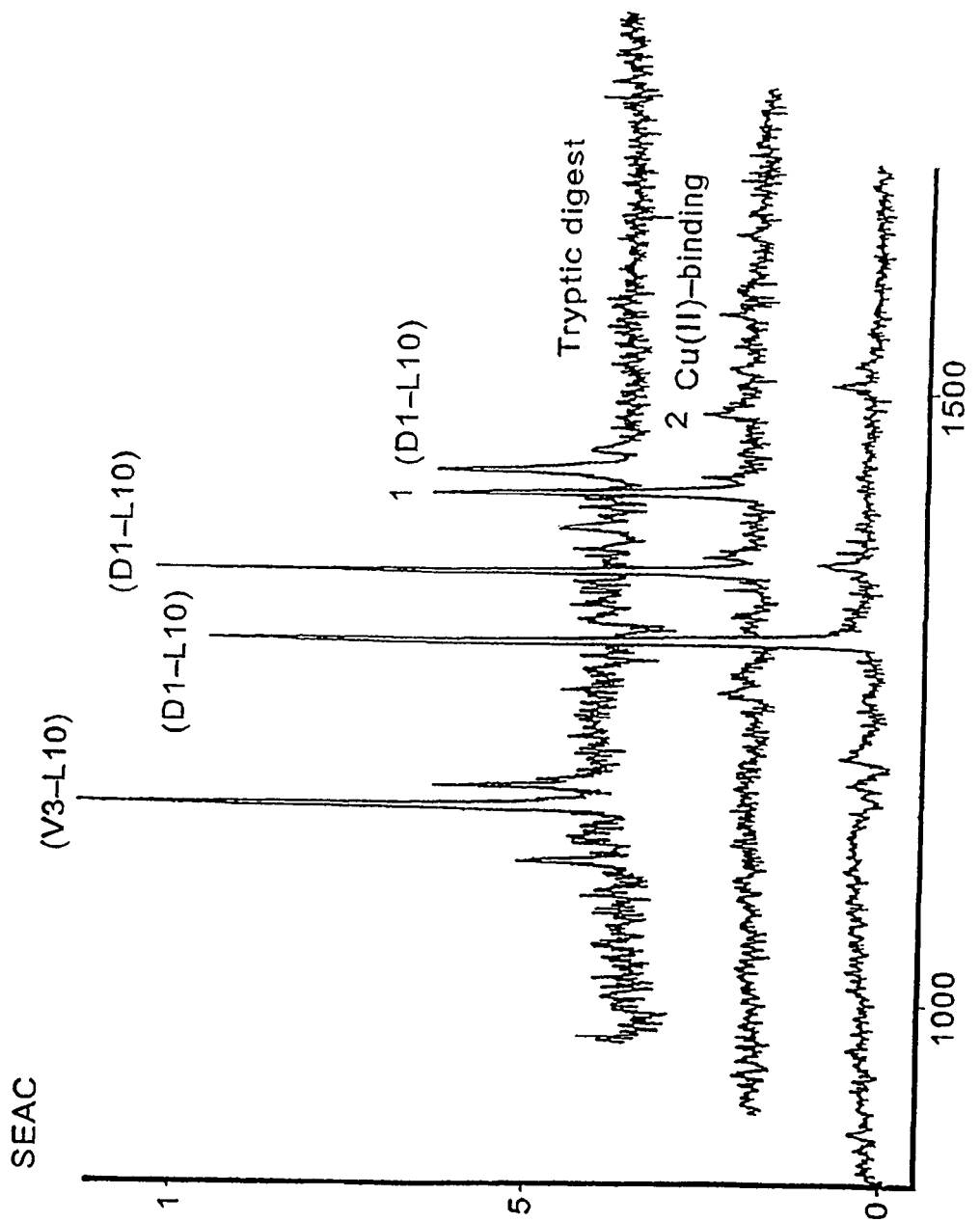

FIG. 5A, top profile, shows the mass spectrum of sperm activating factor (933 Da) and neurotensin (1655 Da) (and their multiple Na-adducts) in the peptide solution unadsorbed by the IDA-Cu(II) surface. FIG. 5A, middle profile, shows the mass spectrum of angiotensin I (1296.5 Da) plus Na-adduct peaks that were selectively adsorbed on the IDA-Cu(II) surface. FIG. 5A, bottom profile, and FIG. 5B, bottom profile, show the mass spectrum of the same angiotensin I adsorbed on IDA-Cu(II) after water wash. FIG. 5B, middle profile, shows the sequential in situ copper-binding (1 and 2 Cu) by affinity adsorbed angiotensin I. FIG. 5B, top profile, shows the sequential in situ trypsin digestion of the affinity adsorbed angiotensin I.

Figure 6:
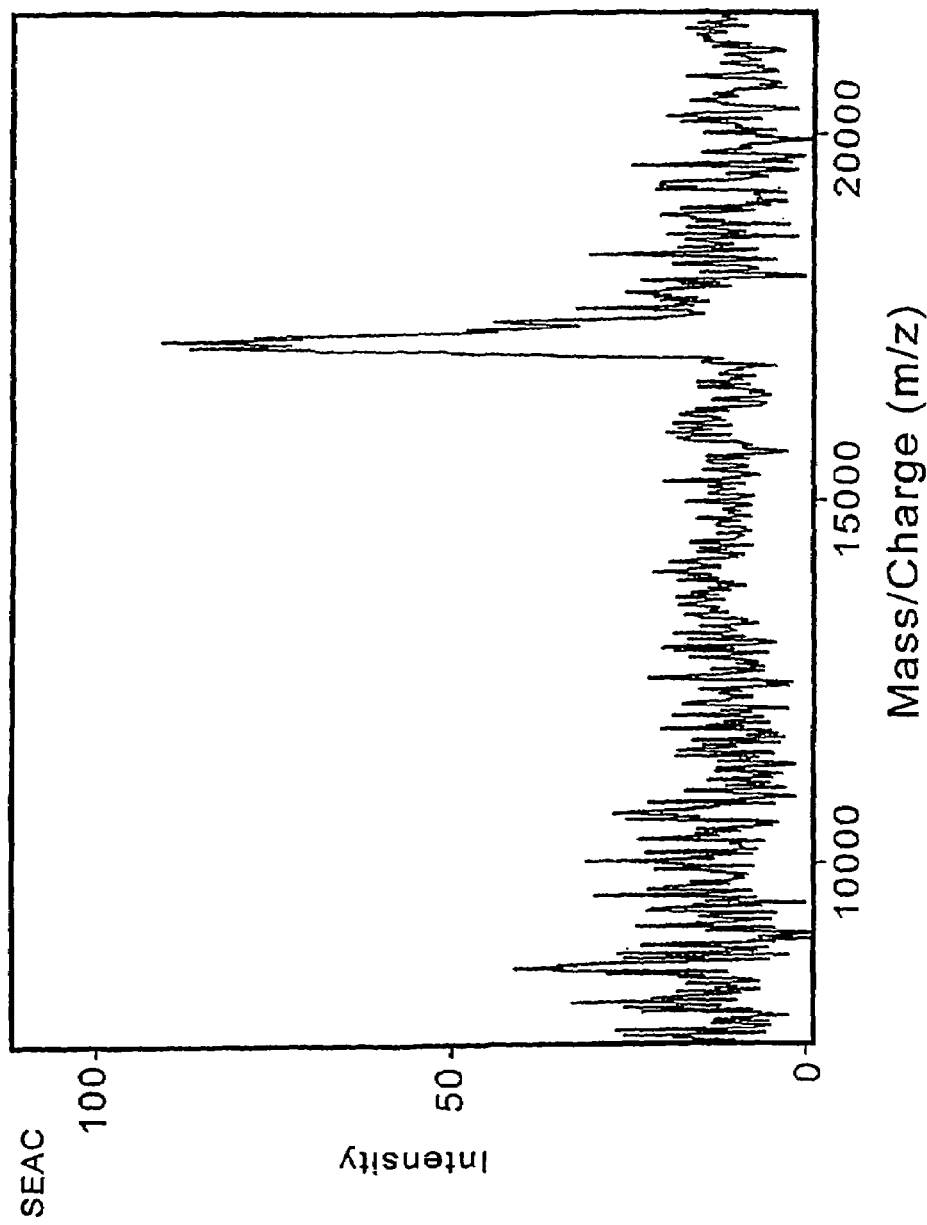

FIG. 6 shows the mass spectrum of myoglobin (4 to 8 fmole) affinity adsorbed on IDA-Cu(II) surface.

Figure 7:
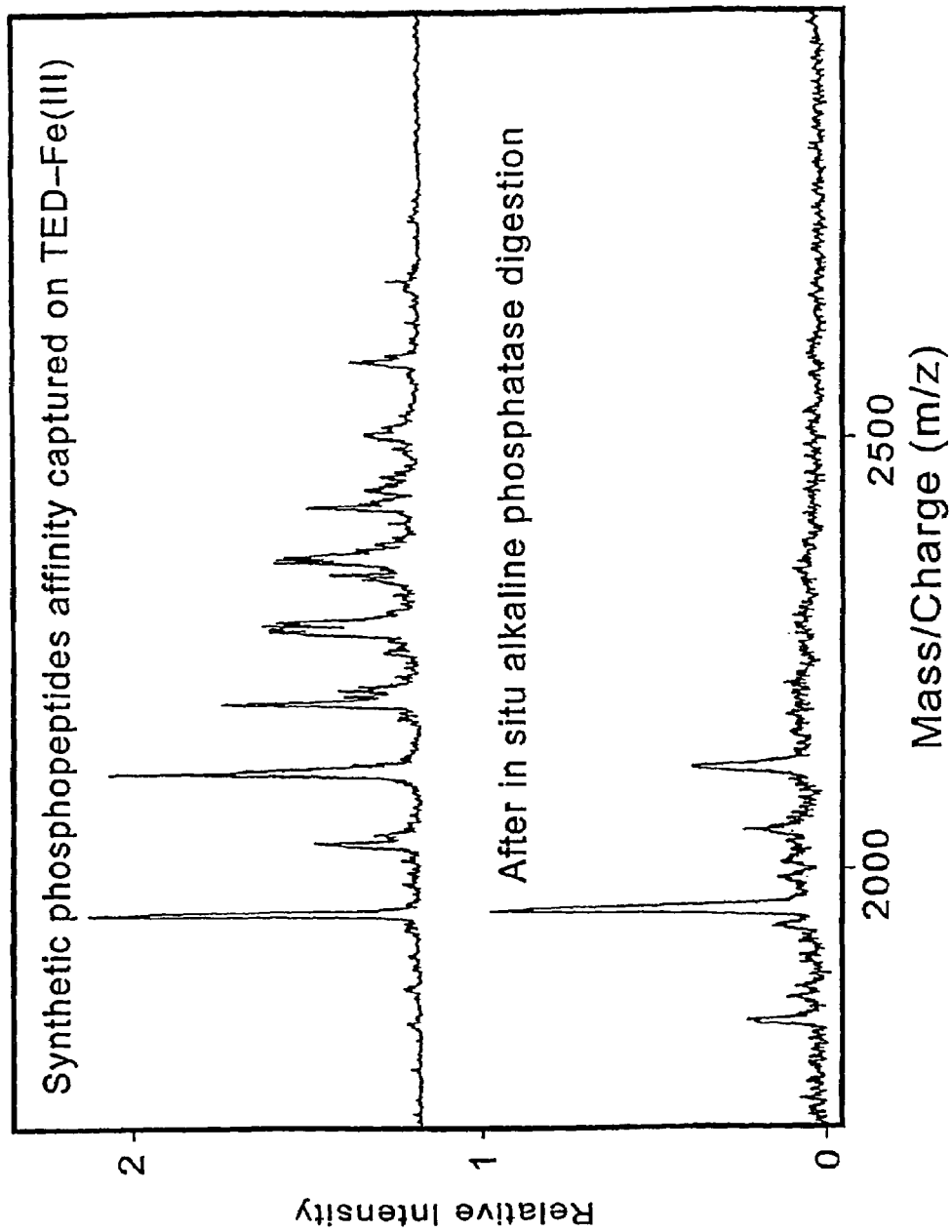

FIG. 7 (top profile) shows the mass spectrum of synthetic casein peptide (1934 Da) with multiple phosphorylated forms affinity adsorbed from a crude mixture on TED-Fe(III) surface. After sequential in situ alkaline phosphatase digestion, only the original nonphosphorylated form remained (lower profile).

Figure 8:
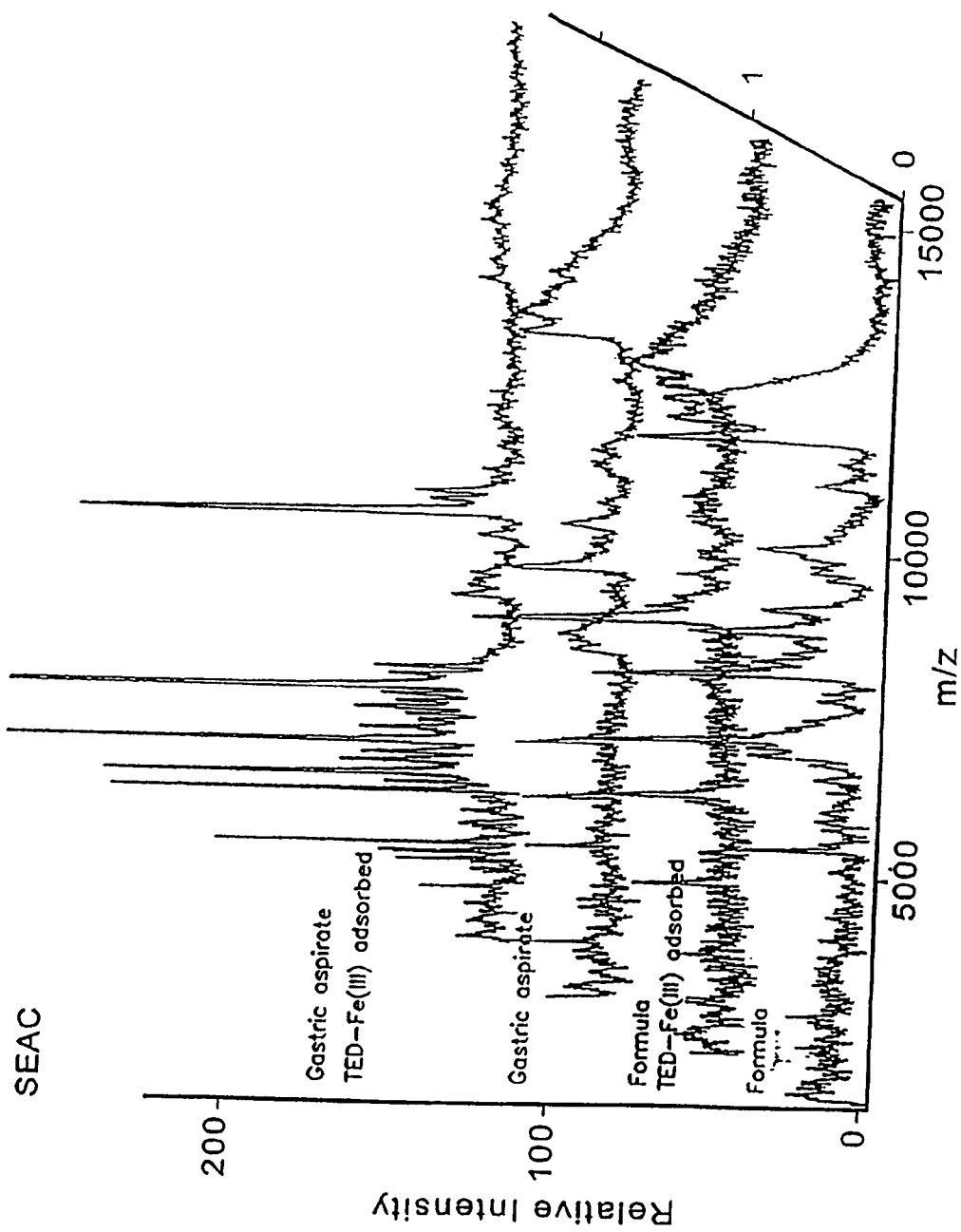

FIG. 8, bottom profile, shows the mass spectrum of total proteins in infant formula. FIG. 8, second from bottom profile, shows the mass spectrum of phosphopeptides in infant formula affinity adsorbed on TED-Fe(III) surface. FIG. 8, second from top profile, shows the mass spectrum of total proteins in gastric aspirate of preterm infant obtained after feeding the infant formula. FIG. 8, top profile, shows the mass spectrum of phosphopeptides in the gastric aspirate affinity adsorbed on TED-Fe(III) surface.

Figure 9A:
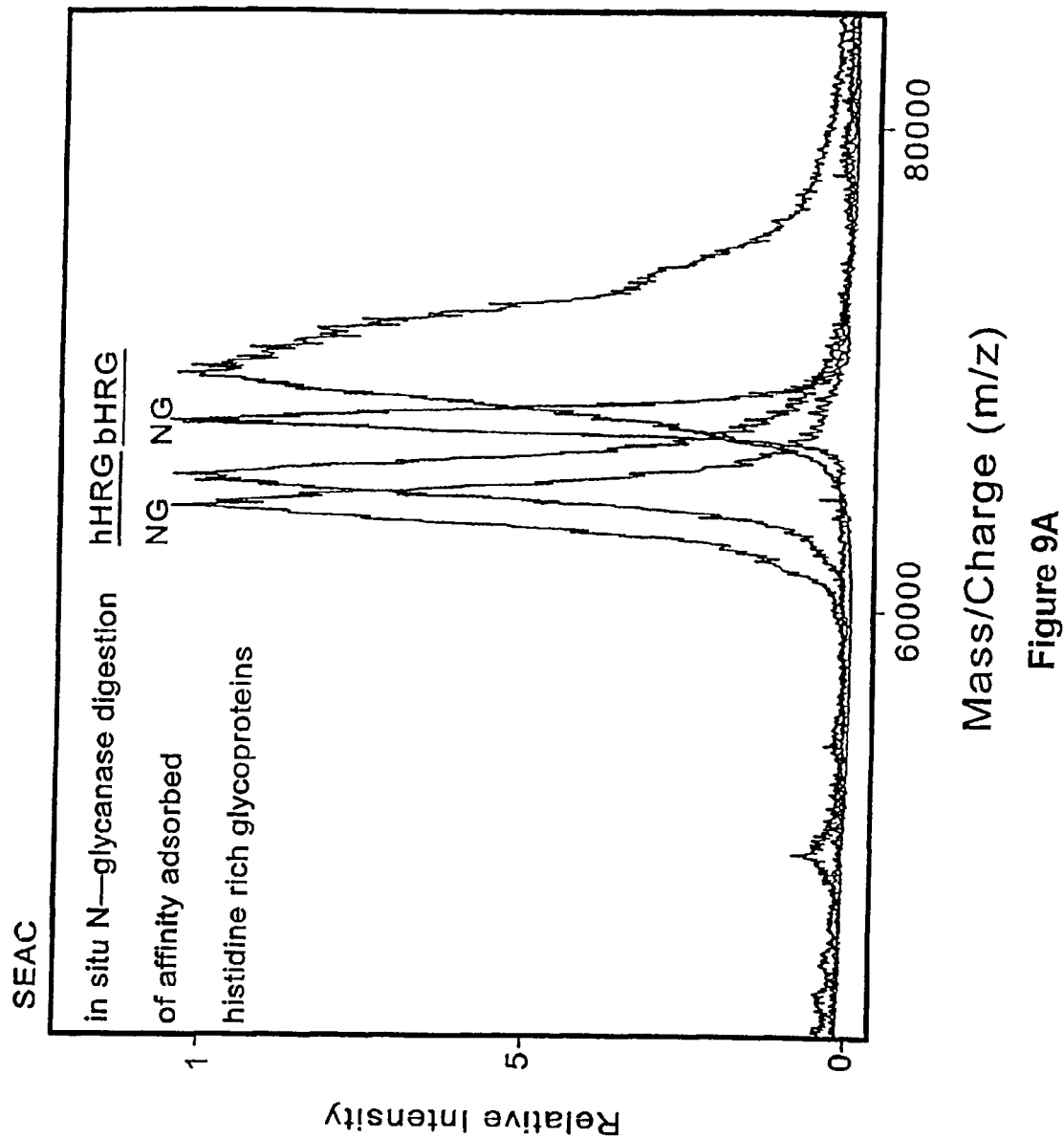
Figure 9B:
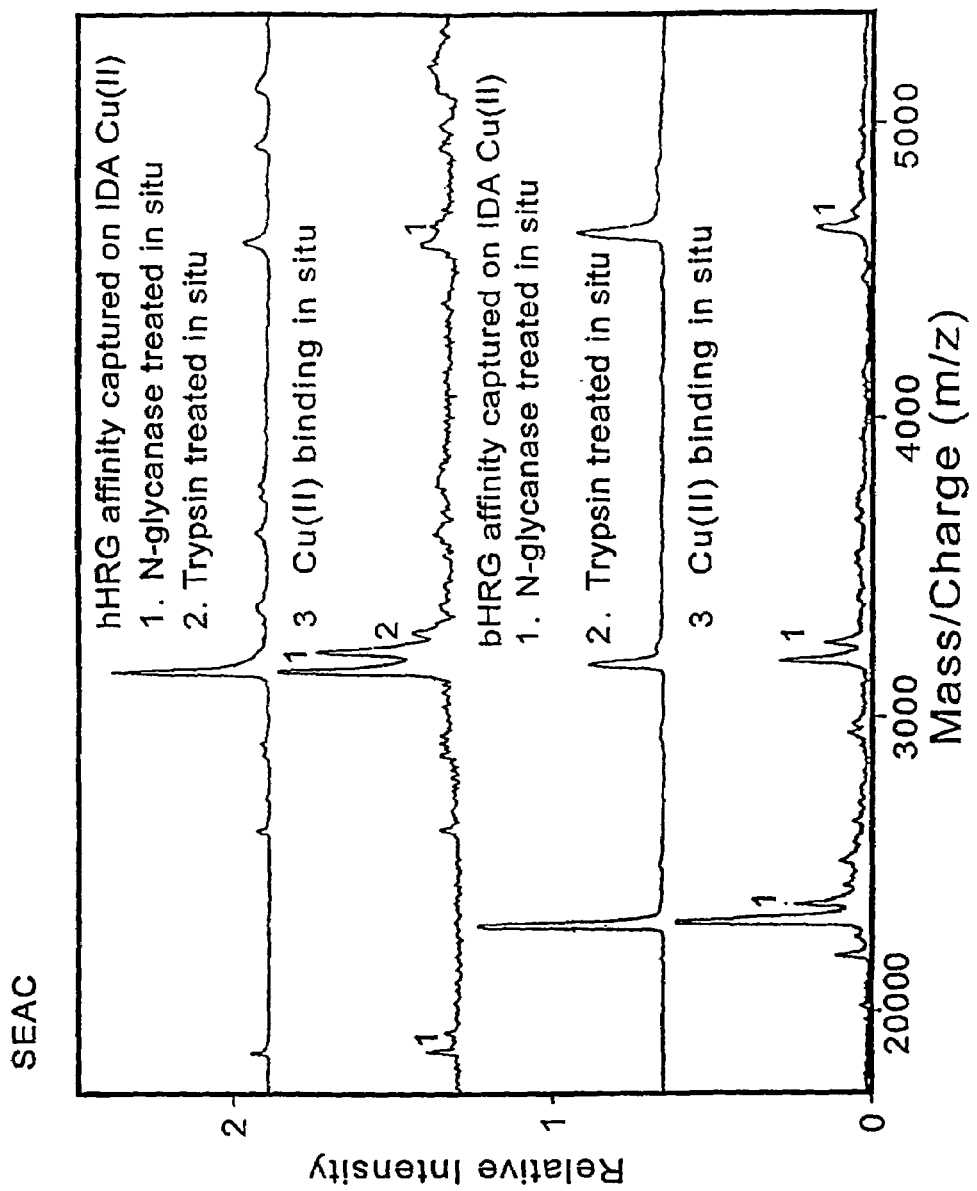
Figure 9C:
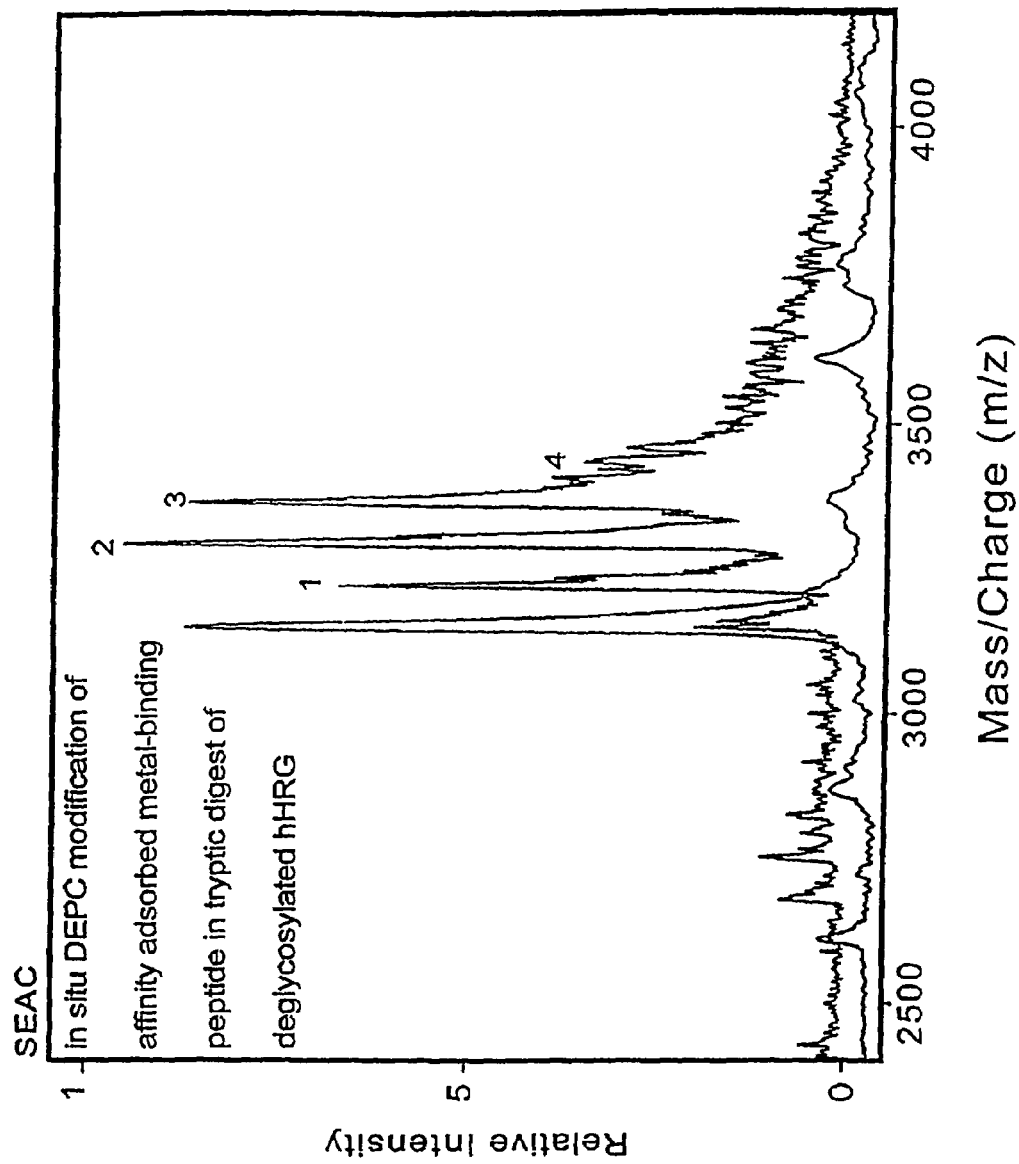
Figure 9D:
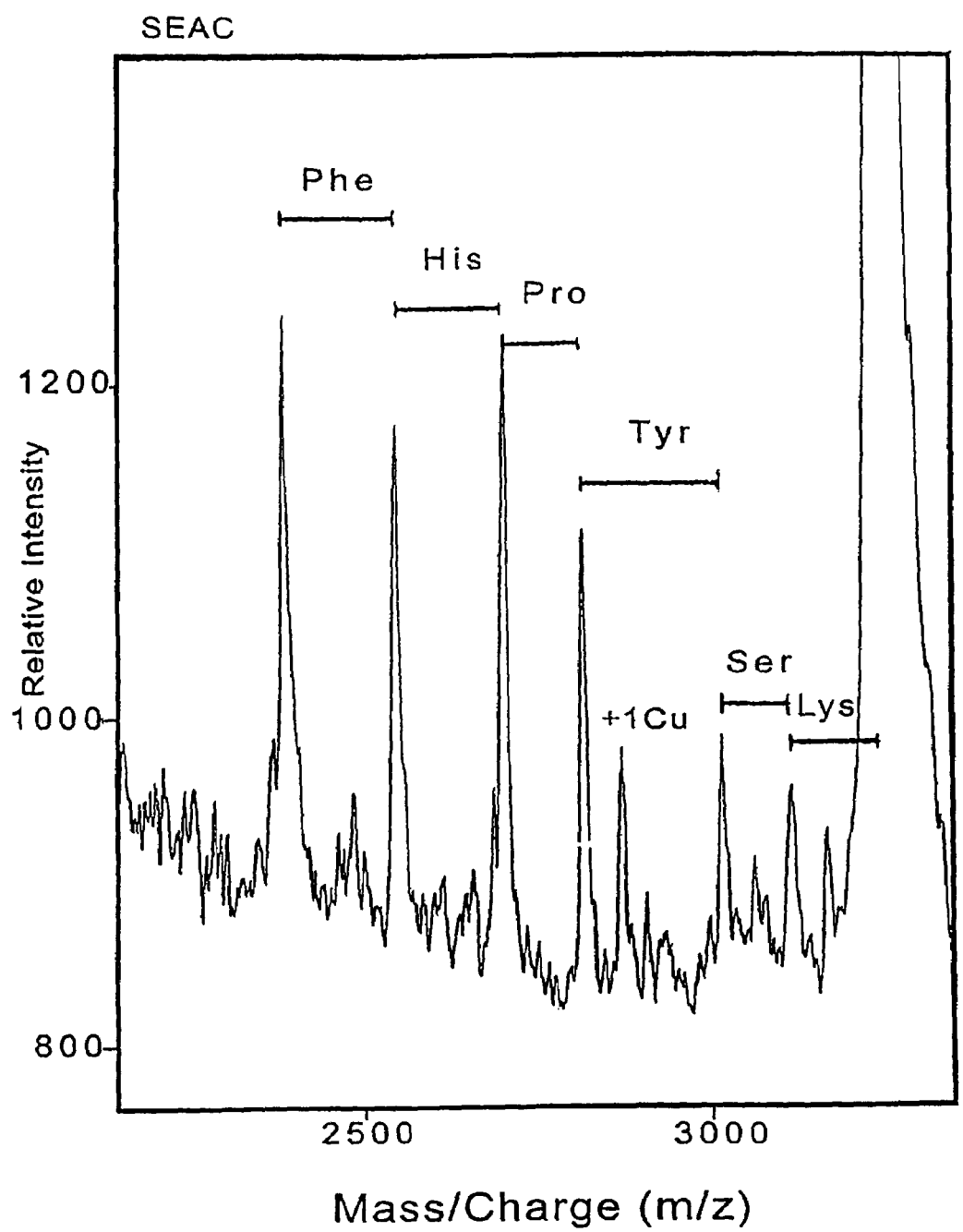

FIG. 9A shows the composite mass spectra of human and bovine histidine-rich glycoprotein adsorbed on IDA-Cu(II) surface before and after N-glycanase digestion. The mass shifts represent the removal of carbohydrate from the respective glycoproteins. FIG. 9B shows the composite mass spectra of trypsin digested peptides from the deglycosylated proteins of the two species (top profile for human protein, second from bottom profile for bovine protein) and in situ Cu(II)-binding of the trypsin digested peptides of the two species (second from top profile for human protein, bottom profile for bovine protein; the numbers 1, 2 indicate the number of copper bound). FIG. 9C shows that one such Cu(II)-binding peptide (bottom profile) has at least 4 His residues which are specifically modified by diethylpyrocarbonate to form 4 N-carbethoxy-histidyl adducts (1-4, top profile). FIG. 9D shows the partial C-terminal sequence of the major Cu-binding peptide in the bovine histidine rich glycoprotein.

Figure 10:
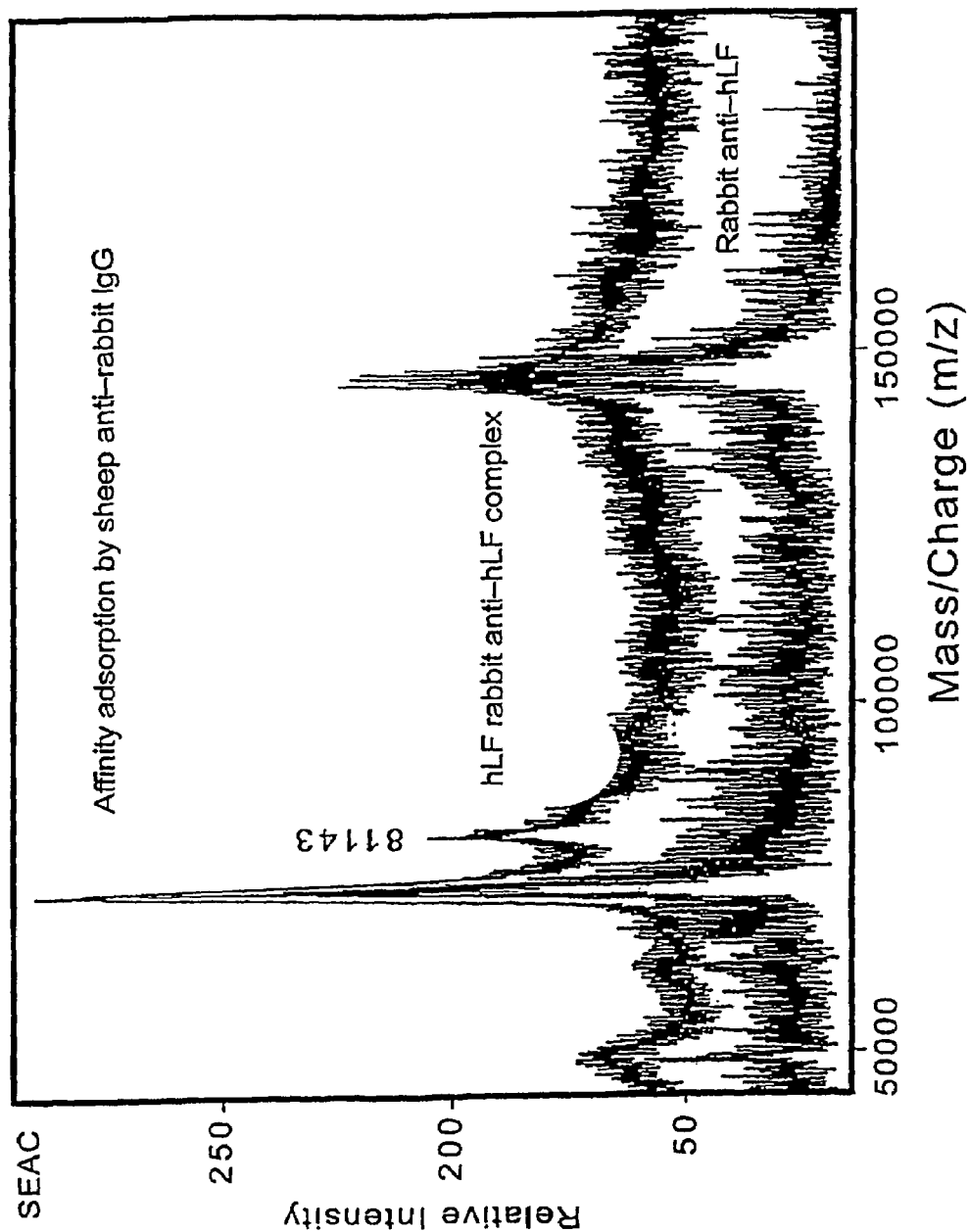

FIG. 10 (bottom profile) shows the mass spectrum of rabbit anti-human lactoferrin immunoglobulin alone (control) affinity adsorbed on sheep anti-rabbit IgG paramagnetic surface. The top profile shows the mass spectrum of human lactoferrin and rabbit anti-human lactoferrin immunoglobulin complex affinity adsorbed on sheep anti-rabbit IgG paramagnetic surface.

Figure 11A:
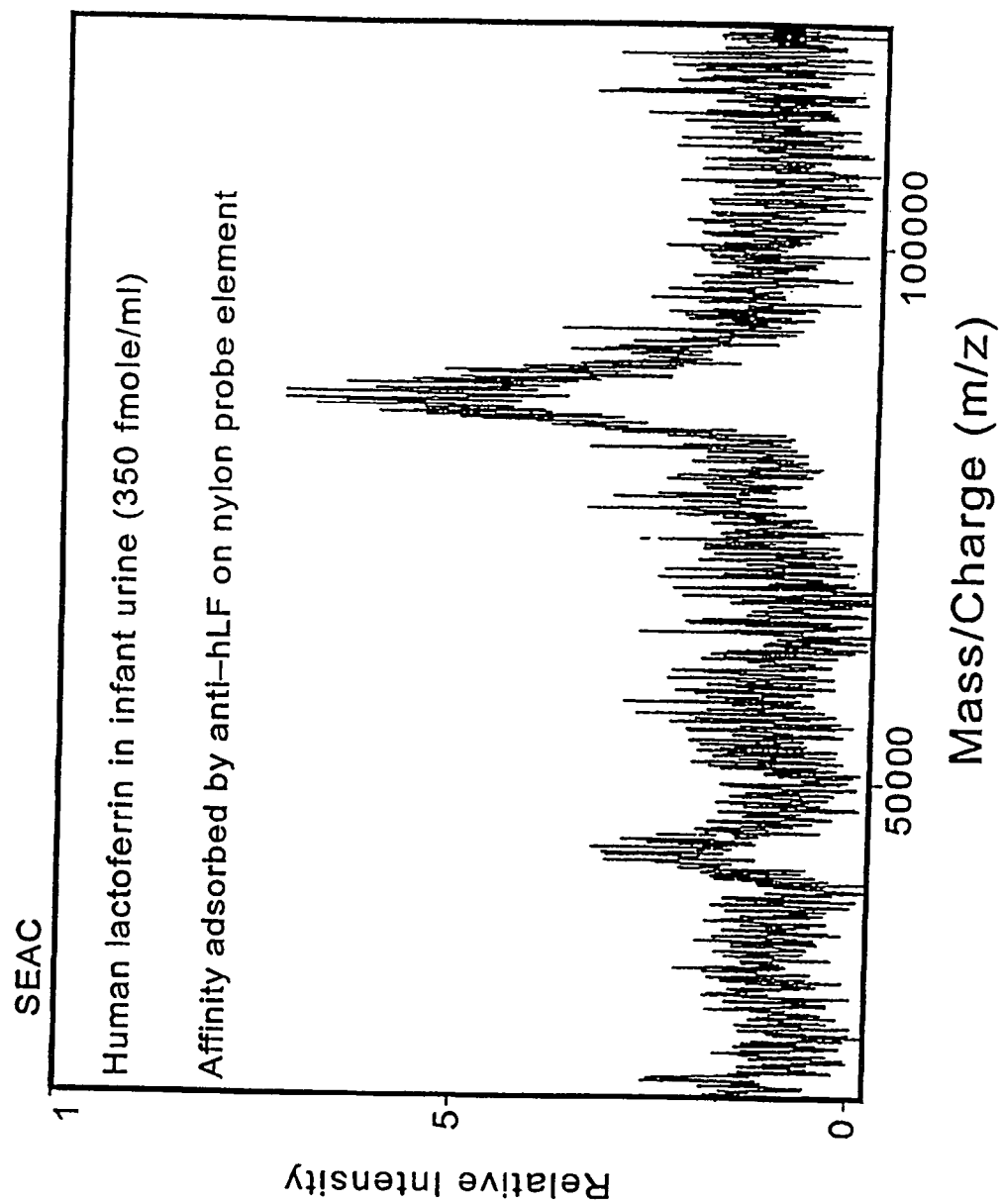
Figure 11B:
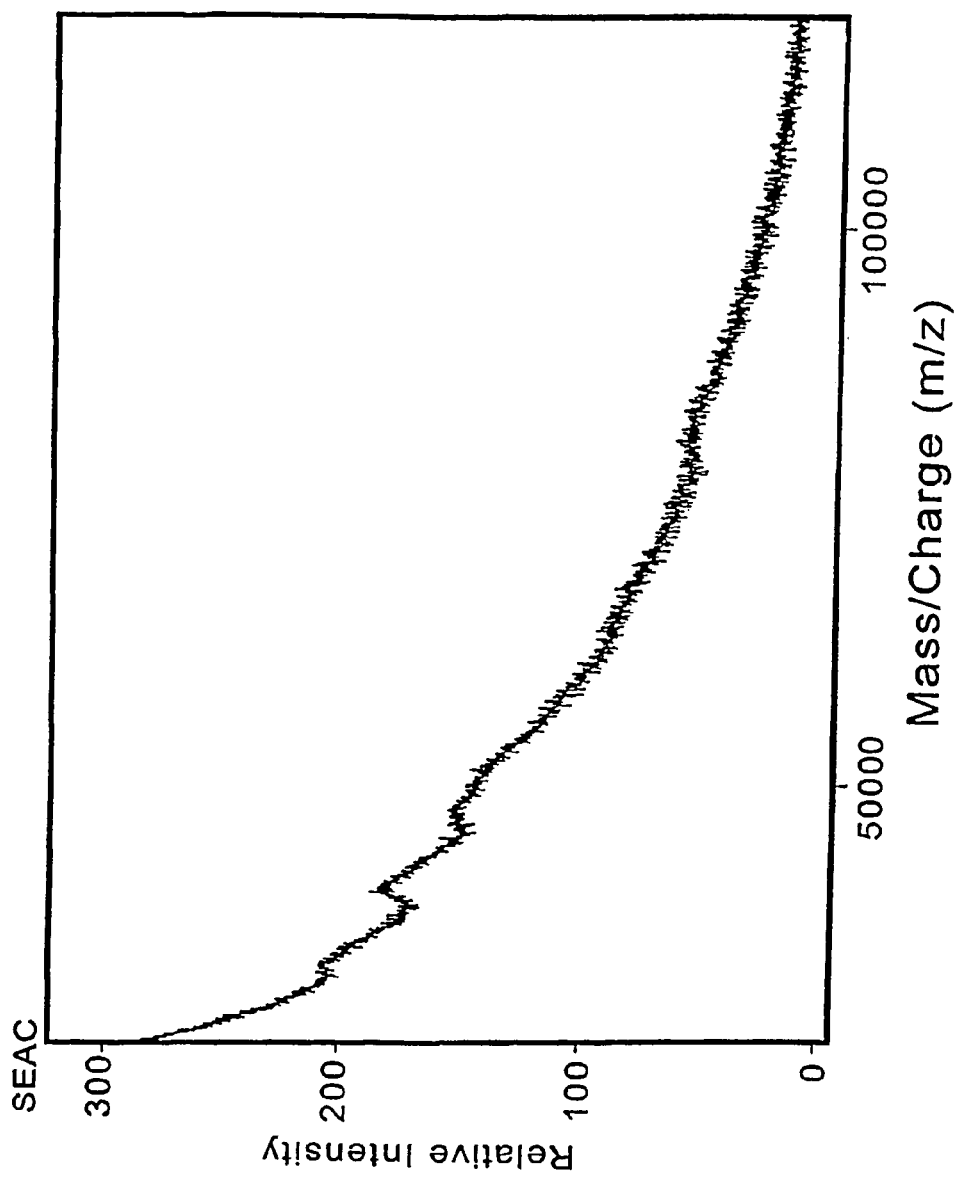

FIG. 11A shows the mass spectrum of human lactoferrin affinity adsorbed from preterm infant urine on a anti-human lactoferrin immunoglobulin nylon surface. FIG. 11B shows the equivalent mass spectrum of whole preterm infant urine containing 1 nmole/ml of lactoferrin.

Figure 12:
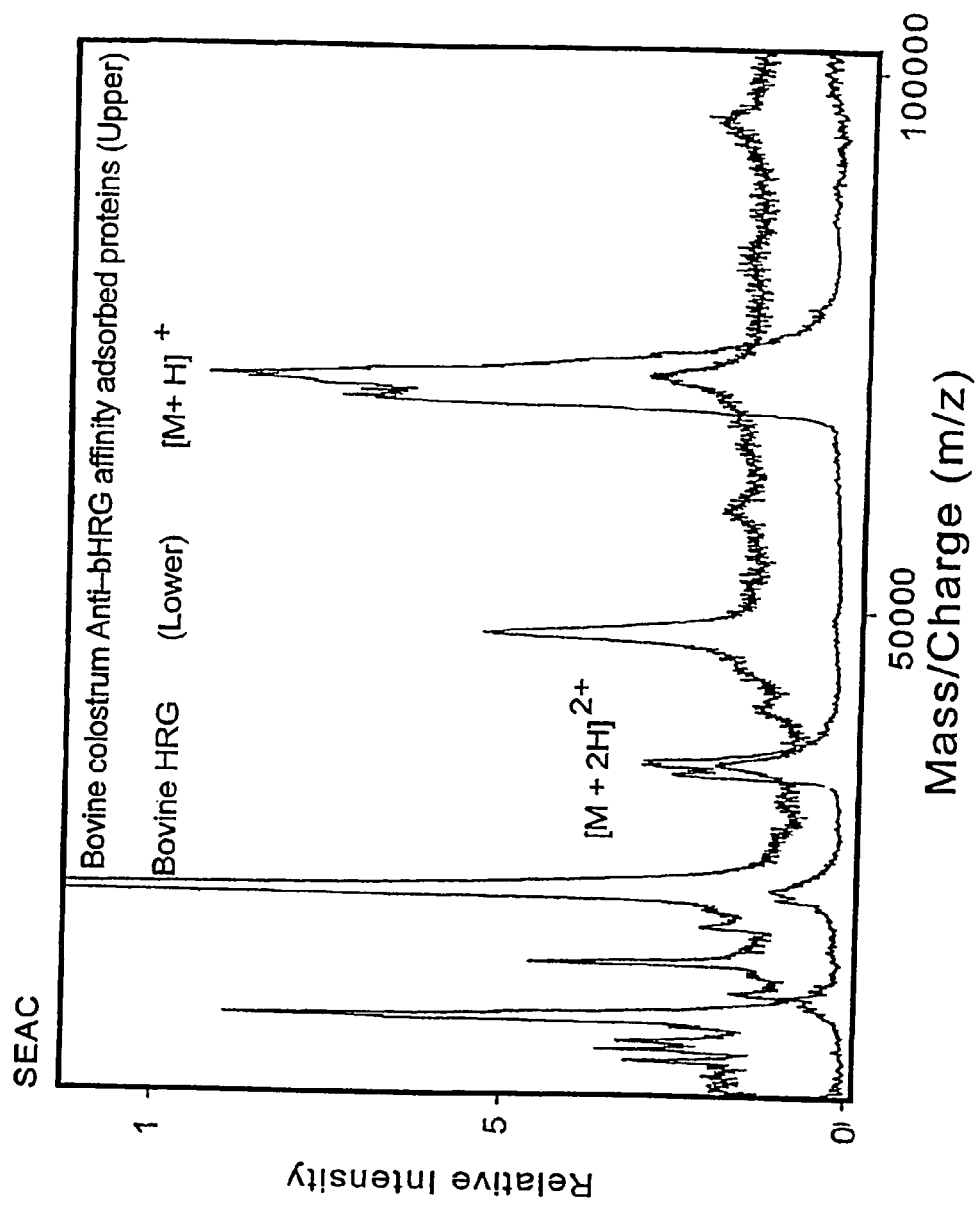

FIG. 12 (lower profile) shows the mass spectrum of pure bovine histidine rich glycoprotein. The upper profile shows the mass spectrum of bovine histidine rich glycoprotein and fragments affinity adsorbed from bovine colostrum on antibovine histidine rich glycoprotein immunoglobulin surface.

Figure 13:
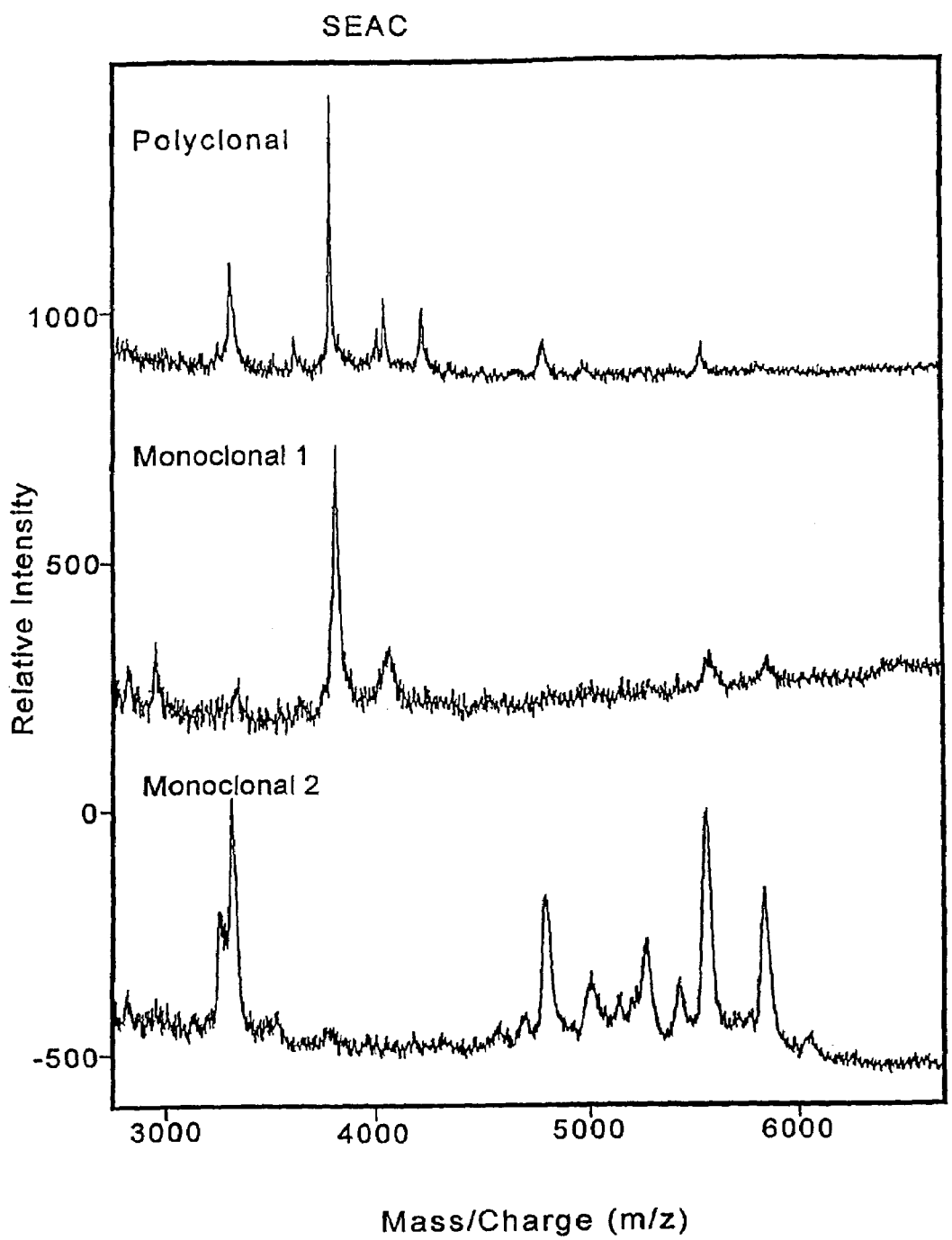

FIG. 13 shows the composite mass spectra of the peptides of follicle stimulating hormone recognized by the different anti-follicle stimulating hormone antibodies.

Figure 14:
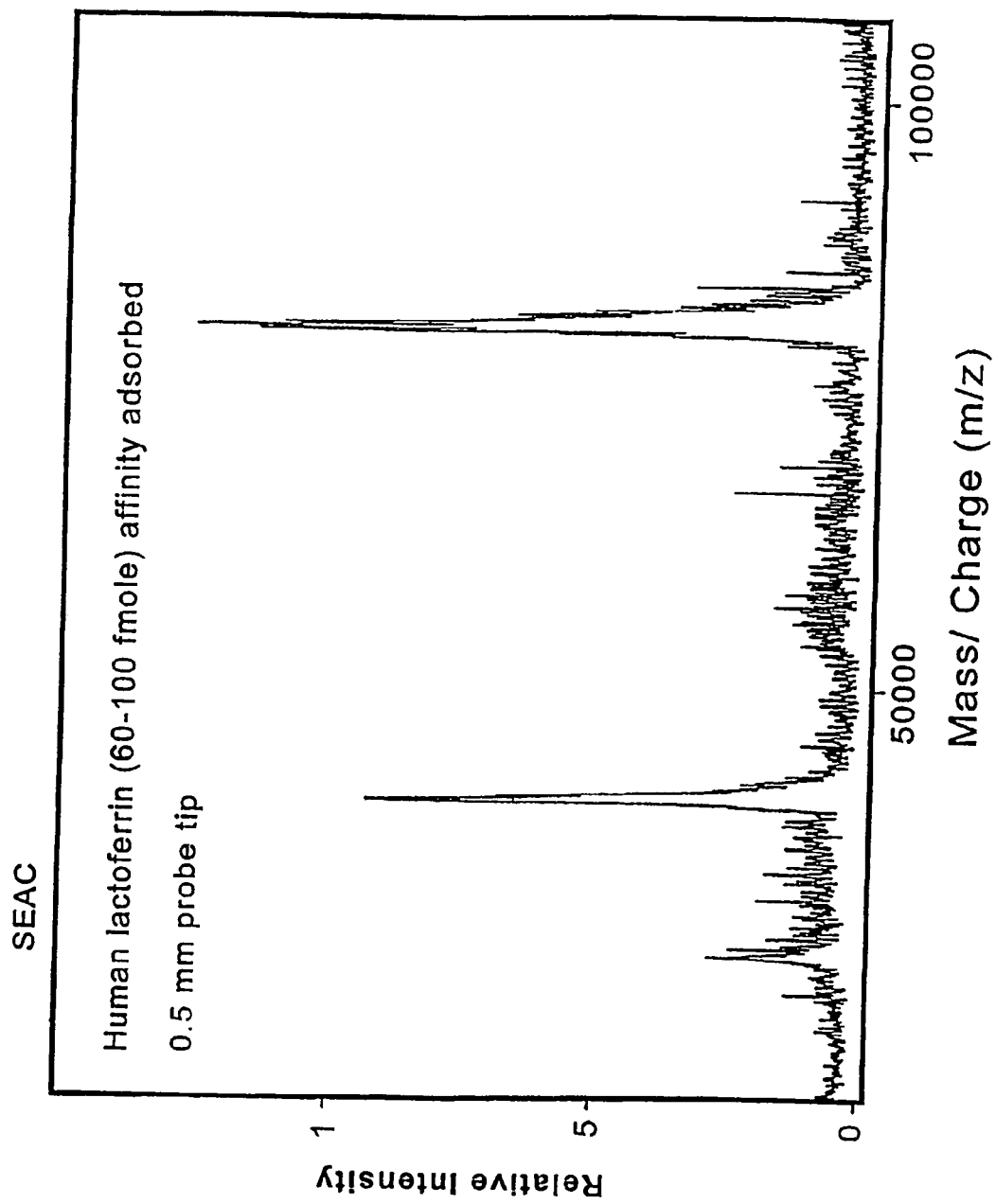

FIG. 14 shows the mass spectrum of human lactoferrin affinity adsorbed on a single bead of single-stranded DNA agarose deposited on a 0.5 mm diameter probe element.

Figure 15:
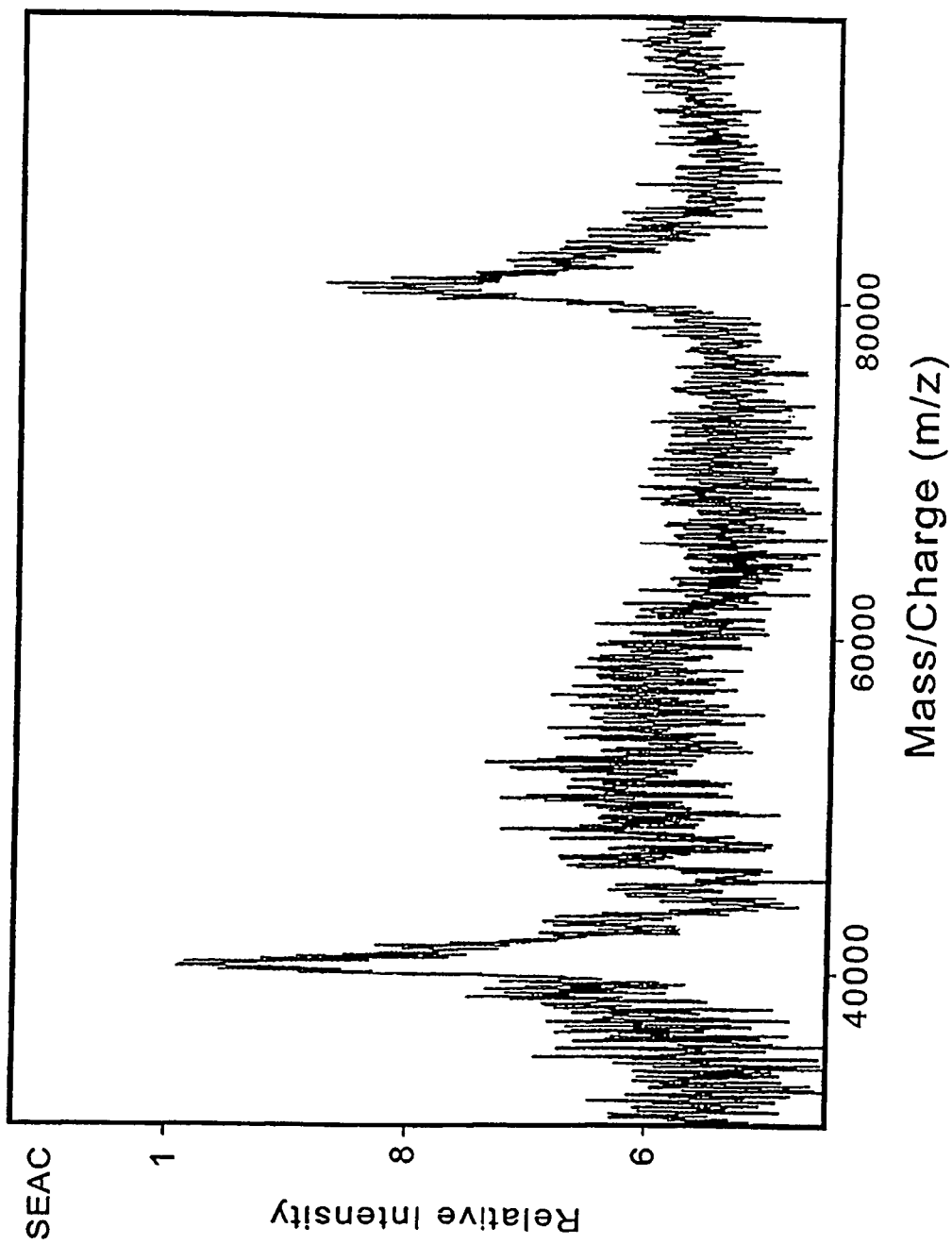

FIG. 15 shows the mass spectrum of human lactoferrin affinity adsorbed from preterm infant urine on single-stranded DNA surface.

Figure 16A:
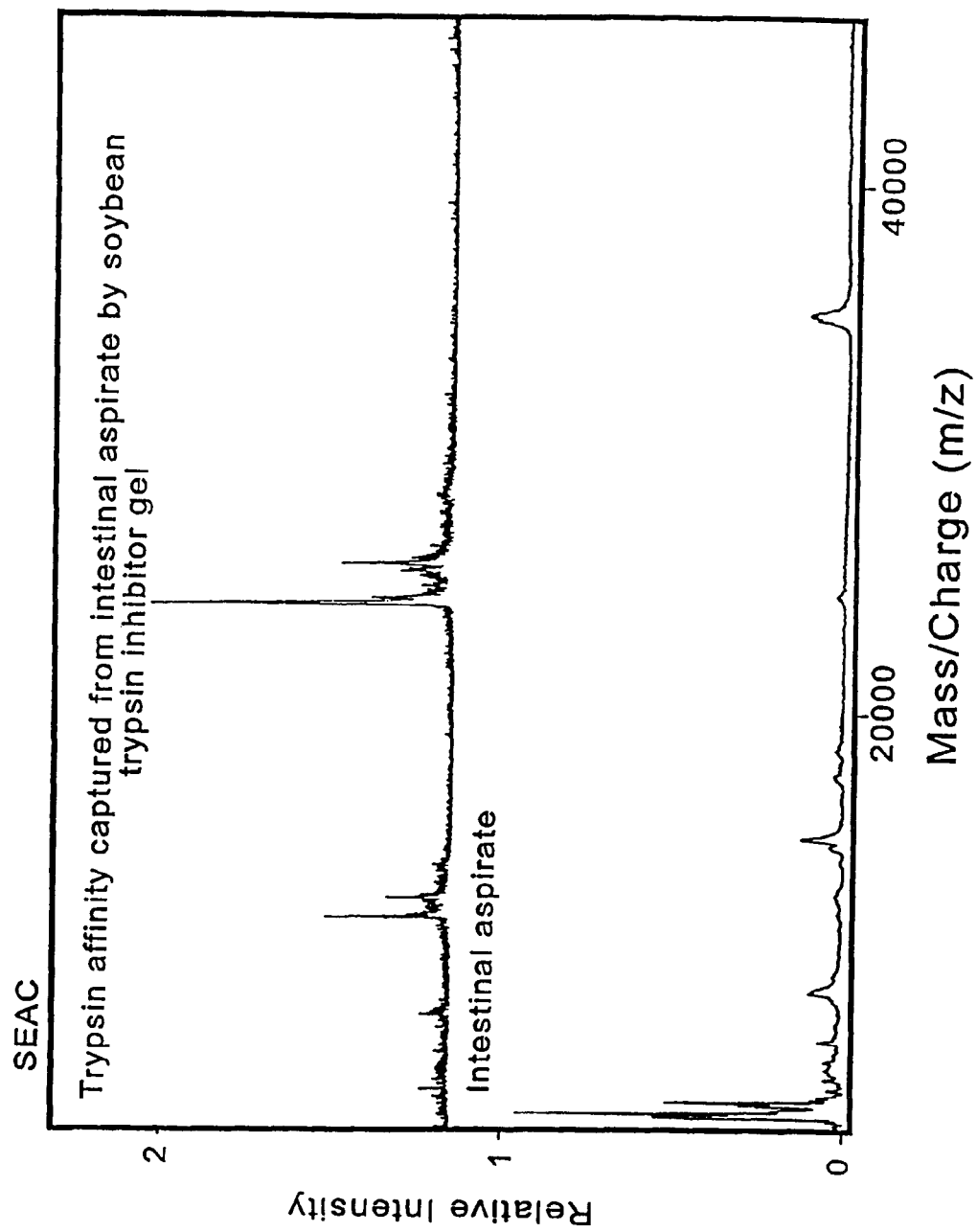
Figure 16B:
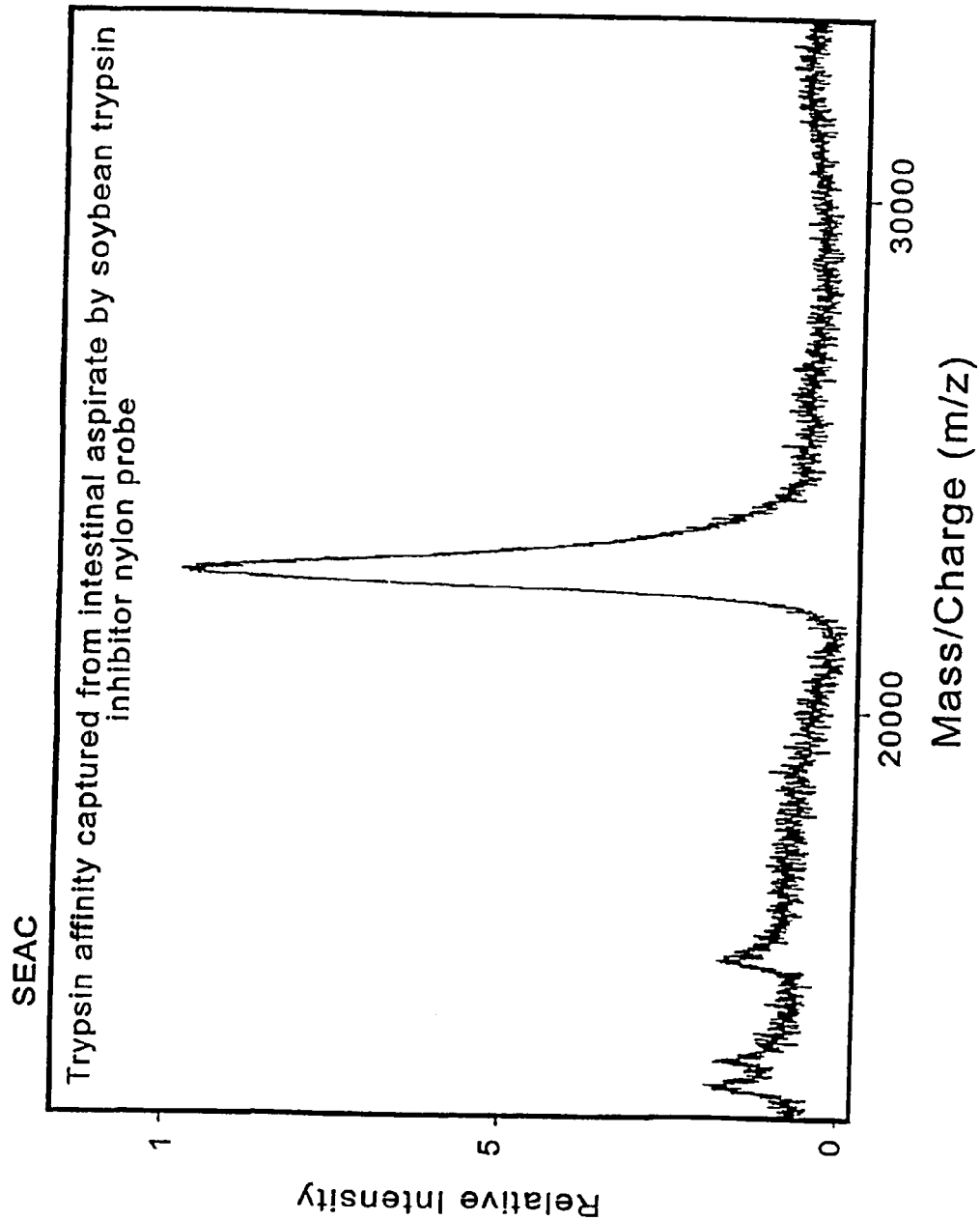

FIG. 16A shows the composite mass spectra of the total proteins in human duodenal aspirate (lower profile) and the trypsin affinity adsorbed from the aspirate on a soybean trypsin inhibitor surface (upper profile). FIG. 16B stows the mass spectrum of trypsin affinity adsorbed from 1 ul of aspirate on a soybean trypsin inhibitor nylon surface.

Figure 17A:
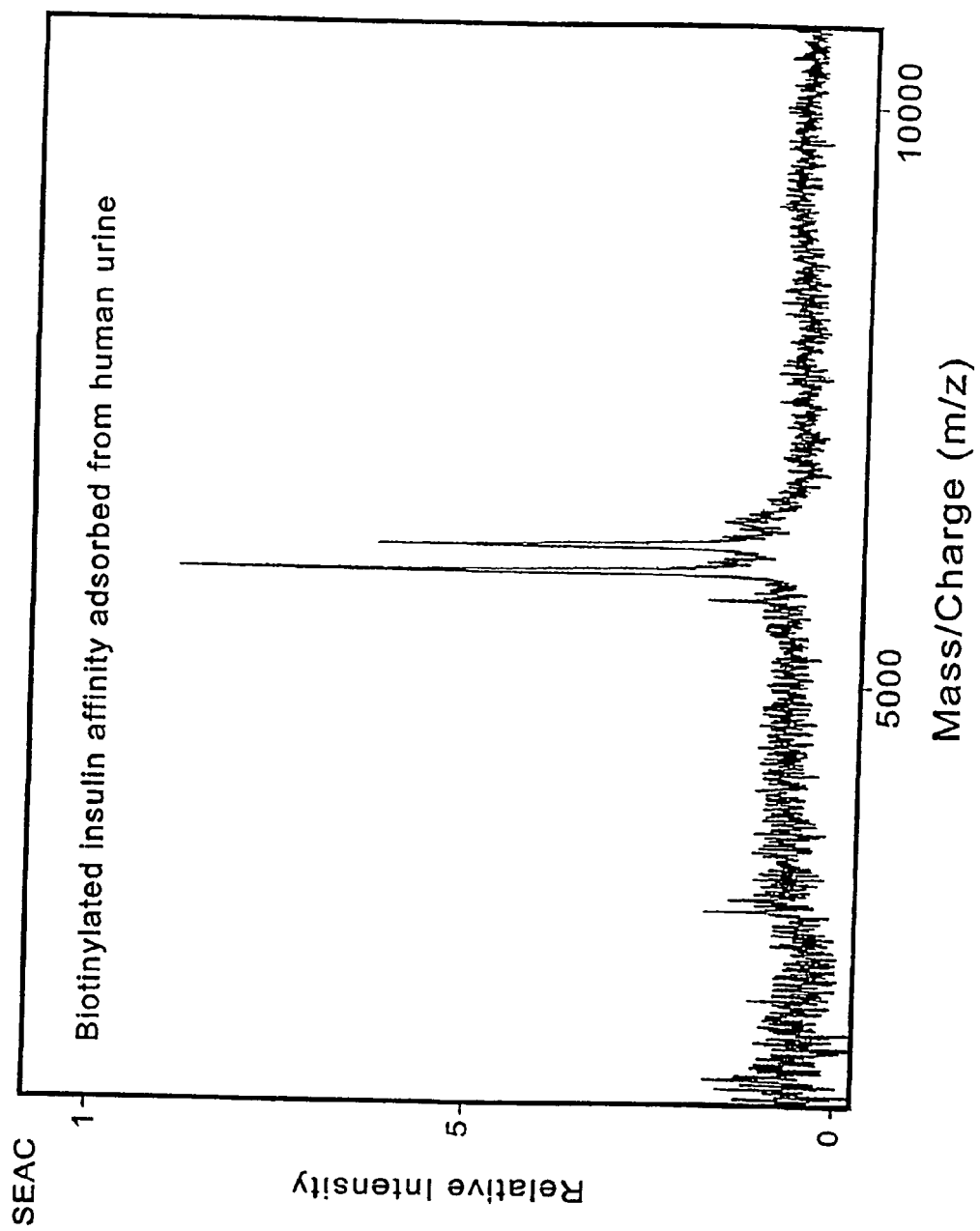
Figure 17B:
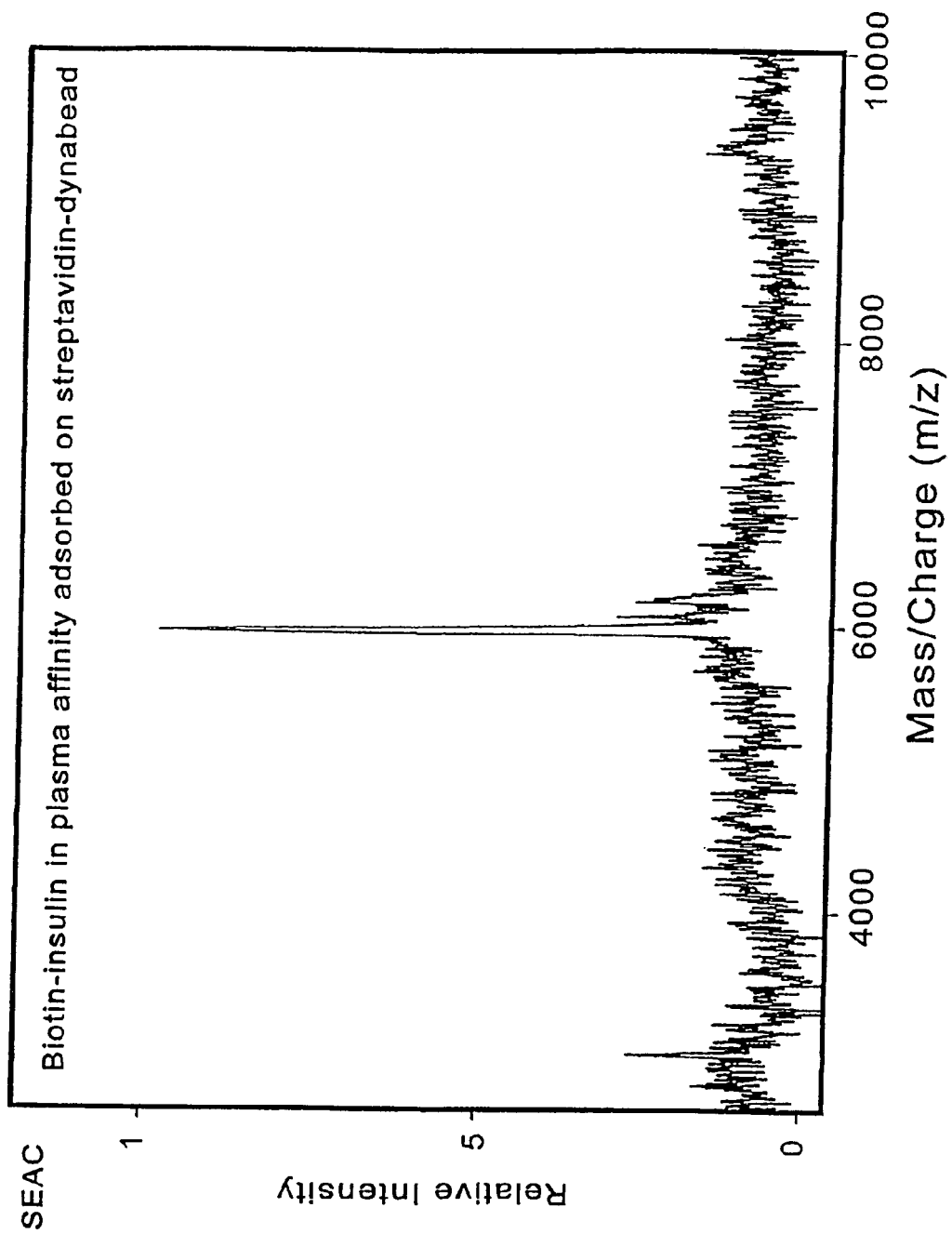

FIG. 17A shows the mass spectrum of biotinylated insulin affinity adsorbed from human urine on a Streptavidin surface. FIG. 17B shows the mass spectrum of biotinylated insulin affinity adsorbed from human plasma on a Streptavidin surface.

Figure 18:
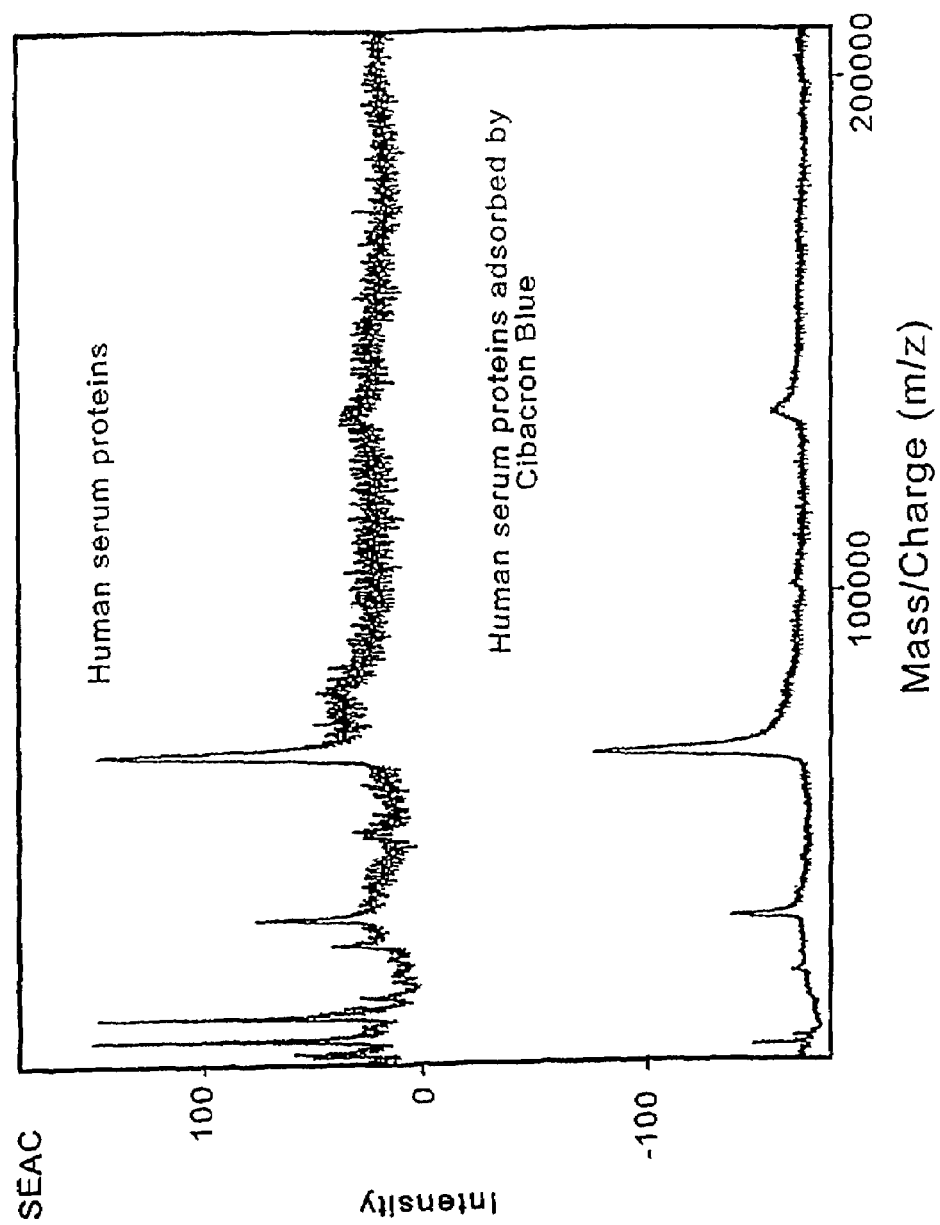

FIG. 18 (upper profile) shows the mass spectrum of total proteins in human serum. FIG. 18 (lower profile) shows the mass spectrum of serum albumin affinity adsorbed from human serum on a Cibacron-blue surface.

SEND

Figure 19:
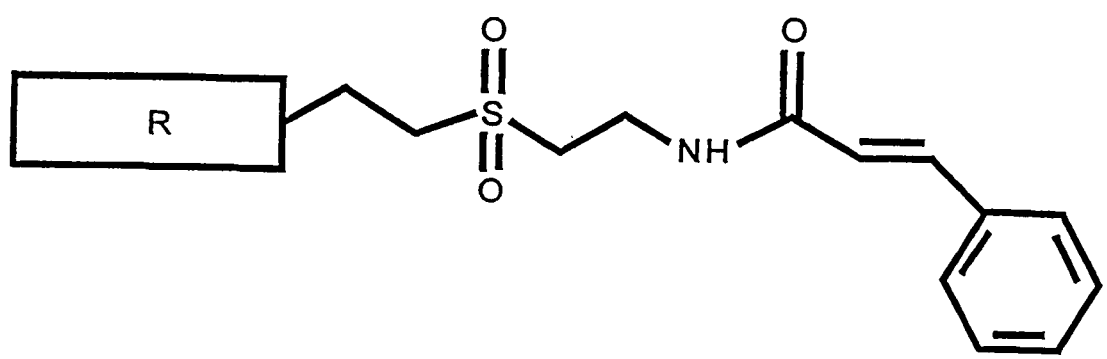

FIG. 19 shows the molecular structure of surface bound cinnamamide; R represents the surface plus cross-linker.

Figure 20:
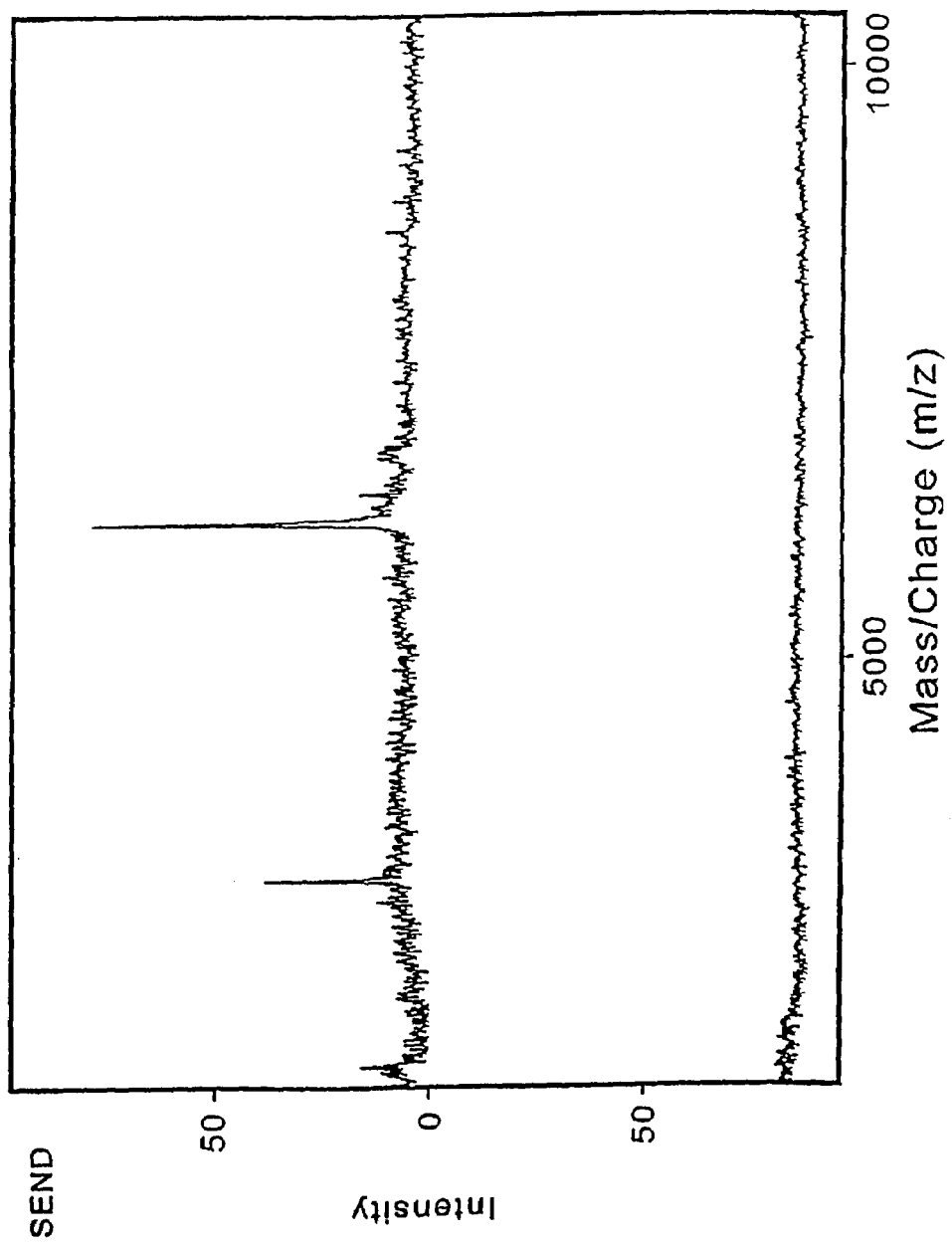

FIG. 20 (upper profile) shows the mass spectrum of peptide mixtures desorbed from surface bound cinnamamide. FIG. 20 (lower profile) shows the mass spectrum of the same peptide mixtures with free cinnamamide.

Figure 21:
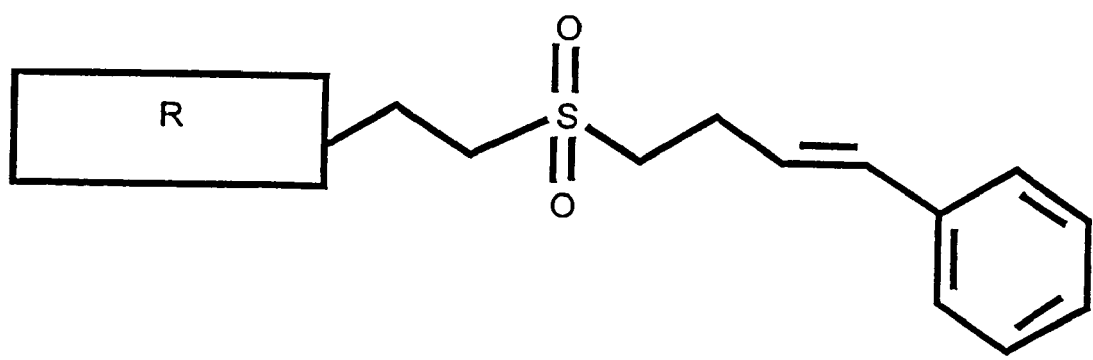

FIG. 21 shows the molecular structure of surface bound cinnamyl bromide; R represents the surface plus cross-linker.

Figure 22:
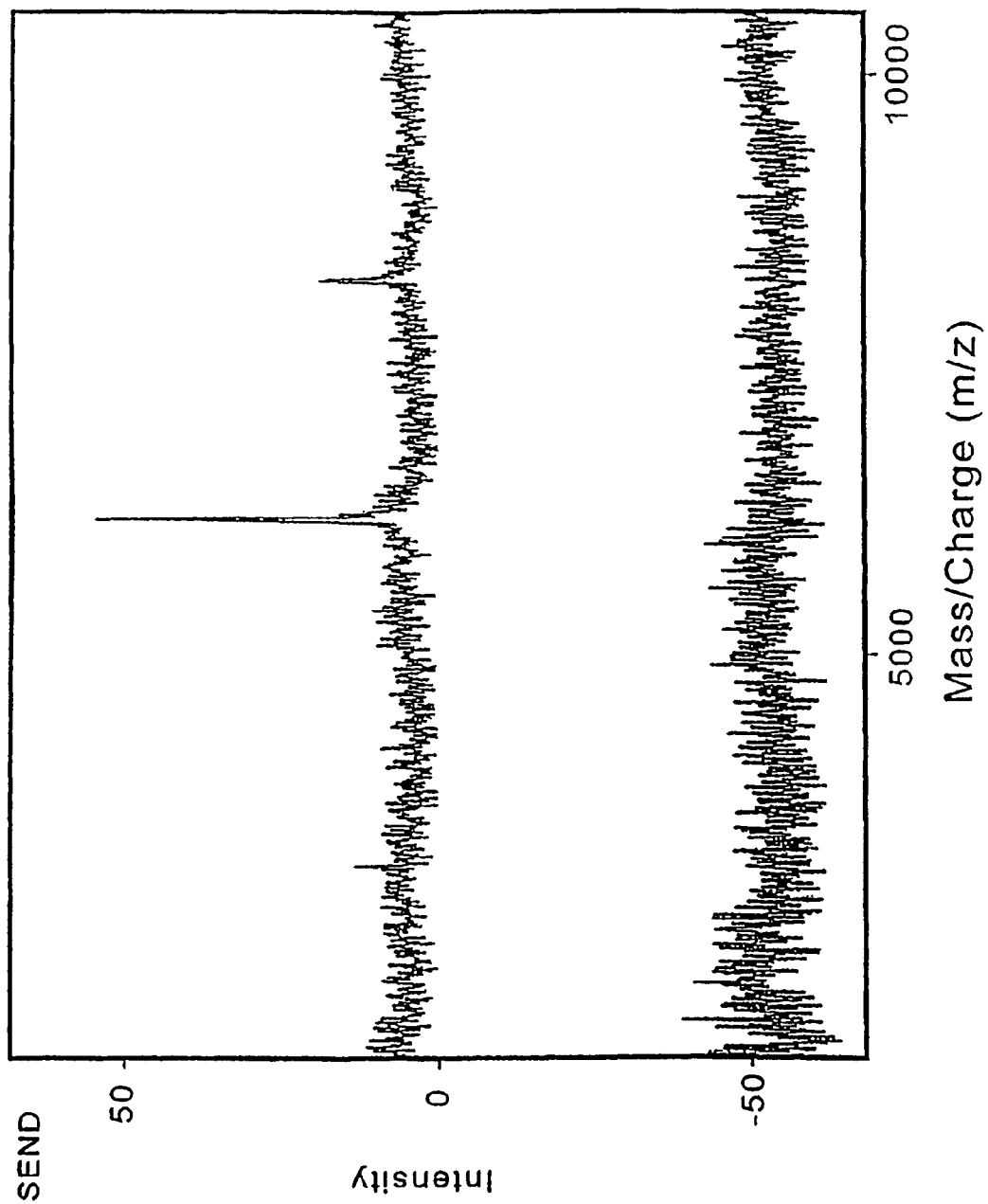

FIG. 22 (upper profile) shows the mass spectrum of peptide mixtures desorbed from surface bound cinnamyl bromide. FIG. 22 (lower profile) shows the mass spectrum of the same peptide mixtures with free cinnamyl bromide.

Figure 23:
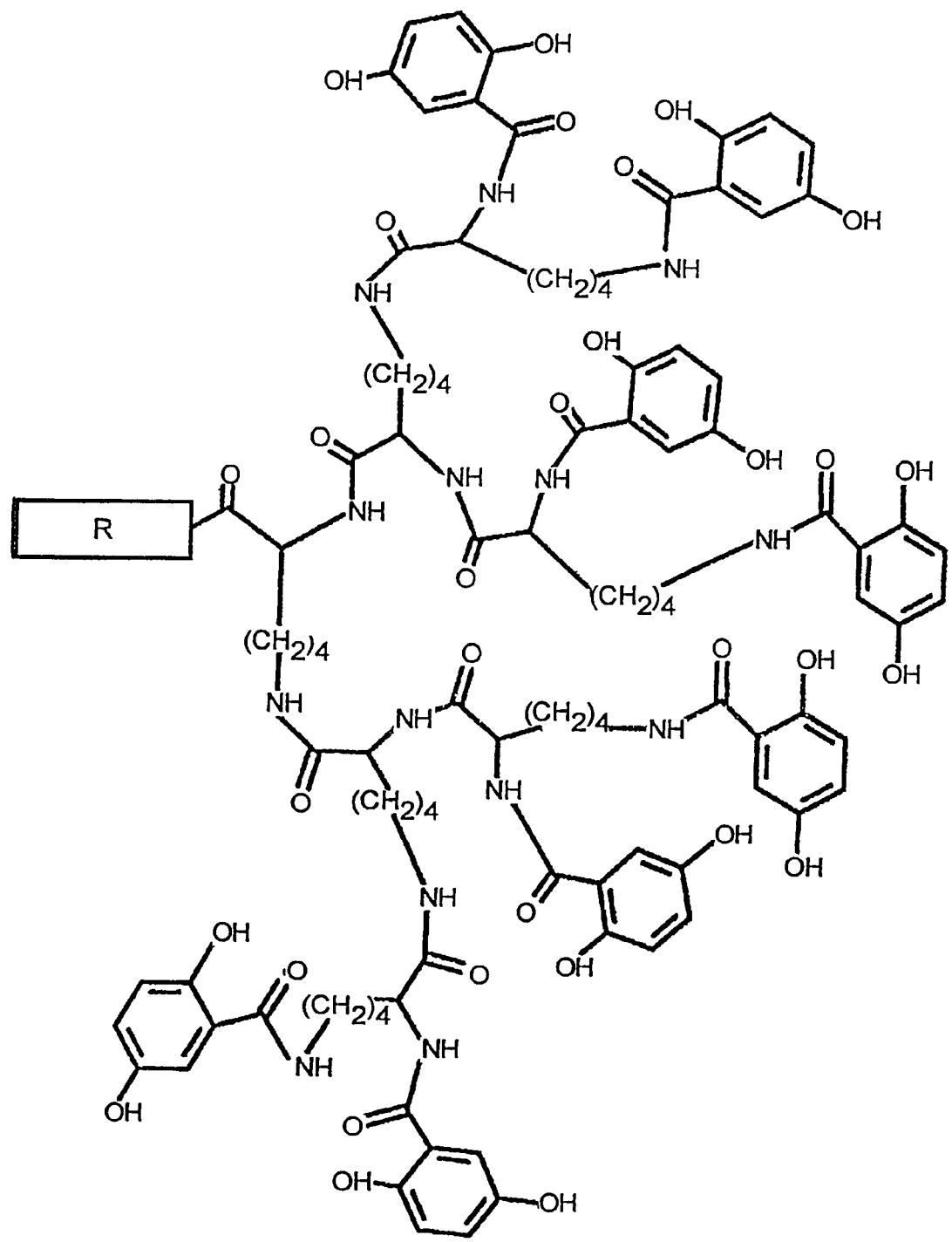

FIG. 23 shows the molecular structure of surface bound MAP-dihydroxybenzoic acid; R represents the surface plus cross-linker.

Figure 24:
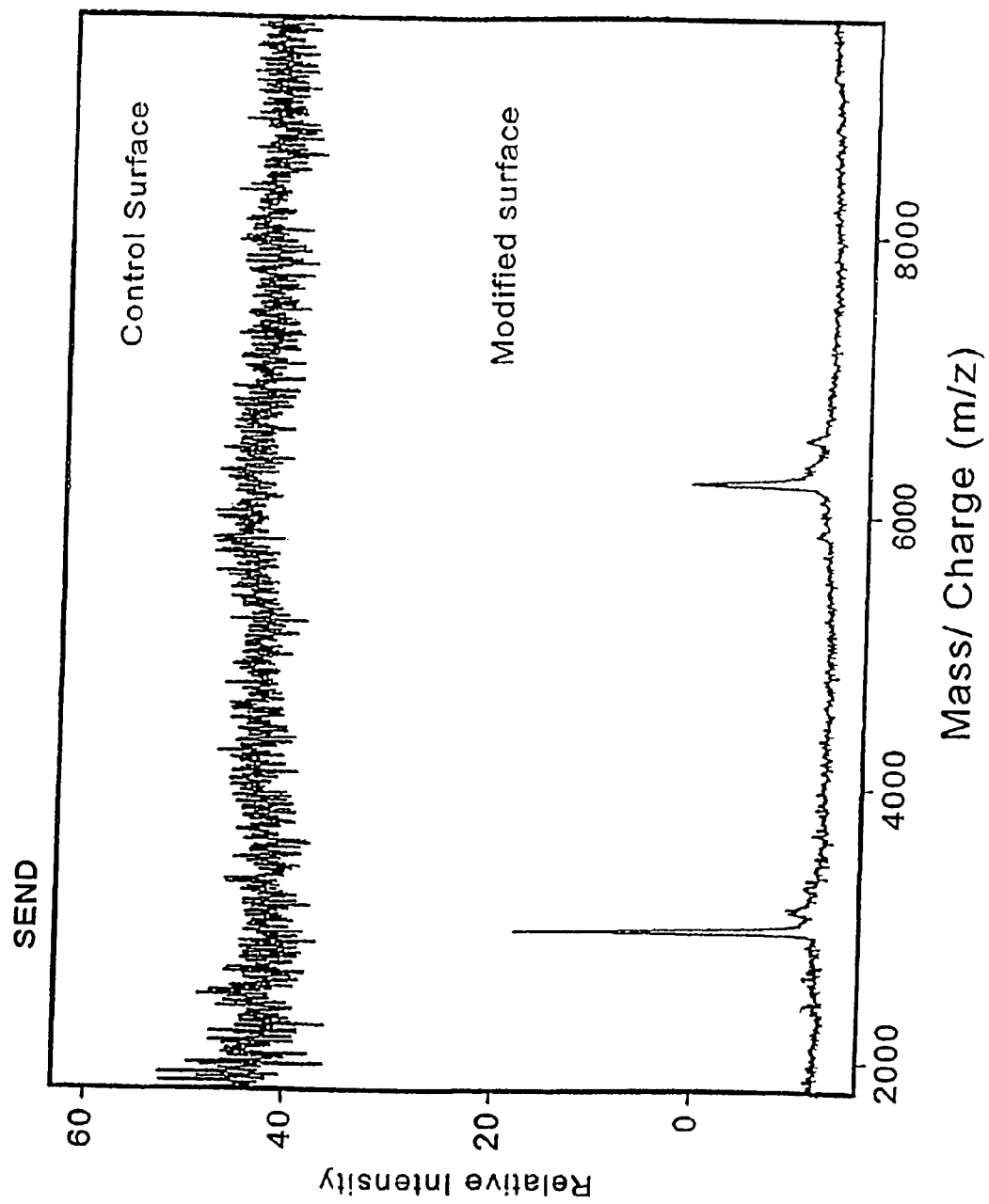

FIG. 24 (upper profile) shows the mass spectrum of peptide mixtures desorbed from surface bound MAP alone. FIG. 24 (lower profile) shows the mass spectrum of the same peptide mixtures desorbed from surface bound MAP-dihydroxybenzoic acid.

Figure 25A:
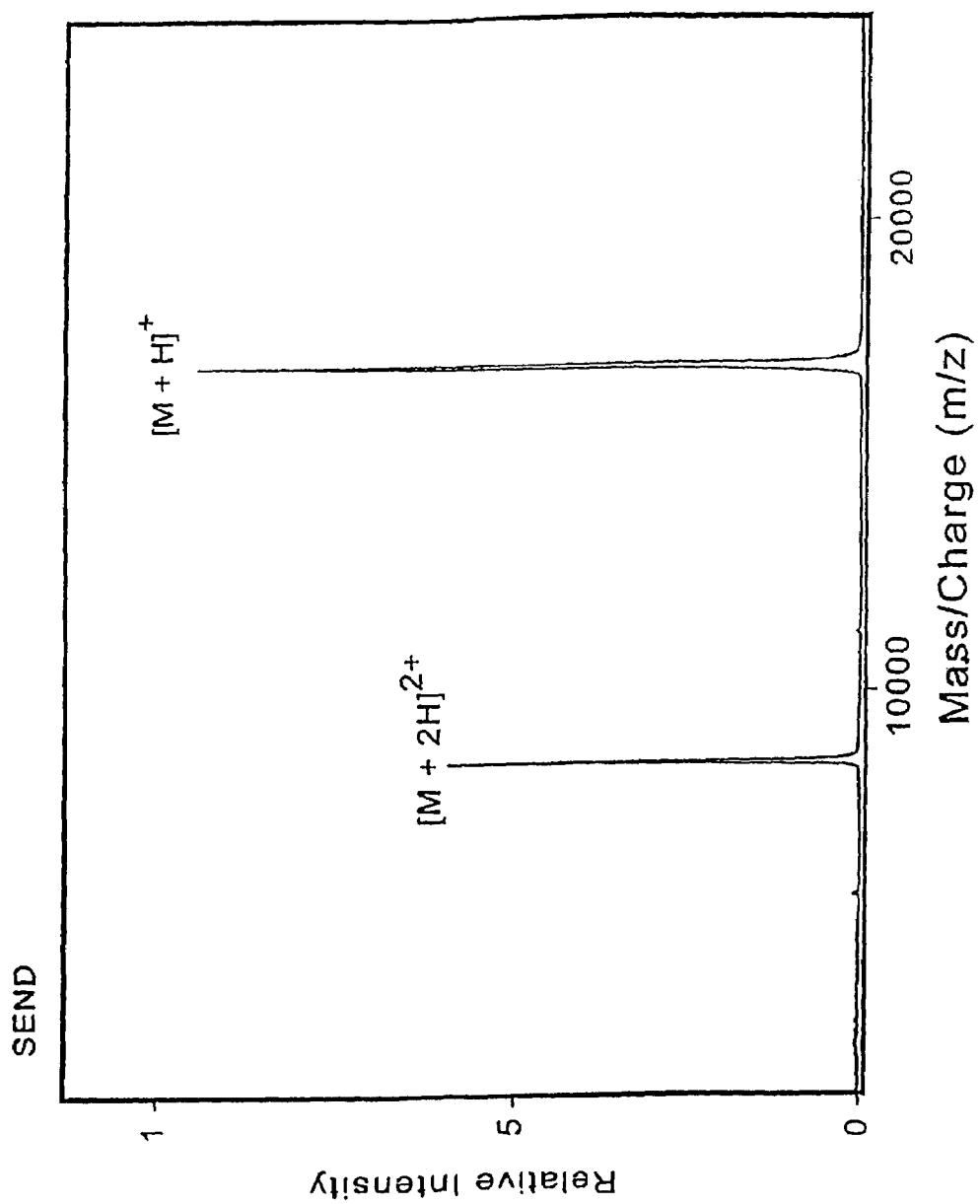
Figure 25B:
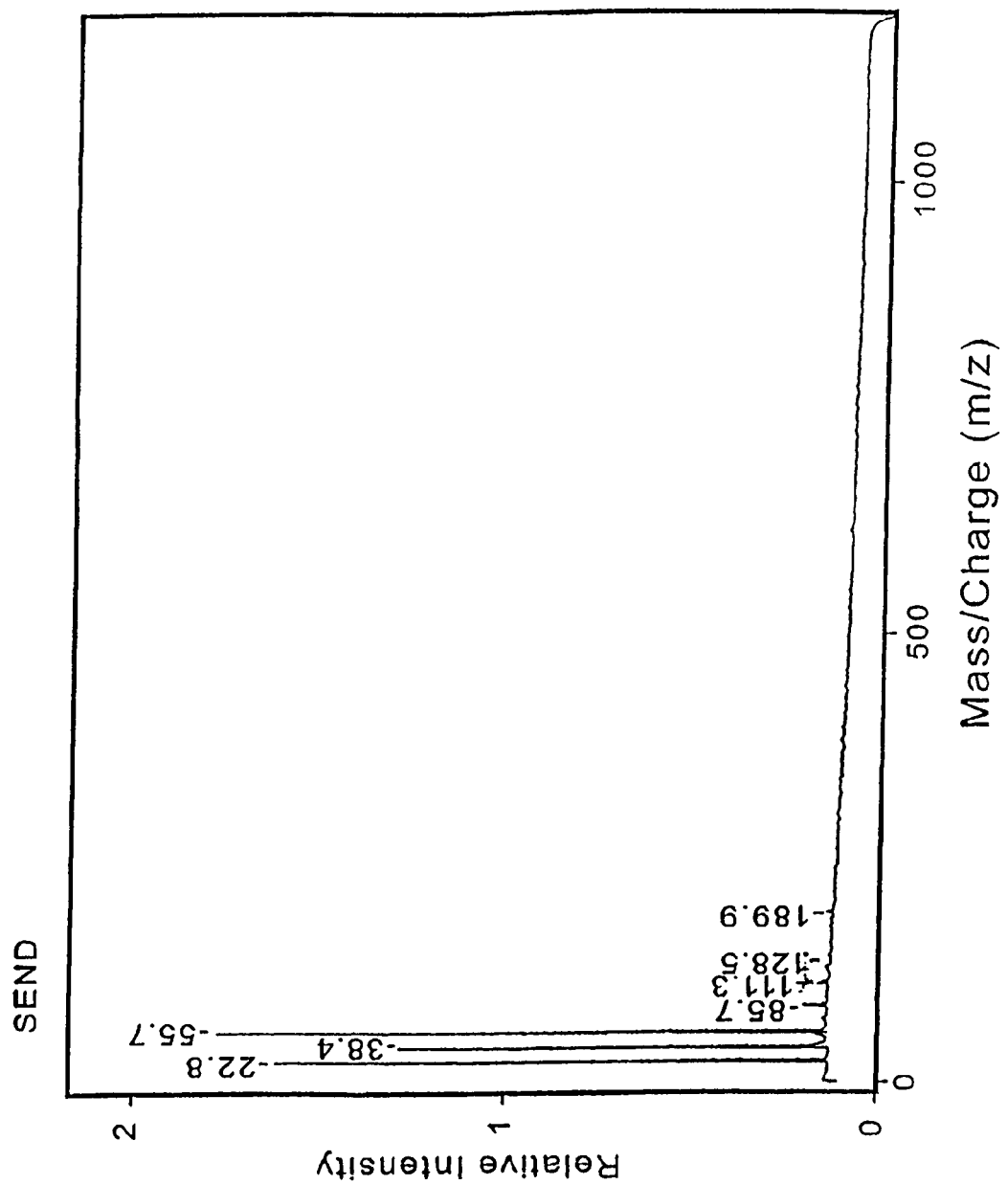

FIG. 25A shows the mass spectrum (1,200-50,000 m/z region) of myoglobin desorbed from surface bound .alpha.-cyano-4-hydroxycinnamic acid. FIG. 25B shows the same mass spectrum in the low mass region (0-1200 m/z).

Figure 26:
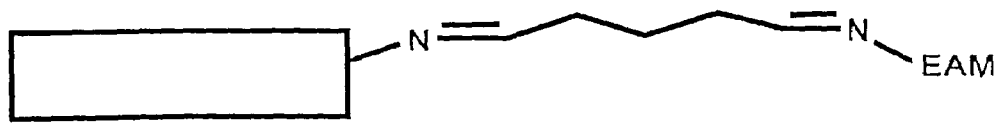

FIG. 26 shows the molecular structure of energy absorbing molecules bound to polyacrylamide or nylon or acrylic surface via glutaraldehyde activation.

Figure 27:
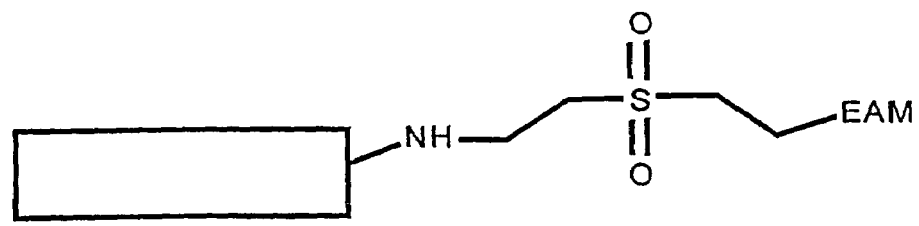

FIG. 27 shows the molecular structure of energy absorbing molecules bound to polyacrylamide or nylon or acrylic surface via divinyl sulfone activation.

Figure 28:
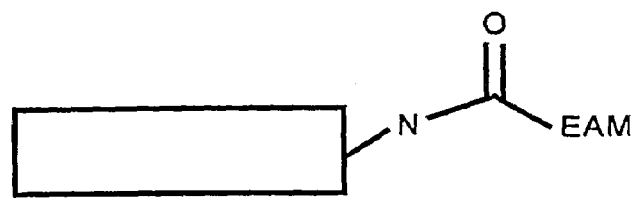

FIG. 28 shows the molecular structure of energy absorbing molecules bound to polyacrylamide or nylon or acrylic surface via dicyclohexylcarbodiimide activation.

Figure 29:
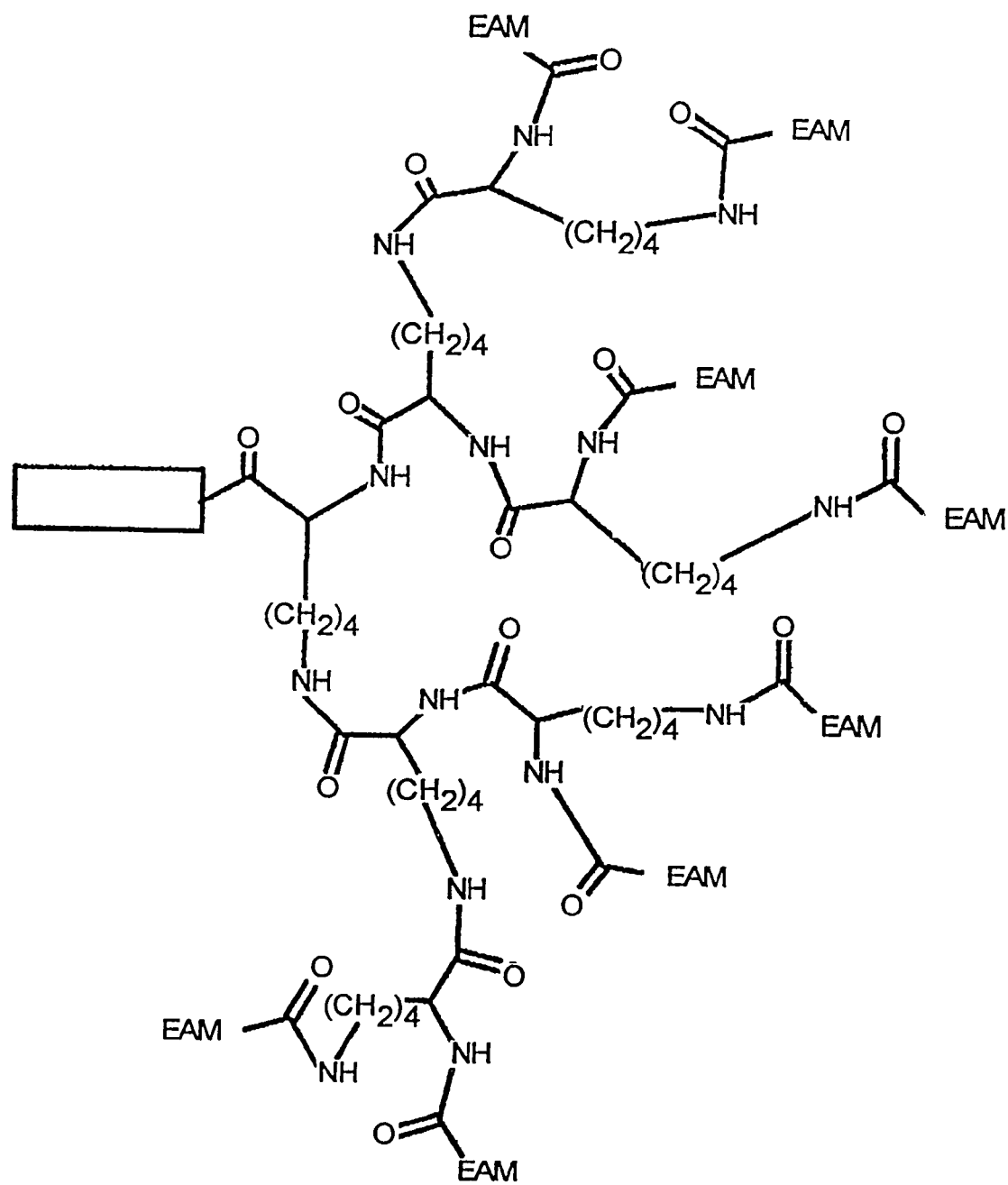

FIG. 29 shows the molecular structure of energy absorbing molecules bound to polyacrylamide or nylon or acrylic surface with multiple antigenic peptide via dicyclohexylcarbodiimide activation.

Figure 30:
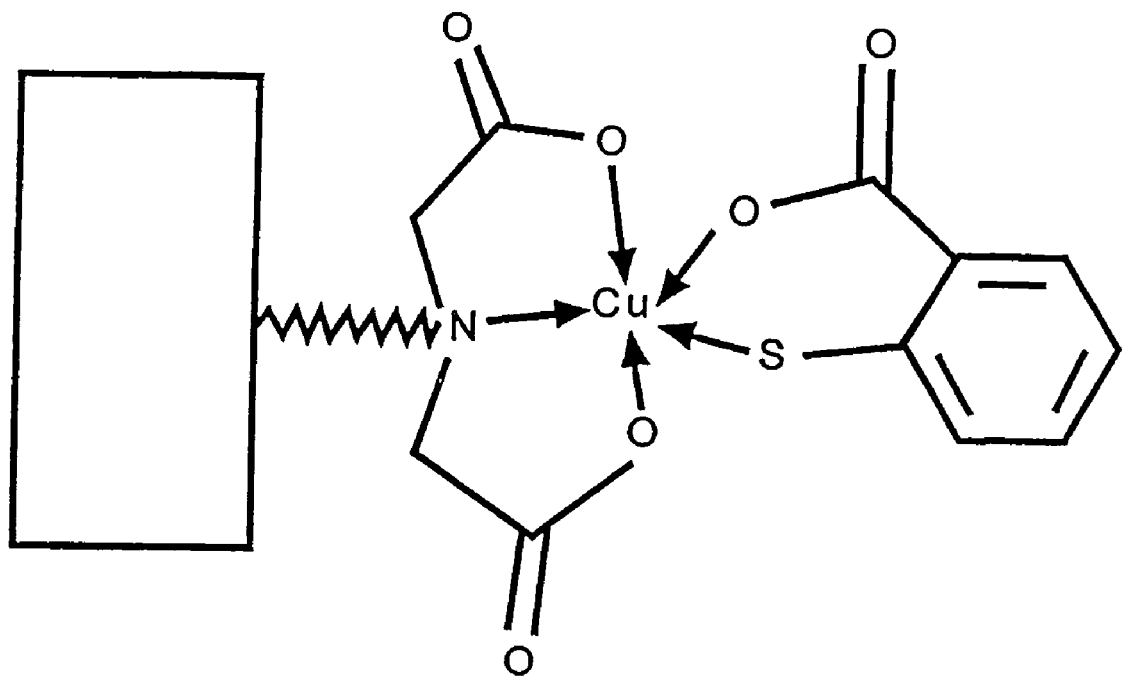

FIG. 30 shows the molecular structure of thiosalicylic acid bound to iminodiacetate (IDA)-Cu(II) surface.

Figure 31:
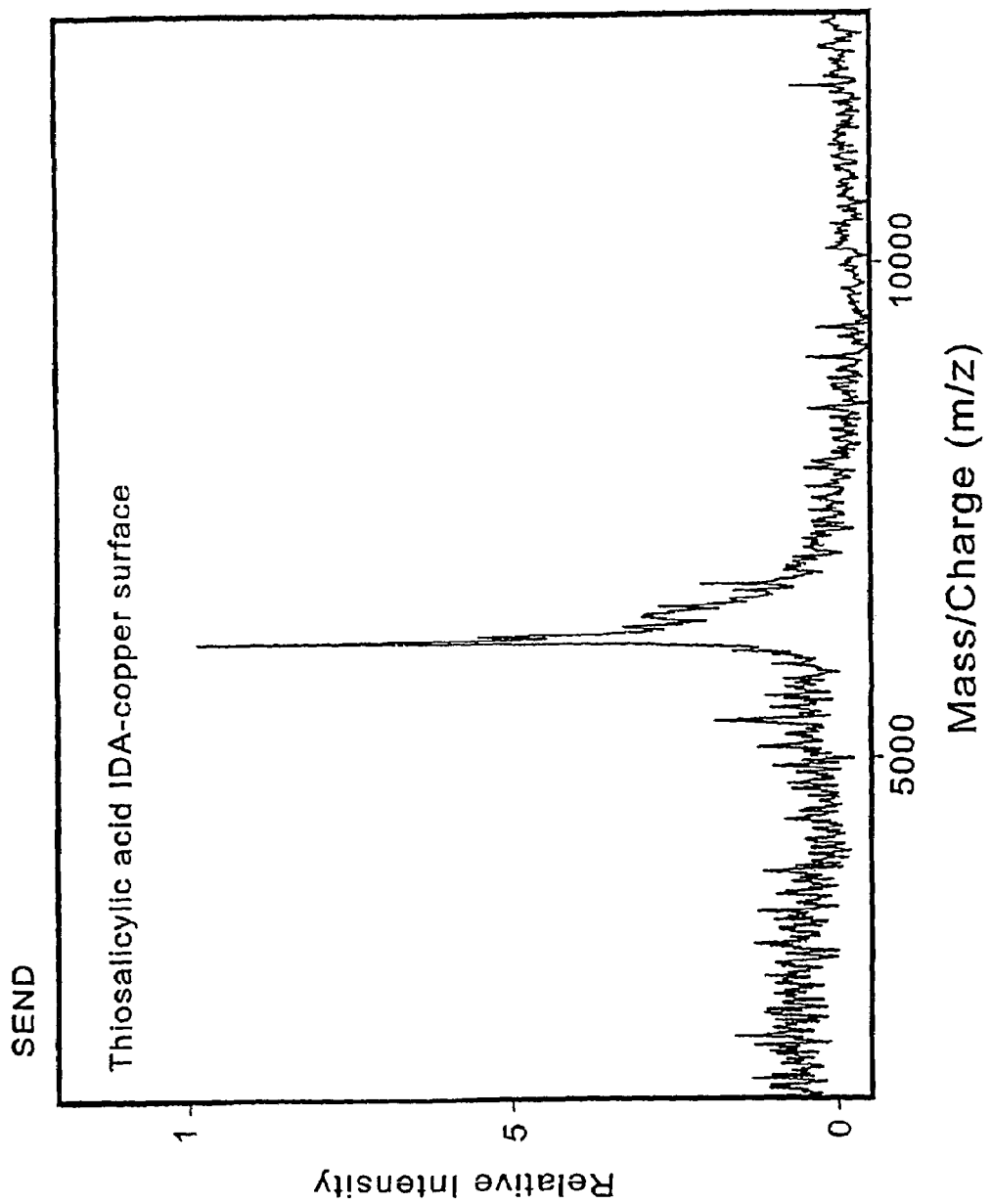

FIG. 31 shows the mass spectrum of human estrogen receptor dimerization domain desorbed from thiosalicylic acid-IDA-Cu(II) surface.

Figure 32:
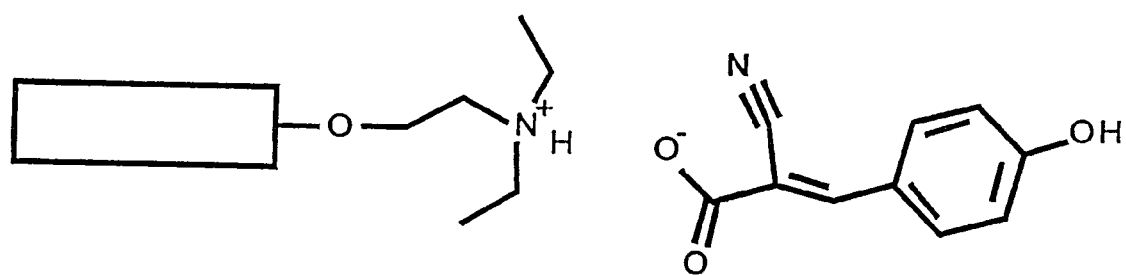

FIG. 32 shows the molecular structure of .alpha.-cyano-4-hydroxycinnamnic acid bound to DEAE surface.

Figure 33A:
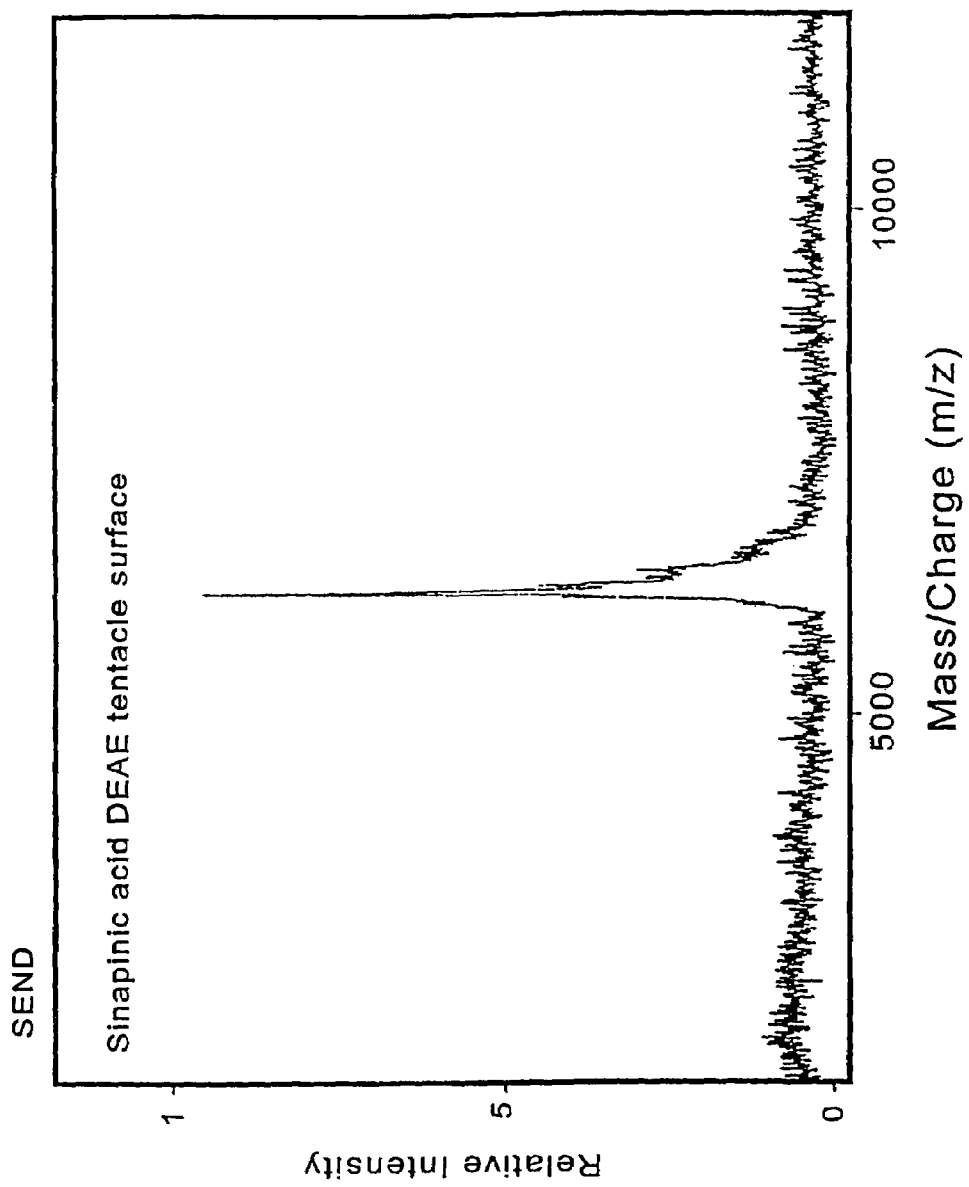
Figure 33B:
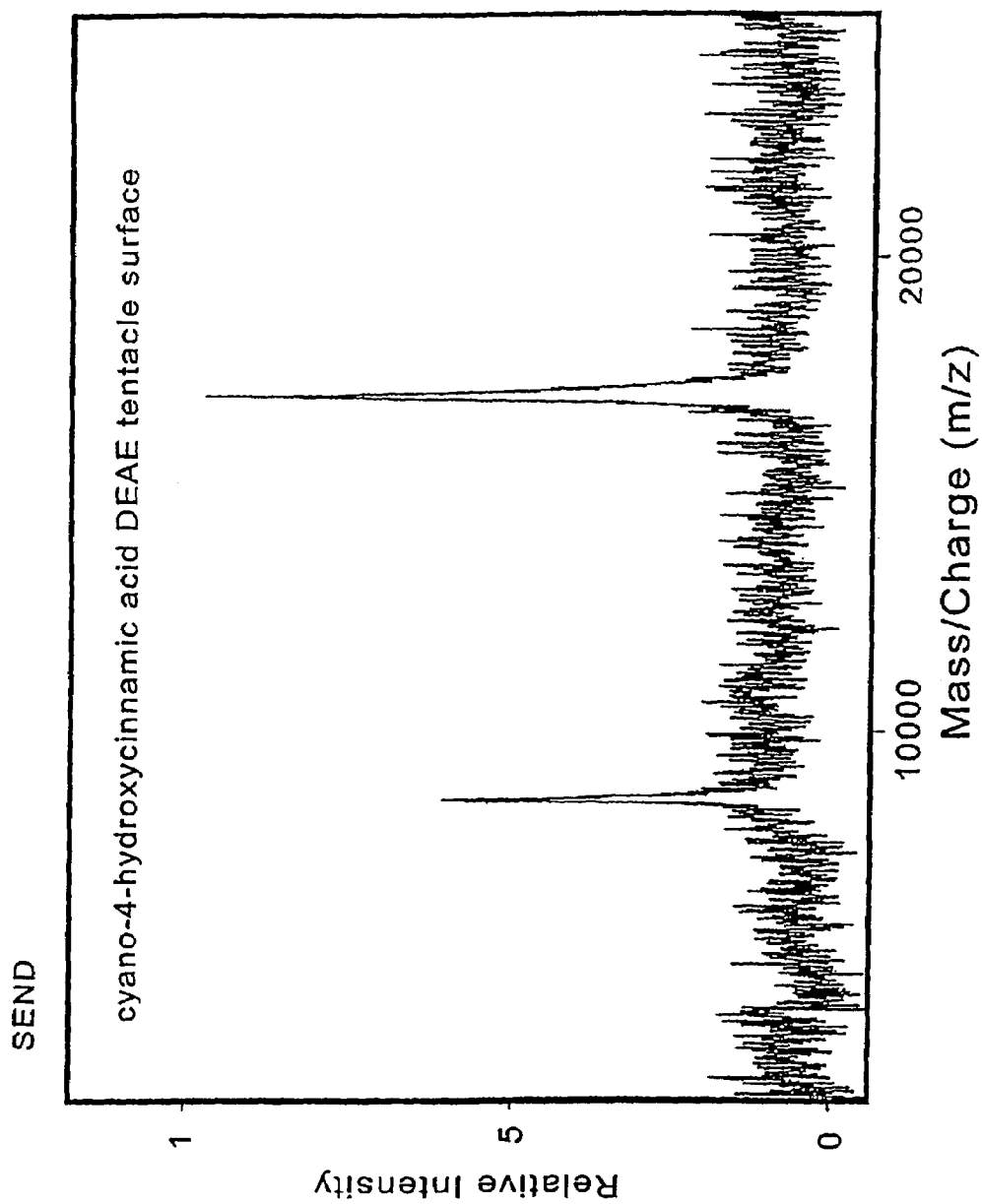

FIG. 33A shows the mass spectrum of human estrogen receptor dimerization domain desorbed from sinapinic acid-DEAE surface. FIG. 33B shows the mass spectrum of myoglobin desorbed from .alpha.-cyano-4-hydroxycinnamic acid DEAE surface.

Figure 34:
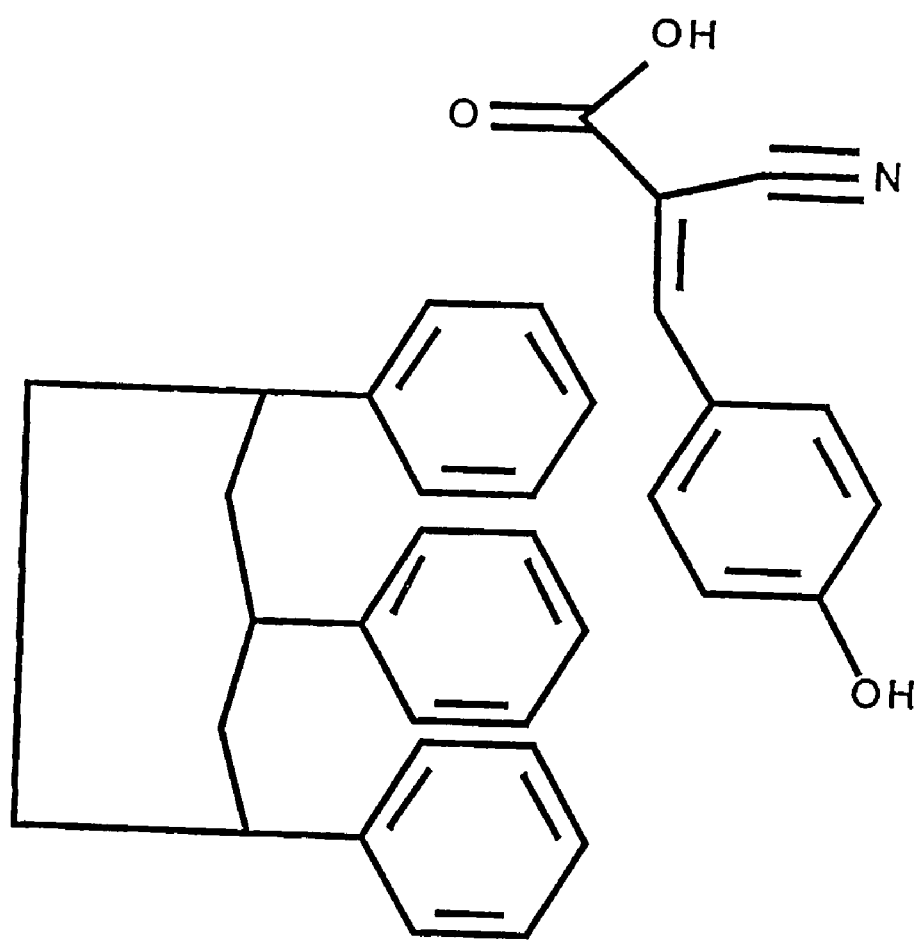

FIG. 34 shows the molecular structure of α-cyano-4hydroxycinnamic acid bound to polystyrene surface.

SEPAR

Figure 35:
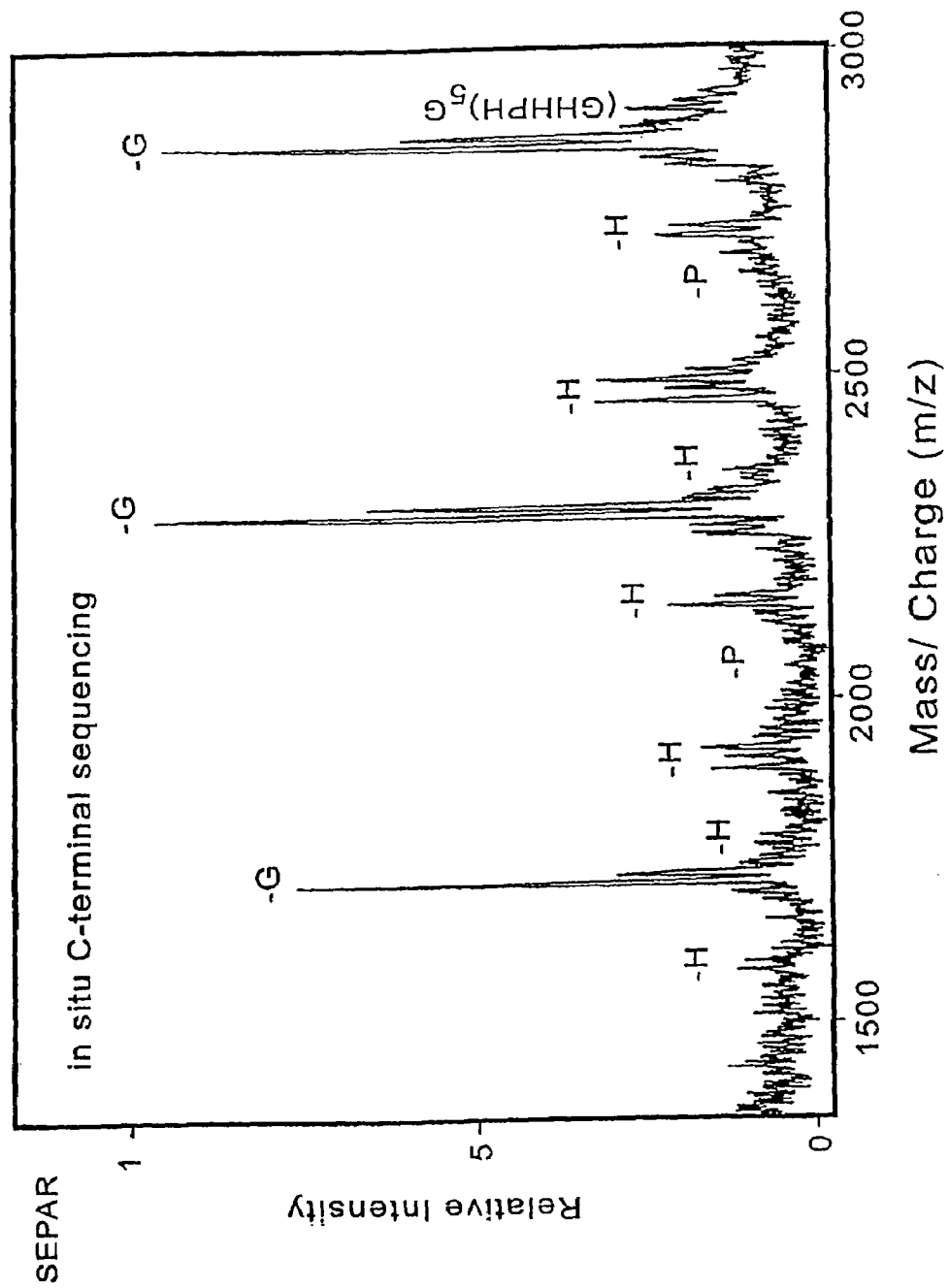

FIG. 35 shows the C-terminal sequence analysis of surface immobilized via photolytic bond histidine rich glycoprotein metal binding domain.

DETAILED DESCRIPTION OF THE INVENTION

It will be apparent to one skilled in the art that various substitutions and modifications may be made to the invention disclosed herein without departing from the scope and the spirit of the invention.

The development of new MS probe element compositions with surfaces that allow the probe element to actively participate in the capture and docking of specific analytes has recently defined several new opportunities in the area now being described as Affinity Mass Spectrometry (AMS). In brief, several types of new MS probe elements have been designed (Hutchens and Yip, *Rapid Commun Mass Spectrom*, 7:576-580 (1993)) with Surfaces Enhanced for Affinity Capture (SEAC). To Date, SEAC probe elements have been used successfully to retrieve and tether different classes of biopolymers, particularly proteins, by exploiting what is known about protein surface structures and biospecific molecular recognition.

Progress in structural biology continues to be limited by the inability to obtain biopolymer sequence information at an acceptable rate or level of sensitivity. By utilizing the methods and apparatus of the present invention, it has been demonstrated that AMS provides an opportunity to relieve this limitation. Because the immobilized affinity capture devices on the MS probe element surface (i.e., SEAC) determines the location and affinity (specificity) of the analyte for the probe surface, the subsequent analytical AMS process is much more efficient for several reasons. First, the location of analyte on the probe element surface is predetermined. Thus, the subsequent desorption is no longer dependent on a random search of the probe surface matrix field with the incident laser beam. Second, analyte detection sensitivity (and dynamic range) is increased because molecular ionization suppression effects often observed with complex mixtures are eliminated. Third, the tethered analyte that is not actually consumed by the initial laser-induced desorption process remains available for subsequent analyses. If exogenous matrix was used to promote analyte desorption, it is removed, in most cases, without loss of the tethered analyte. The remaining analyte can then be chemically and/or enzymatically modified directly in situ (i.e., while still on the probe element). When analyzed again by MS to determine differences in mass, specific structural details are revealed. The entire process of analysis/modification can be repeated many times to derive structural information while consuming only very small quantities of analyte (sometimes only a few femtomoles or less). The demonstrations of protein structure analysis based on AMS have to fate included both N- and C-terminal sequence analyses and verification of several types of sequence-specific posttranslational modifications including phosphorylation and dephosphorylation, glycosylation, cysteine residue reactivity, site-specific chemical modifications (e.g., Histidine residues), and ligand binding.

Beyond biopolymer sequence determinations and the solution of individual biopolymer structures, is the ability to understand the structural determinants of functional supramolecular assemblies. The opportunity to investigate the structural determinants of higher order (e.g., quaternary) structures is also presented by AMS. It has been demonstrated by using the present invention that noncovalent molecular recognition events, some not readily observed by more traditional bioanalytical procedures (often requiring disruption of equilibrium and structure dissociating conditions), are investigated directly by the evaluation of molecular associations (i.e., recognition) with macromolecular analytes that have been tethered, directly or indirectly, to the probe element surface.

As used herein, "analyte" refers to any atom and/or molecule; including their complexes and fragment ions. In the case of biological macromolecules, including but not limited to: protein, peptides, DNA, RNA, carbohydrates, steroids, and lipids. Note that most important biomolecules under investigation for their involvement in the structure or regulation of life processes are quite large (typically several thousand times larger than $H_2O$).

As used herein, the term "molecular ions" refers to molecules in the charged or ionized state, typically by the addition or loss of one or more protons ($H^+$).

As used herein, the term "molecular fragmentation" or "fragment ions" refers to breakdown products of analyte molecules caused, for example, during laser-induced desorption (especially in the absence of added matrix).

As used herein, the term "solid phase" refers to the condition of being in the solid state, for example, on the probe element surface.

As used herein, "gas" or "vapor phase" refers to molecules in the gaseous state (i.e., in vacuo for mass spectrometry).

As used herein, the term "analyte desorption/ionization" refers to the transition of analytes from the solid phase to the gas phase as ions. Note that the successful desorption/ionization of large, intact molecular ions by laser desorption is relatively recent (circa 1988)—the big breakthrough was the chance discovery of an appropriate matrix (nicotinic acid).

As used herein, the term "gas phase molecular ions" refers to those ions that enter into the gas phase. Note that large molecular mass ions such as proteins (typical mass=60,000 to 70,000 times the mass of a single proton) are typically not volatile (i.e., they do not normally enter into the gas or vapor phase). However, in the procedure of the present invention, large molecular mass ions such as proteins do enter the gas or vapor phase.

As used herein in the case of MALDI, the term "matrix" refers to any one of several small, acidic, light absorbing chemicals (e.g., nicotinic or sinapinic acid) that is mixed in solution with the analyte in such a manner so that, upon drying on the probe element, the crystalline matrix-embedded analyte molecules are successfully desorbed (by laser irradiation) and ionized from the solid phase (crystals) into the gaseous or vapor phase and accelerated as intact molecular ions. For the MALDI process to be successful, analyte is mixed with a freshly prepared solution of the chemical matrix (e.g., 10,000:1 matrix:analyte) and placed on the inert probe element surface to air dry just before the mass spectrometric analysis. The large fold molar excess of matrix, present at concentrations near saturation, facilitates crystal formation and entrapment of analyte.

As used herein, "energy absorbing molecules (EAM)" refers to any one of several small, light absorbing chemicals that, when presented on the surface of a probe element (as in the case of SEND), facilitate the neat desorption of molecules from the solid phase (i.e., surface) into the gaseous or vapor phase for subsequent acceleration as intact molecular ions. The term EAM is preferred, especially in reference to SEND. Note that analyte desorption by the SEND process is defined as a surface-dependent process (i.e., neat analyte is placed on a surface composed of bound EAM). In contrast, MALDI is presently thought to facilitate analyte desorption by a volcanic eruption-type process that "throws" the entire surface into the gas phase. Furthermore, note that some EAM when used as free chemicals to embed analyte molecules as described for the MALDI process will not work (i.e., they do not promote molecular desorption, thus they are not suitable matrix molecules).

As used herein, "probe element" or "sample presenting device" refers to an element having the following properties: it is inert (for example, typically stainless steel) and active (probe elements with surfaces enhanced to contain EAM and/or molecular capture devices).

As used herein, "MALDI" refers to Matrix-Assisted Laser Desorption/Ionization.

As used herein, "TOF" stands for Time-of-Flight.

As used herein, "MS" refers to Mass Spectrometry.

As used herein "MALDI-TOF MS" refers to Matrix-assisted laser desorption/ionization time-of-flight mass spectrometry.

As used herein, "ESI" is an abbreviation for Electrospray ionization.

As used herein, "chemical bonds" is used simply as an attempt to distinguish a rational, deliberate, and knowledgeable manipulation of known classes of chemical interactions from the poorly defined kind of general adherence observed when one chemical substance (e.g., matrix) is placed on another substance (e.g., an inert probe element surface). Types of defined chemical bonds include electrostatic or ionic (+/−) bonds (e.g., between a positively and negatively charged groups on a protein surface), covalent bonds (very strong or "permanent" bonds resulting from true electron sharing), coordinate covalent bonds (e.g., between electron donor groups in proteins and transition metal ions such as copper or iron), and hydrophobic interactions (such as between two noncharged groups).

As used herein, "electron donor groups" refers to the case of biochemistry, where atoms in biomolecules (e.g., N, S, O) "donate" or share electrons with electron poor groups (e.g., Cu ions and other transition metal ions).

The present invention uses a general category of probe elements (i.e., sample presenting means) with Surfaces Enhanced for Laser Desorption/Ionization (SELDI), within which there are three (3) separate subcategories. Surfaces Enhanced for Neat Desorption (SEND) where the probe element surfaces (i.e., sample presenting means) are designed to contain Energy Absorbing Molecules (EAM) instead of "matrix" to facilitate desorption/ionizations of analytes added directly (neat) to the surface. Note that this category 1 (SEND) is used alone or in combination with Surfaces Enhanced for Affinity Capture (SEAC) (category 2), where the probe element surfaces (i.e., sample presenting means) are designed to contain chemically defined and/or biologically defined affinity capture devices to facilitate either the specific or nonspecific attachment or adsorption (so-called docking or tethering) of analytes to the probe surface, by a variety of mechanisms (mostly noncovalent). Note that category 2 (SEAC) is used with added matrix or it is used in combination with category 1 (SEND) without added matrix. Thus, the combination of SEND and SEAC actually represents a distinctive category.

Category 3 involves Surfaces Enhanced for Photolabile Attachment and Release (SEPAR) where the probe element surfaces (i.e., sample presenting means) are designed/modified to contain one or more types of chemically defined crosslinking molecules to serve as covalent docking devices. These Photolabile Attachment Molecules (PAM) are bivalent or multivalent in character, that is, one side is first reacted so as to permanently attach the PAM to the probe element surface of the sample presenting means, then the other reactive side(s) of the PAM is ready to be reacted with the analyte when the analyte makes contact with the PAM-derivatized probe surface. Such surfaces (i.e., sample presenting means) allow for very strong (i.e., stable, covalent) analyte attachment or adsorption (i.e., docking or tethering) processes that are covalent but reversible upon irradiation (i.e., photolabile). Such surfaces represent platforms for the laser-dependent desorption of analytes that are to be chemically and/or enzymatically modified in situ (i.e., directly on the probe tip) for the purpose of structure elucidation. Only those analytes on the probe surface that are actually irradiated (small percentage of total) is desorbed. The remainder of the tethered analytes remain covalently bound and is modified without loss due to some inadvertent uncoupling from the surface. Note that the SEPAR category (category 3) is characterized by analyte attachment processes that are reversible upon exposure to light. However, the light-dependant reversal of the analyte surface attachment bond(s) does not necessarily enable analyte desorption into the gas phase per se. In other words, the molecules responsible for the photolabile attachment of the analytes to the probe surface are not necessarily the same as the Energy Absorbing Molecules (EAM) described for SEND. But here is an important exception: The present invention includes some hybrid EAM/PAM chemicals that have dual functionality with respect to SEND and SEPAR. That is, some EAM molecules presently used for SEND can be modified to act as mediators of both the SEND and SEPAR processes. Similarly, some hybrid affinity capture/PAM chemicals that have dual functionality with respect to SEAC and SEPAR are provided. The present invention uses some affinity capture devices, particularly those that are biologically defined, that are modified to act as mediators of both the SEAC and SEPAR processes.

The invention herein presents, a sample presenting means (i.e., probe element surface) with surface-associated (or surface-bound) molecules to promote the attachment (tethering or anchoring) and subsequent detachment of tethered analyte molecules in a light-dependent manner, wherein the said surface molecule(s) are selected from the group consisting of photoactive (photolabile) molecules that participate in the binding (docking, tethering, or crosslinking) of the analyte molecules to the sample presenting means (by covalent attachment mechanisms or otherwise). Further, a sample presenting means (composed of one or more of the suitable probe element materials described in previous claims), wherein analyte(s) are bound to the surface said sample presenting means by one or more photolabile bonds so that incident pulse(s) of light (e.g., from one or more lasers) is used to break the photolabile bond(s) tethering the analyte(s) to the probe element surface in a manner that is consistent with the subsequent desorption of the analyte from the stationary (solid) phase surface of the probe into the gas (vapor) phase is also presented.

The chemical specificity(ies) determining the type and number of said photolabile molecule attachment points between the SEPAR sample presenting means (i.e., probe element surface) and the analyte (e.g., protein) may involve any one or more of a number of different residues or chemical structures in the analyte (e.g., His, Lys, Arg, Tyr, Phe, and Cys residues in the case of proteins and peptides). In other words, in the case of proteins and peptides, the SEPAR sample presenting means may include probe surfaces modified with several different types of photolabile attachment molecules to secure the analyte(s) with a plurality of different types of attachment points.

The wavelength of light or light intensity (or incident angle) required to break the photolabile attachment(s) between the analyte and the probe element surface may be the same or different from the wavelength of light or light intensity (or incident angle) required to promote the desorption of the analyte from the stationary phase into the gas or vapor phase.

The photolabile attachment of the analyte(s) to the probe element surface (i.e., sample presenting means), particularly biopolymers such as peptides, proteins, ribonucleic acid (RNA), deoxyribonucleic acids (DNA), and carbohydrates (CHO), may involve multiple points of attachment between the probe surface and the analyte macromolecule. Once the biopolymer is attached via multiple points of attachment, different points in the backbone of the biopolymer may be deliberately cut or fragmented by chemical and/or enzymatic means so that many of the resulting fragments are now separate and distinct analytes, each one still attached (tethered) to the probe surface by one or more photolabile bonds, to be desorbed into the gas phase in parallel for simultaneous mass analyses with a time-of-flight mass analyzer.

This process enables biopolymer (protein, peptides, RNA, DNA, carbohydrate) sequence determinations to be made.

As used herein "affinity" refers to physical and/or chemical attraction between two molecules. Typically used in nature for purposes of structure or regulation of bioactivity (i.e., information transfer). Usually the affinity of one biomolecule for another is quite specific. Used in the present case to describe principle by which molecular analytes of interest are captured. In the case of SEAC, chemicals or biomolecules with a characteristic affinity for the analyte(s) of interest are tethered (bound) to the surface of the probe element to actively "seek" out and selectively bind the desired analyte.

As used herein, "molecular recognition" refers to the interaction event between two molecules with a natural affinity for one another.

As used herein, "molecular capture" refers to the use of tethered biomolecules to attract and bind (capture) other biomolecules for which a specific affinity relationship exists.

As used herein, "passive adsorption" refers to the act of simply placing the analyte (e.g., with matrix).

As used herein, "active docking" refers to the deliberate capture of analyte molecules on the surface of an active probe element as in the case of SEAC.

As referred to herein "stationary phase" means the same as solid phase. In the present context either the probe element surface itself or one of the "external" particulate SEND or SEAC devices used in conjunction with an inert probe element surface.

As used herein, "active surface area" refers to that area of the surface thought or known to participate in the desired reaction or event (e.g., EAM attachment or affinity capture). The active surface area may be significantly less than the total surface area (due to physical effects such as steric hinderance, some of the total area may not be available or useful).

As used herein, "ligand" refers to a typically relatively small molecule (bait) that binds to a large biomolecule (fish). In the present case, ligands are attached (chemically bound) through a linker arm (fishing line) to the probe element surface. This process allows the biomolecular capture event to be localized on the surface (stationary or solid phase).

As used herein, "affinity reagent" refers to an analyte capture device, viz., the class of molecules (both man made, unnatural, natural and biological) and/or compounds which have the ability of being retained on the presenting surface (by covalent bonding, chemical absorption, etc.) while retaining the ability of recognition and bonding to an analyte.

As used herein, "desorption" refers to the departure of analyte from the surface and/or the entry of the analyte into a gaseous phase.

As used herein, "ionization" refers to the process of creating or retaining on an analyte an electrical charge equal to plus or minus one or more electron units.

As used herein, "adduct" refers to the appearance of an additional mass associated with the analyte and usually caused by the reaction of excess matrix (or matrix breakdown products) directly with the analyte.

As used herein, "adsorption"—the chemical bonding (covalent and/or noncovalent) of the energy-absorbing molecules, the affinity reagent (i.e., analyte capture device), and/or the analyte to the probe (presenting surface).

One embodiment of the present invention is an apparatus for measuring the mass of an analyte molecule of an analyte sample by means of mass spectrometry, said apparatus comprising: a spectrometer tube; vacuum means for applying a vacuum to the interior of said tube; electrical potential means within the tube for applying an accelerating electrical potential to desorbed analyte molecules from said analyte sample; sample presenting means removably insertable into said spectrometer tube, for presenting said analyte sample in association with surface associated molecule for promoting desorption and ionization of said analyte molecules, wherein said surface molecule is selected from the group consisting of energy absorbing molecule, affinity capture device, photolabile attachment molecule and combination thereof; an analyte sample deposited on said sample presenting means in association with said surface associated molecules; whereby at least a portion of said analyte molecules not consumed in said mass spectrometry analysis will remain accessible for subsequent chemical, biological or physical analytical procedures; laser beam means for producing a laser beam directed to said analyte sample for imparting sufficient energy to desorb and ionize a portion of said analyte molecules from said analyte sample; and detector means associated with said spectrometer tube for detecting the impact of accelerated ionized analyte molecules thereon.

Another embodiment of the present invention is a method in mass spectrometry to measure the mass of an analyte molecule, said method comprising the steps of: derivitizing a sample presenting surface on a probe tip face with an affinity capture device having means for binding with an analyte molecule; exposing said derivitized probe tip face to a source of said analyte molecule so as to bind said analyte molecule thereto; placing the derivitized probe tip with said analyte molecules bound thereto into one end of a time-of-flight mass spectrometer and applying a vacuum and an electric field to form an accelerating potential within the spectrometer; striking at least a portion of the analyte molecules bound to said derivitized probe tip face within the spectrometer with one or more laser pulses in order to desorb ions of said analyte molecules from said tip; detecting the mass of the ions by their time of flight within said mass spectrometer; and displaying such detected mass. In an preferred embodiment, this method further comprises applying a desorption/ionization assisting matrix material to said probe tip face in association with said affinity capture device. In a more preferred embodiment, the method according further comprises removing said probe tip from said mass spectrometer; performing a chemical or biological procedure on said portion of said analyte molecules not desorbed to alter the composition of said portion of said analyte molecules not desorbed; reinserting said probe tip with said altered analyte molecules thereon; and performing subsequent mass spectrometry analysis to determine the molecular weight of said altered analyte molecules.

In an additional embodiment, said affinity capture device is chemically bonded to said face of said probe tip, physically adhered to said face of said probe tip, adapted to chemically bond to said analyte molecules, or adapted to biologically adhere to said analyte molecules. In a further embodiment, said analyte molecules are biomolecules and said affinity reagent is adapted to selectively isolate said biomolecules from an undifferentiated biological sample. In a preferred embodiment, said matrix materials are in the weakly acidic to strongly basic pH range. In a more preferred embodiment, said matrix materials have a pH above 6.0. Further, an additional embodiment presents the face of said probe tip formed of an electrically insulating material.

An additional embodiment of the present invention is a method of measuring the mass of analyte molecules by means of laser desorption/ionization, time-of-flight mass spectrometry in which an energy absorbing material is used in conjunction with said analyte molecules for facilitating desorption and ionization of the analyte molecules, wherein the improvement comprises presenting the analyte molecules on or above the surface of the energy absorbing material, wherein at least a portion of the analyte molecules not desorbed in said mass spectrometry analysis remain chemically accessible for subsequent analytical procedures.

A further embodiment of the present invention is an apparatus for facilitating desorption and ionization of analyte molecules, said apparatus comprising: a sample presenting surface; and surface associated molecules, wherein said surface associated molecules are selected from the group consisting of energy absorbing molecule, affinity capture device, photolabile attachment molecule and combination thereof, said surface associated molecules associated with said sample presenting surface and having means for binding with said analyte molecules.

In a preferred embodiment, said sample presenting surface comprises the surface of a probe tip for use in a time-of-flight mass spectrometry analyzer. In addition, the preferred embodiment presents an affinity capture device or photolabile attachment molecule that is chemically bonded to said sample presenting surface, physically adhered to said sample presenting surface, chemically bonded to said analyte molecules, or is adapted to biologically adhere to said analyte molecules. Further, the preferred embodiment presents analyte molecules are biomolecules and said affinity capture device or photolabile attachment molecule is adapted to selectively isolate said biomolecules from an undifferentiated biological sample.

In addition, the apparatus may have a matrix material deposited on said sample presenting surface in association with said affinity capture device or photolabile attachment molecule. In a more preferred embodiment, the matrix material is in the weakly acidic to strongly basic pH range. In a most preferred embodiment, the matrix material has a pH above 6.0. Additionally, a preferred embodiment includes a sample presenting surface formed of an electrically insulating material.

In an additional embodiment of the present invention, there is presented a method for capturing analyte molecules on a sample presenting surface and desorbing/ionizing said captured analyte molecules from said sample presenting surface for subsequent analysis, said method comprising: derivitizing said sample presenting surface with an affinity capture device or photolabile attachment molecule having means for binding with said analyte molecules; exposing said derivitized sample present surface to a sample containing said analyte molecules; capturing said analyte molecules on said derivitized sample presenting surface by means of said affinity capture device or photolabile attachment molecule; and exposing said analyte molecules, while bound to said derivitized sample presenting surface by means of said affinity capture device or photolabile attachment molecule, to an energy or light source to desorb at least a portion of said analyte molecules from said surface.

A further embodiment of the present invention is a method for preparing a surface for presenting analyte molecules for analysis, said method comprising: providing a substrate on said surface for supporting said analyte; derivitizing said substrate with an affinity capture device or photolabile attachment molecule having means for selectively bonding with said analyte; and a means for detecting said analyte molecules bonded with said affinity capture device or photolabile attachment molecule. In a preferred embodiment, there is provided the additional step of applying a detection material to said surface. In a more preferred embodiment, such detection material comprises a fluorescing species, an enzymatic species, a radioactive species, or a light-emitting species.

In an additional preferred embodiment, the step of depositing a desorption/ionization assisting material to said sample presenting surface in association with said affinity capture device or photolabile attachment molecule is included. In a further preferred embodiment, the energy source comprises a laser. In another preferred embodiment, an affinity capture device is used and said energy source comprises an ion source. Further, a preferred embodiment may include a portion of said analyte molecules remaining bound to said sample presenting surface after exposure to said energy source. In a more preferred embodiment, the additional steps of converting at least a portion of the analyte molecules remaining bound on said derivitized sample presenting surface to modified analyte molecules by a chemical, biological or physical reaction, wherein said analyte molecules remain bound to said derivitized sample presenting surface by means of said affinity capture device or photolabile attachment molecule; and exposing said modified analyte molecules to an energy source so as to desorb at least a portion of said modified analyte molecules from said surface are included.

In an embodiment of the present invention, a sample probe for promoting desorption of intact analytes into the gas phase comprising: a sample presenting surface; and an energy absorbing molecule associated with said sample presenting surface, wherein said sample probe promotes desorption of an intact analyte molecule positioned on, above or between the energy absorbing molecules when said sample probe is impinged by an energy source is provided. In a more preferred embodiment, the energy absorbing molecule is selected from the group consisting of cinnamamide, cinnamyl bromide, 2,5-dihydroxybenzoic acid and α-cyano-4-hydroxycinnamic acid. Also in a preferred embodiment, one may utilize a sample presenting surface selected from the group consisting of glass, ceramics, teflon coated magnetic materials; organic polymers and native biopolymers.

In another embodiment of the present invention, there is provided a sample probe for promoting desorption of intact analytes into the gas phase comprising: a sample presenting surface; and an affinity capture device associated with said sample presenting surface; wherein, when said sample probe is impinged by an energy source, said sample probe promotes the transition of an intact analyte molecule into the gas phase. In a preferred embodiment, the affinity capture device is selected from the group consisting of metal ions, proteins, peptides, immunoglobulins, nucleic acids, carbohydrates, lectins, dyes, reducing agents and combination thereof. In another preferred embodiment, the sample presenting surface is selected from the group consisting of glass, ceramics, teflon coated magnetic materials; organic polymers and native biopolymers.

An additional embodiment presents a sample probe for desorption of intact analyte into the gas phase, comprising: a sample presentation surface; and a surface associated molecule wherein said surface associated molecule is a photolabile attachment molecule having at least two binding sites, wherein at least one site is bound to the sample presentation surface and at least one site is available to bind an analyte and wherein the analyte binding site is photolabile.

In another embodiment, there is provided a sample probe for promoting desorption of intact analytes into the gas phase comprising: a sample presentation surface; and either a mixture of at least two different molecules selected from the group consisting of an affinity capture device, an energy absorbing molecule and a photolabile attachment molecule associated with said sample presentation surface; wherein when an analyte is associated with said sample probe, said sample probe promotes the transition of the analyte into the gas phase when said sample probe is impinged by an energy source; or at least two different affinity capture devices associated with said sample presentation surface; wherein, when said sample probe is impinged by an energy source, said sample probe promotes the transition of an analyte molecule into the gas phase at different rates depending on the affinity capture device associated with said analyte molecule.

In a preferred embodiment, the analyte is selectively desorbed from the mixture after impingement by the energy source. In another preferred embodiment, the affinity devices are arranged in predetermined arrays. This can be accomplished by arranging the affinity adsorption "spots" (0.005 to 0.080 inch diameter) on the probe surface in a defined manner (400 to 1,000 spots could be placed on a surface about the size of a glass slide). In a more preferred embodiment, the arrays selectively absorb a plurality of different analytes.

In a more preferred embodiment, an apparatus of the present invention is used to quantitate an analyte, wherein the position and quantity of affinity capture devices determines the quantity of analyte absorbed. In another preferred embodiment, the binding may be selective or non-selective.

In an additional embodiment, a sample probe for promoting desorption of intact analyte into the gas phase, comprising: a sample presentation surface; and either a surface associated molecule, wherein said surface associated molecule can function both as an energy absorbing molecule and as an affinity capture device; or a surface associated molecule wherein said surface associated molecule is a photolabile attachment molecule having at least two binding sites, wherein at least one site is bound to the sample presentation surface and at least one site is available to bind an analyte and wherein the analyte binding site is photolabile.

A different embodiment of the present invention includes a method in mass spectrometry to measure the mass of an analyte molecule, said method comprising the steps of: derivitizing a sample presenting surface on a probe tip face with a photolabile attachment molecule (PAM), wherein said PAM has at least two binding sites, one binding site binds to the sample presenting surface and at least one binding site is available for binding with an analyte molecule; exposing said derivitized probe tip face to a source of said analyte molecule so as to bind said analyte molecule thereto; placing the derivitized probe tip with said analyte molecules bound thereto into one end of a time-of-flight mass spectrometer and applying a vacuum and an electric field to form an accelerating potential within the spectrometer; striking at least a portion of the analyte molecules bound to said derivitized probe tip face within the spectrometer with one or more laser pulses in order to desorb ions of said analyte molecules from said tip; detecting the mass of the ions by their time of flight within said mass spectrometer; and displaying such detected mass. In a preferred embodiment, the step of applying a desorption/ionization assisting matrix material to said probe tip face in association with said PAM is included. In a more preferred embodiment, an additional steps of removing said probe tip from said mass spectrometer; performing a chemical, biological or physical procedure on said portion of said analyte molecules not desorbed to alter the composition of said portion of said analyte molecules not desorbed; reinserting said probe tip with said altered analyte molecules thereon; and performing subsequent mass spectrometry analysis to determine the molecular weight of said altered analyte molecules are included. A preferred embodiment may also include PAM being chemically bonded to said face of said probe tip; PAM being chemically bonded to said analyte molecule, wherein said bond between the PAM and the analyte molecule is broken and the analyte molecule is released in a light dependent manner; or, where said analyte molecules are biomolecules, said PAM is adapted to selectively isolate said biomolecules from an undifferentiated biological sample. In another preferred embodiment, said matrix materials are in the weakly acidic to strongly basic pH range. In a more preferred embodiment, said matrix materials have a pH above 6.0. A preferred embodiment may also include the face of said probe tip being formed of an electrically insulating material.

A further embodiment presents a method of measuring the mass of analyte molecules by means of laser desorption/ionization, time-of-flight mass spectrometry in which a photolabile attachment molecule (PAM) is used in conjunction with said analyte molecules for facilitating desorption and ionization of the analyte molecules, the improvement comprising: presenting the analyte molecules on or above the surface of the PAM, wherein at least a portion of the analyte molecules not desorbed in said mass spectrometry analysis remain chemically accessible for subsequent analytical procedures.

Another embodiment of the present invention is a sample probe for promoting of differential desorption of intact analyte into the gas phase, comprising: a sample presentation surface; and at least two different photolabile attachment molecules associated with said sample presentation surface; wherein, when said sample probe is impinged by an energy source, said sample probe promotes the transition of an analyte molecule into the gas phase at different rates depending on the photolabile attachment molecule associated with said analyte molecule. In a preferred embodiment, the photolabile attachment molecules are arranged in predetermined arrays. In a more preferred embodiment, the arrays selectively absorb a plurality of different analytes.

An additional embodiment of the present invention includes a sample probe for promoting desorption of intact analytes into the gas phase comprising: a sample presenting surface; and a photolabile attachment molecule associated with said sample presenting surface; wherein, when said sample probe is impinged by an energy source, said sample probe promotes the transition of an intact analyte molecule into the gas phase. In a preferred embodiment, and analyte is quantitated, wherein the position and quantity of photolabile attachment molecule determines the quantity of analyte absorbed.

Another embodiment shows a method for biopolymer sequence determination comprising the steps of binding a biopolymer analyte to probe tip containing a sample presenting surface having a surface selected molecule selected from the group consisting of an energy absorbing molecule, an affinity capture device, a photolabile attachment molecule and a combination thereof; desorption of biopolymer analyte in mass spectrometry analysis, wherein at least a portion of said biopolymer is not desorbed from the probe tip; analyzing the results of the desorption modifying the biopolymer analyte still bound to the probe tip; and repeating the desorption, analyzing and modifying steps until the biopolymer is sequenced. A preferred embodiment presents the biopolymer selected from the group consisting of protein, RNA, DNA and carbohydrate.

The following specific examples describe specific embodiments of the present invention and its materials and methods, are illustrative of the invention and are not intended to limit the scope of the invention.

The examples of the present invention utilize a time-of-flight mass spectrometer with a high energy source, such as a laser beam, to vaporize the analyte from the surface of a probe tip. In the process, some of the molecules are ionized. The positively charged molecules are then accelerated through a short high voltage field and enter into a field-free flight tube. A sensitive detector positioned at the end of the flight tube gives a signal as each molecular ion strikes it. One skilled in the art recognizes that other modes of detection and ionization can also be used.

EXAMPLE 1

Energy Absorbing Molecules in Aqueous, Neutralized Form

Prior art matrix material used in matrix-assisted laser desorption time-of-flight mass spectrometry are strongly acidic. One of the present discoveries is that analytes is desorbed when mixed with neutralized energy absorbing molecules dissolved in entirely aqueous solvents. By suitable neutralization to pH 6.0 or above, the matrix material is made largely passive to subsequent chemical or enzymatic reactions carried out on the analyte molecules presented on the probe tip surfaces. Since only a small fraction of the analyte molecules are used in each desorption/mass spectrometer measurement, the samples on the probe tips are available for in situ sequential chemical or enzymatic modifications. After modification the samples are analyzed by mass spectrometry. Analysis on the same probe tips provides a more accurate determination of the molecule and its characteristics, including its structure.

Mass spectrometry is performed on a modified Vestec model VT2000 or a MAS model SELDI Research Linear time-of-flight mass spectrometer which uses a frequency-tripled output from a Q-switched neodymiumyttrium aluminum garnet (Nd-YAG) pulsed laser (355 nm, 5 ns pulse). Ions desorbed by pulsed laser irradiation are accelerated to an energy of 30 keV and allowed to drift along a 2-meter field free drift region (maintained at $10^{-8}$ torr). Ion signals detected using a 20-stage discrete dynode electron multiplier are amplified by a factor of 10 using a fast preamplifier prior to being recorded using a 200 MS/s transient recorder (LeCroy TR8828D, 8-bit y-axis resolution) or a Tektronix digitizer capable of fast signal averaging. The laster irradiance is adjusted real-time, while monitoring the process on an-oscilloscope (Tektronix), in order to achieve optimum ion signal. Data reduction (peak centroid calculations and time to mass/charge conversions) are performed with PC-based software. A VG TOFSpec mass spectrometer which uses a nitrogen laser generating pulsed laser at 335 nm. or a Linear LDI 1700 mass spectrometer which uses a nitrogen laser generating pulsed laser 335 nm. may also be used.

I. Specific Analysis

Figure 1:
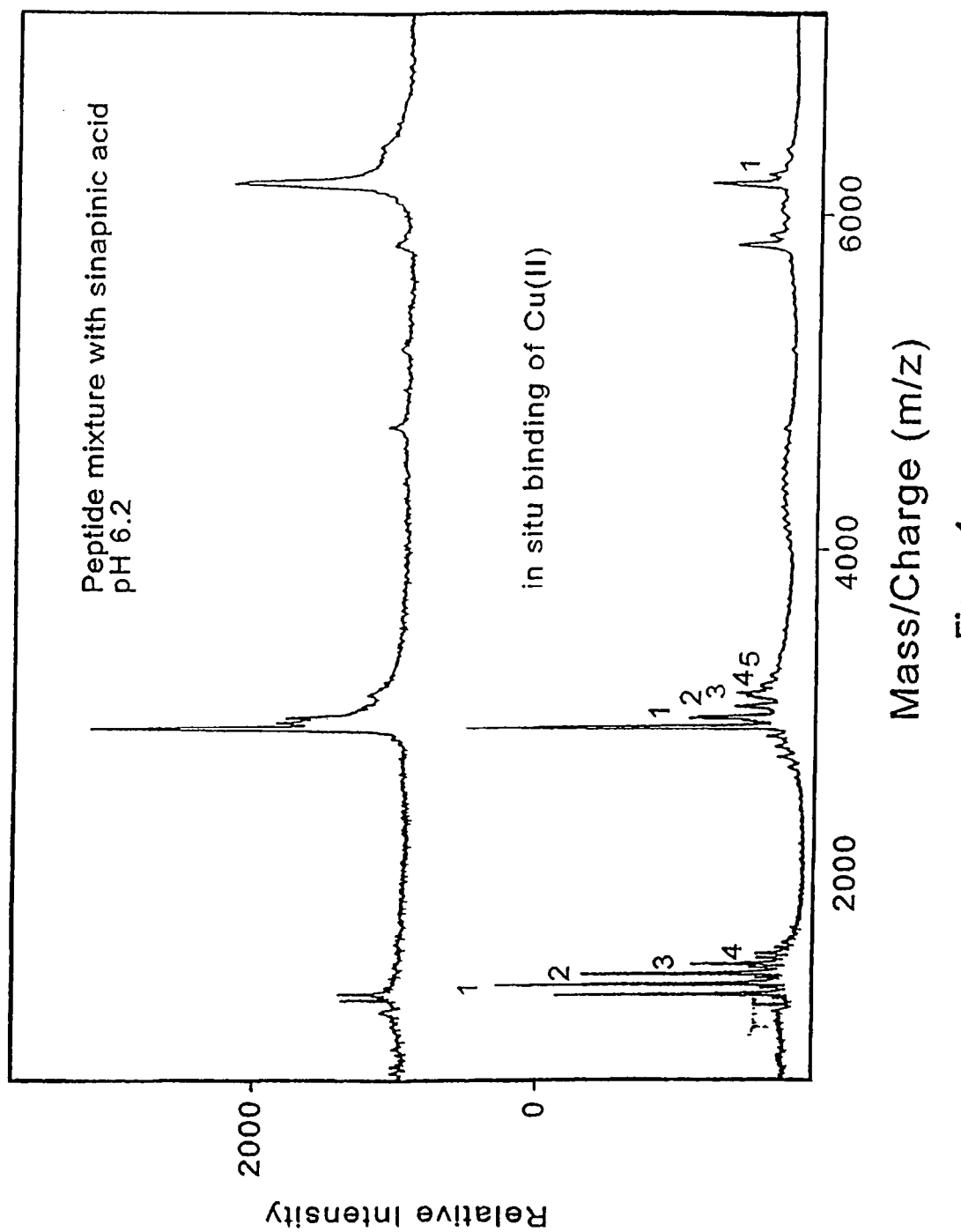
FIG. 1 (upper profile) shows the mass spectrum of the three peptides (human histidine rich glycoprotein metal-binding domains $(GHHPH)_2 G$ (1206 Da), $(GHHPH)_5 G$ (2904 Da), and human estrogen receptor dimerization domain (D473-L525) (6168.4 Da)) desorbed in the presence of neutralized energy absorbing molecules (sinapinic acid, pH 6.2).

1. Sinapinic acid (Aldrich Chemical Co., Inc., Milwaukee, Wis.) is suspended in water at 20 mg/ml (pH 3.88) and neutralized with triethylamine (Pierce, Rockford, Ill.) to pH 6.2-6.5. An aqueous mixture (1µl) of synthetic peptides, containing human histidine rich glycoprotein metal-binding domains (GHHPH)$_2$G (1206 Da), (GHHPH)$_5$G (2904 Da), and human estrogen receptor dimerization domain (D473-L525) (6168.4 Da) is mixed with 2 µl sinapinic acid (20 mg/ml water, pH 6.2) on a probe tip and analyzed by laser desorption time-of-flight mass spectrometry. After acquiring five spectra (average 100 laser shots per spectrum), the probe is retrieved, 2 µl of 20 mM CU(SO)$_4$ is added and the sample is reanalyzed by mass spectrometry. FIG. 1 (upper profile) shows the mass spectrum of the three peptides desorbed in the presence of neutralized energy absorbing molecules. FIG. 1 (lower profile) shows the in situ metal-binding of the peptides in the presence of neutral energy absorbing molecules. The (GHHPH)$_2$G peptide can bind at least 4 Cu(II), the (GHHPH)$_5$G peptide can bind at least 5 Cu(II) and the dimerization domain can bind at least 1 Cu(II) under the present experimental conditions. Similar result is obtained with α-cyano-4-hydroxycinnamic acid (20 mg/ml water) neutralized to pH 6.5.

Figure 2:
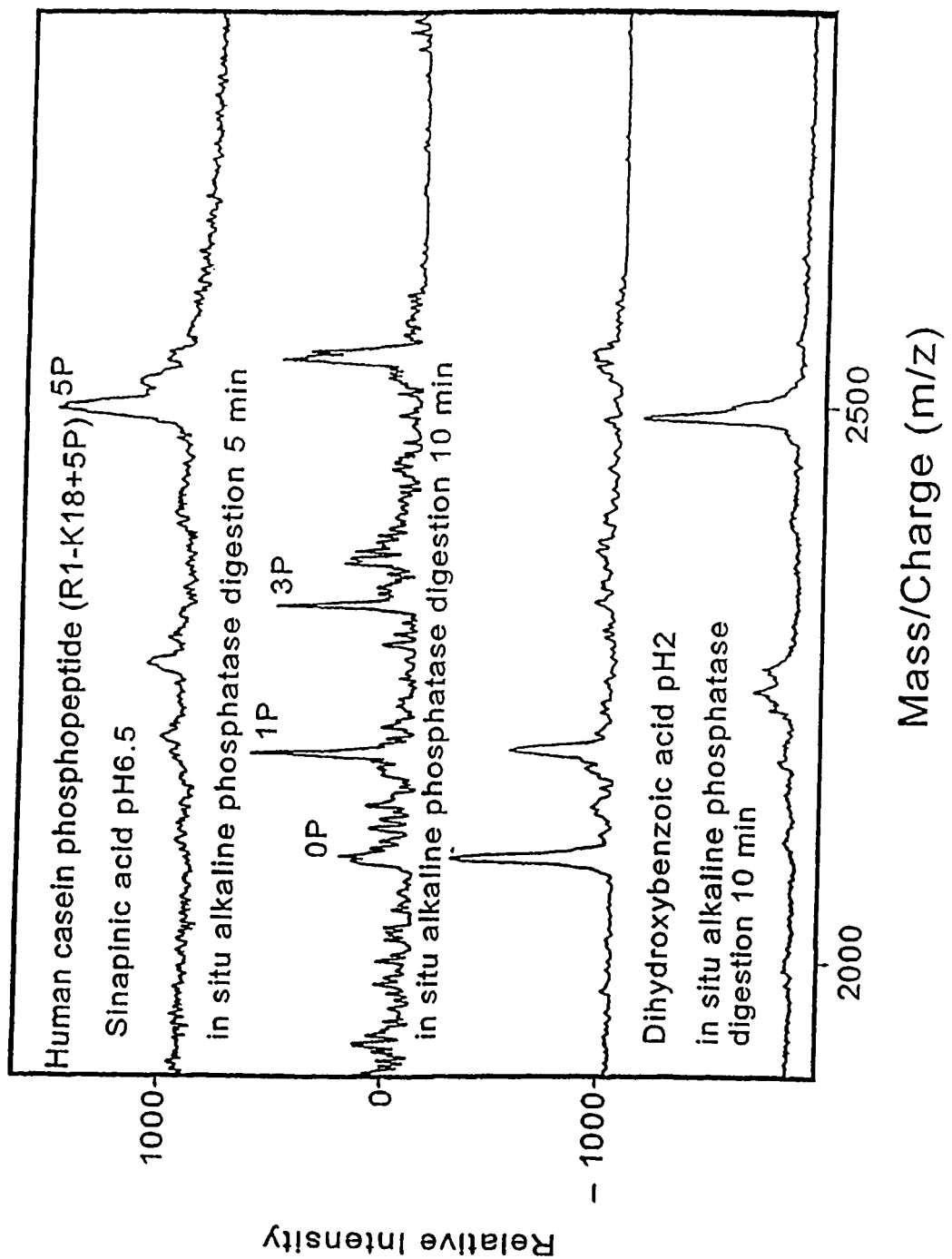
FIG. 2 (top profile) shows the mass spectrum of the human casein phosphopeptide (5P, 2488 Da) desorbed in the presence of neutralized energy absorbing molecules (sinapinic acid, pH 6.5).

2. An aliquot of 1 µl of human β casein phosphopeptide (R1-K18+5P) (2488 Da) is mixed with 1 µl of sinapinic acid (20 mg/ml water) neutralized to pH 6.5, and analyzed by laser desorption time-of-flight mass spectrometry. After acquiring five spectra (average 100 laser shots per spectrum), the probe is removed, the remaining phosphopeptide mixed with the neutralized sinapinic acid is digested directly on the probe tip by 0.5 µl of alkaline phosphatase (Sigma) and incubated at 23° C. for 5 min. After acquiring five spectra (average 100 laser shots per spectrum), the probe is removed, further digestion on remaining phosphopeptides is carried out by adding another aliquot of 0.5 µl of alkaline phosphatase and incubated at 23° C. for 5 min. The sample is re-analyzed by laser desorption mass spectrometry. FIG. 2 (top profile) shows the mass spectrum of the phosphopeptide desorbed in the presence of neutralized energy absorbing molecules. FIG. 2 (second from top profile) shows the in situ 5 min alkaline phosphatase digestion to remove phosphate groups from the phosphopeptide. The 0P, 1P and 3P peaks represent the products after removal of five, four and two phosphate groups respectively from the phosphopeptide. FIG. 2 (third from top profile) shows that further in situ digestion with alkaline phosphatase can result in almost complete removal of all phosphate groups from the phosphopeptide. In contrast, FIG. 2 (bottom profile) shows that in the control experiment where in situ alkaline phosphatase (0.5 µl) digestion is carried out in the presence of energy absorbing molecules without prior neutralization (e.g., sinapinic acid at pH 3.88 or dihydroxybenzoic acid at pH 2.07), very limited digestion occurred in 10 min at 23° C.

Figure 3:
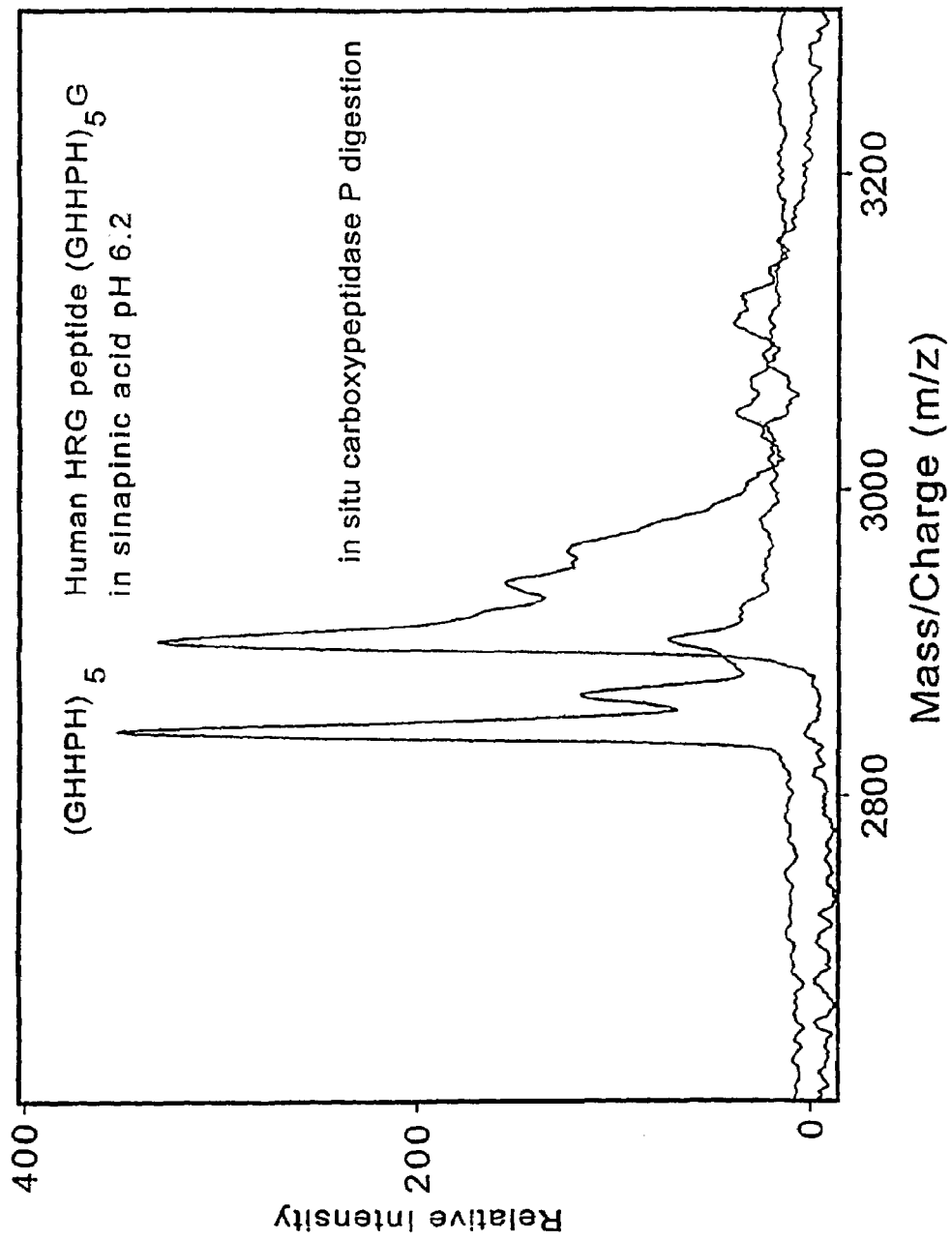
FIG. 3 shows a composite mass spectra of the $(GHHPH)_5G$ peptide (2904 Da) before (lower profile) and after (upper profile) in situ digestion by carboxypeptidase P in the presence of neutralized energy absorbing molecules (sinapinic acid, pH 6.2).

3. An aliquot of 1 µl of (GHHPH)$_5$G peptide (2904 Da) is mixed with 2 µl of sinapinic acid (20 mg/ml water) neutralized to pH 6.2, and analyzed by laser desorption time-of-flight mass spectrometry. After acquiring five spectra (average 100 laser shots per spectrum), the remaining peptides mixed with neutralized sinapinic acid are digested directly on the probe tip by 1 µl of carboxypeptidase P (Boehringer Mannheim Corp, Indianapolis, Ind.) and incubated at 23° C. for 30 min. The sample is analyzed by mass spectrometry. FIG. 3 shows a composite mass spectra of the peptide before (lower profile) and after (upper profile) in situ digestion by carboxypeptidase P in the presence of neutralized energy absorbing molecules. The decrease in mass represents the removal of a Gly residue from the C-terminal of the peptide.

These examples illustrate that neutralized energy absorbing molecules in aqueous solutions are more biocompatible in preserving the structure and function of the analytes even when added in large molar excess. Their presence results in no interference to in situ sequential chemical or enzymatic reactions on the remaining analyte.

EXAMPLE 2

Nonmetallic Probe Elements (Sample Presenting Surfaces)

It has been found that the probe elements (probe tips or sample presenting surfaces) used in the process of the invention need not be metal or metal-coated, as described in prior art procedures. The sample presenting surfaces are composed of a variety of materials, including porous or nonporous materials, with the porous materials providing sponge-like, polymeric, high surface areas for optimized adsorption and presentation of analyte.

Figure 4:
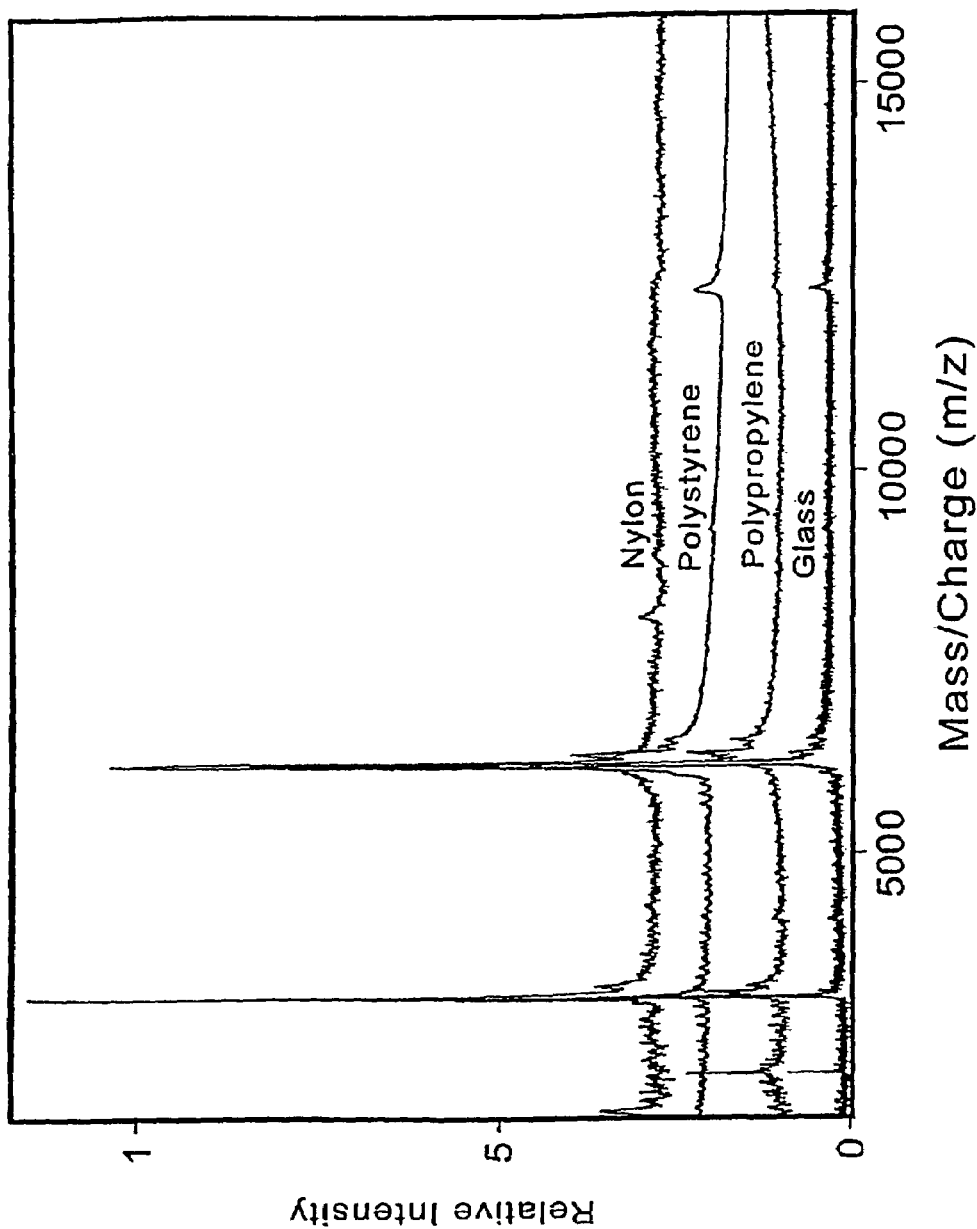
FIG. 4 shows a composite matrix-assisted laser desorption mass spectra of peptide mixtures desorbed from solid glass, polypropylene-coated stainless steel, polystyrene-coated stainless steel and solid nylon probe elements.

Polypropylene or polystyrene or polyethylene or polycarbonate are melted in an open flame and deposited as a thin layer on a 2 mm diameter stainless steel probe element so as to cover it completely. Solid glass rod or solid nylon filaments (up to 1.5 mm diameter) or polyacrylamide rod are cut into 1 cm segments and inserted into the stainless steel probe support. Magnetic stir bars (1.5×8 mm, teflon-coated) are inserted into stainless steel probe tip support. An aliquot of 1 µl of peptide mixture containing $(GHHPH)_5G$ and human estrogen receptor dimerization domain, is mixed with 2 µl of dihydroxybenzoic acid (dissolved in 30% methanol, 0.1% trifluoroacetic acid) on each of such probe elements and analyzed by laser desorption time-of-flight mass spectrometry. FIG. 4 shows that analytes could be desorbed from several examples of insulating, biocompatible surfaces.

These surfaces can be derivatized (at varying densities) to bind by chemical bonds (covalent or noncovalent) affinity adsorption reagents (affinity capture devices), energy absorbing molecules (bound "matrix" molecules) or photolabile attachment molecules. The geometry of the sample presenting surface is varied (i.e., size, texture, flexibility, thickness, etc.) to suit the need (e.g., insertion into a living organism through spaces of predetermined sizes) of the experiment (assay).

EXAMPLE 3

Affinity-Directed Laser Desorption

Surface Enhanced Affinity Capture, SEAC

This example describes the use of existing and new solid phase affinity reagents designed for the (1) capture (adsorption) of one or more analytes, (2) the preparation of these captured analytes (e.g., washing with water or other buffered or nonbuffered solutions to remove contaminants such as salts, and multiple cycles of washing, such as with polar organic solvent, detergent-dissolving solvent, dilute acid, dilute base or urea), and (3) most importantly, the direct transfer of these captured and prepared analytes to the probe surface for subsequent analyte desorption (for detection, quantification and/or mass analysis). Affinity capture devices are immobilized on a variety of materials, including electrically insulating materials (porous and nonporous), flexible or nonrigid materials, optically transparent materials (e.g., glass, including glass of varying densities, thicknesses, colors and with varying refractive indices), as well as less reactive, more biocompatible materials (e.g., biopolymers such as agarose, dextran, cellulose, starches, peptides, and fragments of proteins and of nucleic acids). The preferred probe tip, or sample surface, for selective adsorption/presentation of sample for mass analysis are (1) stainless steel (or other metal) with a synthetic polymer coating (e.g., cross-linked dextran or agarose, nylon, polyethylene, polystyrene) suitable for covalent attachment of specific biomolecules or other nonbiological affinity reagents, (2) glass or ceramic, and/or (3) plastics (synthetic polymer). The chemical structures involved in the selective immobilization of affinity reagents to these probe surfaces will encompass the known variety of oxygen-dependent, carbon-dependent, sulfur-dependent, and/or nitrogen-dependent means of covalent or noncovalent immobilization.

I. Surface Immobilized Metal Ion as the Affinity Capture Device

1. Cu(II) ion is chelated by iminodiacetate (IDA) group covalently attached to either porous agarose beads (Chelating Sepharose Fast Flow, Pharmacia Biotech Inc., Piscataway, N.J., ligand density 22-30 µmole/ml gel) or solid silica gel beads (Chelating TSK-SW, ToyoSoda, Japan, ligand density 15-20 .mu.mole/ml gel). A mixture of synthetic peptides containing neurotensin (1655 Da), sperm activating peptide (933 Da) and angiotensin I (1296.5 Da), is mixed with 50 µl packed volume of TSK-SW IDA-Cu(II) at pH 7.0 (20 mM sodium phosphate, 0.5M sodium chloride) at 23° C. for 10 min. The gel is separated from the remaining peptide solution by centrifugation and is then washed with 200 µl sodium phosphate, sodium chloride buffer, pH 7.0 three times to remove nonspecifically bound peptides. Finally, the gel is suspended in 50 µl of water. Aliquots of 2 µl gel suspension and nonadsorbed peptide solution are mixed with 1 µl of sinapinic acid (dissolved in methanol) on a stainless steel probe tip and analyzed by laser desorption time-of-flight mass spectrometry. After acquiring five spectra (average of 100 laser shots per spectrum) on various spots of the probe tip, the sinapinic acid is removed by methanol. An aliquot of 2 µl of 20 mM $CuSO_4$ is added, then mixed with 1 µl of sinapinic acid and reanalyzed by laser desorption time-of-flight mass spectrometry. After acquiring another five spectra (average of 100 laser shots per spectrum) on various spots of the probe tip, the sinapinic acid is removed by methanol. The remaining peptide adsorbed on IDA-Cu(II) gel beads is then digested with 1 µl of trypsin (Sigma) in 0.1 M sodium bicarbonate, pH 8.0 at 23° C. for 10 min in a moist chamber. The gel beads are then washed with water to remove enzyme and salt before 1 µl of sinapinic acid is added and the sample analyzed by laser desorption time-of-flight mass spectrometry. FIG. 5A, top profile, shows the molecular ions (and multiple Na-adducts) of sperm activating factor (933 Da) and neurotensin (1655 Da) in the remaining peptide solution unabsorbed by the IDA-Cu(II). There is no significant peak corresponding to angiotensin I (1296.5 Da). The mass spectrum in FIG. 5A, middle profile, shows the angiotensin I plus Na-adduct peaks that are selectively adsorbed on the IDA-Cu(II) gel. When the IDA-Cu(II) gel is further washed with 500 µl of water two times, the resulting mass spectrum shows only the parent angiotensin I ion and no other adduct peaks (FIGS. 5A and 5B, bottom profiles). FIG. 5B, middle profile, shows the in situ copper binding (1 and 2 Cu) by the angiotensin peptide. FIG. 5B, top profile, shows the in situ trypsin digestion of the angiotensin peptide at the single Arg2 position in the sequence.

This example illustrates that: a) laser desorption is successfully carried out on analyte affinity adsorbed on surface-immobilized metal ion; b) once bound, the surface is washed with various solvents to remove all contaminating compounds in the sample to give a very clean mass spectrum of the analyte; c) the affinity capture device selects only the analyte of defined structure (in this case angiotensin I is selectively adsorbed from the peptide mixture by IDA-Cu(II) because this peptide has a free N-terminal and two, histidine amino acid residues in the sequence, both properties are required for strong Cu(II)-binding; whereas both sperm activating factor and neurotensin have blocked N-terminal and no histidine amino acid residues in their sequences); d) structure and function analyses through sequential in situ chemical or enzymatic modifications is carried out on the adsorbed analyte with minimal loss at each step of reaction and wash; and e) a probe element with surface bound substrate (e.g., angiotensin I) is used to monitor specific enzyme activity (e.g., trypsin) in situ (e.g., inside the gastrointestinal tract of the human body).

2. A solution of horse heart myoglobin (325 pmole, 16,952 Da) is mixed with 50 µl of TSK-SW IDA-Cu(II) at pH 7.0 (20 mM sodium phosphate, 0.5M sodium chloride) at 23° C. for 10 min. The gel is separated from the solution by centrifugation and then washed with 500 µl of buffer two times and 500 µl of water two times. The quantity of remaining myoglobin in all these solutions are then estimated spectrophotometrically, the quantity adsorbed on the gel can then be calculated. The gel is suspended in 50 µl of water and then serially diluted into water. An aliquot of 0.5 µl of the diluted gel suspension is mixed with 1µl of sinapinic acid (dissolved in 30% methanol, 0.1% trifluoroacetic acid) and analyzed by laser desorption time-of-flight mass spectrometry. FIG. 6 shows that a detectable signal (signal/noise=6, after averaging 50 laser shots) of myoglobin is obtained with a calculated quantity of 4 to 8 fmole deposited on the probe tip.

This example illustrates that affinity adsorbed analytes on a surface are much more easier to transfer and are free from any loss by nonspecific adsorption to container and transfer device surfaces. The adsorbed analyte is sequestered on predetermined areas (that are even less than the laser spot size) of the sample presenting surface in low (atto to femtomole) quantities at a defined surface density or local concentration required for the efficient detection by laser desorption/ionization time-of-flight mass spectrometry.

3. The human β casein peptides (E2-K18) are synthesized on an Applied Biosystem Model 430A Peptide Synthesizer using the NMP-HOBt protocol. The Ser residues to be phosphorylated are coupled to the peptide chain without side chain protecting group. The unprotected Ser are first phosphinylated using di-t-butyl-N,N,-diisopropyl-phosphoramidite. The phosphite ester is then oxidized with t-butyl peroxide, washed, and cleaved from the resin. All the side chain protecting groups are removed with 95% trifluoroacetic acid. The crude phosphopeptides are extracted with methyl tbutyl ether and dried. This crude preparation of synthetic phosphopeptides is dissolved in 50 mM MES, 0.15M sodium chloride, pH 6.5 and mixed with 50 µl of tris(carboxymethyl)-ethylenediamine (TED)-Fe(III) immobilized on porous Sepharose (synthesized as described by Yip, T.-T. and Hutchens, T. W., Protein Expression and Purification 2: 355-362 (1991), ligand density 65 µmole/ml) at 23° C. for 15 min. The gel is washed with 500 µl of the same buffer three times and then with 500 µl of water once. An aliquot of 1 µl of gel is mixed with 1 µl of sinapinic acid (dissolved in 30% methanol, 0.1% trifluoroacetic acid) on the probe tip and analyzed by laser desorption time-of-flight mass spectrometry. After acquiring five spectra (average of 100 laser shots per spectrum) on various spots of the probe tip, the sinapinic acid is removed by methanol, and the remaining phosphopeptides adsorbed on TED-Fe(III) is digested directly on the probe tip by 1 µl of alkaline phosphatase (ammonium sulfate suspension, Sigma) in 50 mM HEPES pH 7.0 at 23° C. for 10 min. in a moist chamber. The gel is washed with water to remove enzyme and salt. Sinapinic acid is added and the sample is reanalyzed by laser desorption time-of-flight mass spectrometry. FIG. 7 (top profile) shows the distribution of casein peptide (1934 Da) with multiple phosphorylated forms. After in situ alkaline phosphatase digestion, only the original nonphosphorylated form remains (lower profile).

This example illustrates the application of SEAC as a quick monitor of phosphopeptide synthesis in a crude mixture without prior cleanup. The identity of the phosphopeptide is readily confirmed by in situ alkaline phosphatase digestion.

4. Aliquots of 100 µl of preterm infant formula (SIMILAC, Meade Johnson) and gastric content of preterm infant aspirated 90 min after feeding of the formula are mixed with 50 µl of TED-Fe(III) Sepharose in 0.1M MES, 0.15M sodium chloride, pH 6.5 at 23° C. for 15 min. The gel is washed with 500 µl of the same buffer three times and then with 500 µl of water once. Aliquots of 1 µl of gel suspensions or preterm infant formula or gastric aspirate are mixed with 2 µl of sinapinic acid (dissolved in 50% acetonitrile, 0.1% trifluoroacetic acid) on the probe tip and analyzed by laser desorption time-of-flight mass spectrometry. FIG. 8 shows that the mass spectrum of whole gastric aspirate (second from top profile) is quite similar to that of whole infant formula (bottom profile) in the 1,000-15,000 Da region. However, the mass spectra of analytes selectively adsorbed by TED-Fe(III) from the two samples are quite different, there are more low molecular weight phosphopeptides (i.e., bound by TED-Fe(III)) present in the gastric aspirate (top profile) than in the formula (second from bottom profile) due to the gastric proteolytic digestion of phosphoproteins present in the formula.

This example illustrates that SEAC is particularly useful in analyzing specific analytes in biological samples. Phosphopeptides are more difficult to detect in the presence of other contaminating components in a complex sample because they are less ionized in the positive ion mode. However, when the phosphopeptides are selectively adsorbed and all other components in the sample are removed, no such signal depression occurs.

5. Aliquots of 200 µl of human and bovine histidine-rich glycoprotein are mixed with 50 µl of IDA-Cu(II) Sepharose (Pharmacia) at pH 7.0 (20 mM sodium phosphate, 0.5M sodium chloride) at 23° C. for 10 min. The gel is washed with 500 µl buffer two times and 500 µl water once. Aliquots of 1 µl of gel are mixed with 2 µl of sinapinic acid (dissolved in 30% methanol 0.1% trifluoroacetic acid) and analyzed by laser desorption time-of-flight mass spectrometry. After acquiring five spectra (average of 100 laser shots per spectrum) on various spots of the probe tip, the sinapinic acid is removed by methanol wash. The remaining glycoproteins adsorbed on the IDA-Cu(II) gel is then digested with N-glycanase in 20 mM sodium phosphate, 0.5M sodium chloride, 3M urea, pH 7.0 at 37° C. overnight in a moist chamber. After washing with water to remove enzyme and salt, 2 µl of sinapinic acid is added and the sample is analyzed by mass spectrometry. After acquiring five spectra (average of 100 laser shots per spectrum) on various spots of the probe tip, the sinapinic acid is removed by methanol. Aliquots of 2 µl of trypsin in 0.1M sodium bicarbonate are added and incubated at 37° C. for 30 min in a moist chamber. After a water wash to remove enzyme and salt, sinapinic acid is added and the sample is analyzed by mass spectrometry. After acquiring five spectra (average of 100 laser shots per spectrum) on various spots of the probe tip, the sinapinic acid is removed by methanol. Aliquots of 2 µl of 20 mM $CuSO_4$ is added. This is followed by addition of 2 µl of sinapinic acid and then analyses by mass spectrometry. After acquiring five spectra (average of 100 laser shots per spectrum) on various spots of the probe tip, the sinapinic acid is removed by methanol. Aliquots of 2 µl of diethylpyrocarbonate (Sigma) in 5 mM HEPES, pH 6.5 are added and incubated at 23° C. for 30 min. After a water wash to remove chemicals and buffer salts, 2 µl of sinapinic acid is added and the sample is analyzed by mass spectrometry. To obtain a partial sequence of the metal-binding peptides, instead of modifying the histidine residues with diethylpyrocarbonate, add 1 µl of carboxypeptidase Y (Boehringer Mannheim) to the tryptic digest adsorbed on the surface and incubate at room temperature in a moist chamber for 5 min. Wash away the enzyme and salt with water, add 1 µl of sinapinic acid and analyze by mass spectrometry. FIG. 9A shows the composite mass spectra of human and bovine histidine-rich glycoprotein adsorbed on IDA-Cu(II) Sepharose before and after N-glycanase digestion. The mass shifts represent the removal of carbohydrate from the respective glycoproteins. FIG. 9B shows the composite mass spectra of trypsin digested peptides from the deglycosylated proteins of the two species (top profile for human protein, second from bottom profile for bovine protein) and in situ Cu(II)-binding of the trypsin digested peptides of the two species (second from top profile for human protein, bottom profile for bovine protein; the numbers 1, 2 indicate the number of copper bound). FIG. 9C shows that one such Cu(II)-binding peptide (bottom profile) has at least 4 His residues which are specifically modified by diethylpyrocarbonate to form 4 N-carbethoxy-histidyl adducts (1-4, top profile). FIG. 9D shows the partial C-terminal sequence of the major Cu-binding peptide in the bovine histidine rich glycoprotein. This example illustrates the effective use of SEAC to probe the structure and function of metal-binding domains of proteins from different species.

II. Surface Immobilized Antibody as the Affinity Capture Device

1. Polyclonal rabbit anti-human lactoferrin antibody is custom generated against purified human lactoferrin by Bethyl Laboratories (Montgomery, Tex.). The antibody is affinity-purified by thiophilic adsorption and immobilized lactoferrin columns. Sheep anti-rabbit IgG covalently attached to magnetic beads are obtained from Dynal AS, Oslo, Norway (uniform 2.8 µm supermagnetic polystyrene beads, ligand density 10 µg sheep IgG per mg bead). Human lactoferrin (1 nmole, $^{59}$Fe-labeled, 81,100 Da) is incubated with rabbit anti-human lactoferrin antibody in 20 mM sodium phosphate, 0.15M sodium chloride, pH 7.0 at 37° C. for 30 min. Subsequently, 40 µl of sheep anti-rabbit IgG on Dynabeads ($6-7\times10^8$ beads/ml) is added and incubated at 37° C. for 30 min. The beads are washed with 500 µl of sodium phosphate buffer three times and 500 µl water two times. The final amount of human lactoferrin bound to the complex is estimated to be 4 pmole. Approximately one-tenth of the beads is transferred to a teflon-coated magnetic probe tip, mixed with 2 µl of sinapinic acid (dissolved in 30% methanol, 0.1% trifluoroacetic acid) and analyzed by laser desorption time-of-flight mass spectrometry. FIG. 10 shows the presence of lactoferrin (81,143 Da) in the antigen-primary antibody-secondary antibody complex (upper profile), whereas the primary antibody-secondary antibody control (lower profile) shows only the rabbit antibody signal (149,000 Da for singly charged, and 74,500 Da for the doubly charged).

This example illustrates that a) laser desorption is successfully carried out on analyte affinity-adsorbed on surface immobilized antibody (if the analyte signal is unambiguously identified in a mixture of primary antibody-analyte complex, any capture device, e.g., surface immobilized secondary antibody, Protein A, Protein G, Streptavidin, of the primary antibodies is used in this method of identifying the analyte); b) the principle of protein discovery via specific molecular recognition events where one of the analytes is detected through its association with the primary target of capture; and c) the use of magnetic surface as efficient capture device.

2. Affinity-purified rabbit anti-human lactoferrin is covalently bound to the tip of an activated nylon probe element (2 mm diameter) via glutaraldehyde. This is immersed in 1 ml of preterm infant urine, pH 7.0, containing 350 fmole of human lactoferrin and stirred at 4-8° C. for 15 hr. The nylon probe tip is removed and washed with 1 ml of 20 mM sodium phosphate, 0.5M sodium chloride, 3M urea, pH 7.0 three times and 1 ml of water two times. An aliquot of 2 µl of sinapinic acid (dissolved in 30% methanol, 0.1% trifluoroacetic acid) is added and the sample is analyzed by laser desorption time-of-flight mass spectrometry. FIG. 11A shows the human lactoferrin molecular ion (signal/noise=2.5, average of 25 laser shots) in the mass spectrum. FIG. 11B shows the equivalent mass spectrum of whole preterm infant urine containing 1 nmole/ml of lactoferrin; the signal suppression caused by the presence of other components in the urine sample is so severe that even addition of several thousand fold excess over 350 fmole/ml of lactoferrin as described for FIG. 11A can not be detected.

This example illustrates the use of a SEAC device on a flat surface (a two-dimensional configuration) of a flexible probe element. This SEAC device may be used to isolate target analyte materials from undifferentiated biological samples such as blood, tears, urine, saliva, gastrointestinal fluids, spinal fluid, amniotic fluid, bone marrow, bacteria, viruses, cells in culture, biopsy tissue, plant tissue or fluids, insect tissue or fluids, etc. The specific affinity adsorption step cleaned up the analyte from contamination by other components in a complex sample and thus overcome the signal depression effect especially when the analyte is present in very low concentration (femtomole/ml).

3. Further improvement of detection sensitivity by the SEAC technique is achieved by amplification of a label bound to the analyte. One way of doing this is by the combination of enzyme catalysis and the streptavidin-biotin system. After capturing minute quantities of lactoferrin on a nylon probe element as described in Example 3.II.2. biotinylated anti-lactoferrin antibody or biotinylated single-stranded DNA is used to bind specifically to the lactoferrin. Streptavidin is then added to bind specifically to the biotinylated label. Finally biotinylated alkaline phosphatase is added to bind specifically to the streptavidin. Since several such biotinylated alkaline phosphatase can bind to one streptavidin, there is a primary level of amplification. The second level of amplification comes from the enzyme catalysis where the enzyme can achieve a turnover number of $10^2$ to $10^3$ min$^{-1}$. Assay of alkaline phosphatase enzyme activity can easily be accomplished by using a low molecular weight phosphorylated substrate such as ATP, NADPH or a phosphopeptide. The efficiency of detecting the mass shift of a low molecular weight analyte is much higher than that of a 80 kDa glycoprotein.

4. The ultimate improvement of detection at the present moment is achieved by 30 the amplification based on the polymerase chain reaction principle. After capturing minute quantities of lactoferrin on a nylon probe element as described in Example 3.II.2. biotinylated anti-lactoferrin antibody or biotinylated single-stranded DNA is used to bind specifically to the lactoferrin. Streptavidin is then added to bind specifically to the biotinylated label. A piece of biotinylated linear DNA is finally added to bind to the streptavidin. This bound DNA label is amplified in a 30-cycle polymerase chain reaction procedure. Each cycle consists of a 1 min denaturation step at 94° C., a 1 min annealing reaction at 58° C., and a 1 min primer extension reaction at 72° C. This technique provides amplification factors in the $10^6$ fold range. The amplified DNA is detected directly by laser desorption mass spectrometry using 3-OH picolinic acid as the matrix.

5. Polyclonal rabbit anti-bovine histidine rich glycoprotein antibody is custom generated against purified bovine histidine rich glycoprotein by Bethyl Laboratories (Montgomery, Tex.). The antibody is affinity-purified by thiophilic adsorption and immobilized bovine histidine rich glycoprotein columns. The purified antibody is immobilized on AffiGel 10 (BioRad Laboratories, Hercules, Calif., ligand density 15 µmole/ml gel) according to manufacturer's instruction. An aliquot of 200 µl of bovine colostrum is diluted with 200 µl of 20 mM sodium phosphate, pH 7.0 and mixed with 50 µl of immobilized antibody at 23° C. for 30 min. The gel is washed with 500 µl of 20 mM sodium phosphate, 0.5M sodium chloride, 3M urea, pH 7.0 three times and 500 µl of water two times. An aliquot of 1 µl of the washed gel is mixed with 2 µl of sinapinic acid (dissolved in 30% methanol, 0.1% trifluoroacetic acid) on the probe tip and analyzed by laser desorption time-of-flight mass spectrometry. FIG. 12 shows the composite mass spectra of purified bovine histidine rich glycoprotein (lower profile) and proteins affinity adsorbed from bovine colostrum (upper profile). The result indicates the presence of intact histidine rich glycoprotein and its major proteolytic fragments in bovine colostrum.

This example illustrates the effective use of SEAC as a fast and simple technique to detect and characterize new proteins in a small quantity of biological fluid. This result supports the initial findings obtained by the very labor-intensive technique of immunoblotting of polyacrylamide gel electrophoresis.

6. Antibody epitope mapping is easily achieved with the SEAC technique. Three different sources of anti-human follicle stimulating hormone (a polyclonal specific against beta FSH from Chemicon International, Temecula, Calif., a monoclonal specific against beta 3 epitope from Serotec, Indianapolis, Ind., a monoclonal from Biodesign, Kennebunk, Me.) are immobilized on AffiGel 10 according to manufacturer's instruction. These immobilized antibodies are all tested to bind specifically the follicle stimulating hormone by incubating with two different preparations of follicle stimulating hormone (a semipure preparation from Chemicon, and a crude preparation from Accurate Chemical and Scientific Corp.) and then analyzed by mass spectrometry in the presence of sinapinic acid. Then the semipure preparation of human FSH (Chemicon) is digested with trypsin and separate aliquots (7 ul) are reacted with the immobilized antibodies (10 ul of 1:1 gel suspension) in phosphate-buffered saline at 4° C. for 2 hr. After washing with phosphate-buffered saline and water, the adsorbed proteins are analyzed by laser desorption mass spectrometry in the presence of sinapinic acid. FIG. 13 shows the composite mass spectra of the peptides of follicle stimulating hormone recognized by the different antibodies. The two monoclonal antibodies clearly recognize different epitopes, whereas the polyclonal recognizes multiple epitopes common to those recognized by both monoclonals.

III. Surface Immobilized Nucleic Acid as the Affinity Capture Device

1. Single-stranded DNA immobilized on 4% agarose beads are obtained from GIBCO BRL (Gaithersburg, Md., ligand density 05-1.0 mg DNA/ml gel). An aliquot of $^{125}$I-human lactoferrin (equivalent to 49 nmole) is mixed with 100 µ.l of immobilized single-stranded DNA in 20 mM HEPES, pH 7.0 at room temperature for 10 min. The gel is washed with 500 µl of HEPES buffer five times and then suspended in equal volume of water. The amount of lactoferrin bound per bead is estimated to be 62 fmole by determining the radioactivity and counting the number of beads per unit volume. Various numbers of beads (from 1 to 12) are deposited on 0.5 mm diameter probe tips, mixed with 0.2 µl of sinapinic acid (dissolved in 30% methanol, 0.1% trifluoroacetic acid) and analyzed by laser desorption time-of-flight mass spectrometry. FIG. 14 shows the mass spectrum of lactoferrin affinity adsorbed on a single bead of single-stranded DNA agarose. This is a representative spectrum from a total of five (average of 100 laser shots per spectrum) obtained from the single bead.

This example illustrates that laser desorption is successfully carried out on analyte affinity adsorbed on surface immobilized biopolymer such as nucleic acid. The specificity of interaction between human lactoferrin and DNA has been documented and effectively exploited in capturing minute quantities of lactoferrin from preterm infant urine. In this case, the combination of the efficiency of transferring the lactoferrin affinity capture device with the sensitivity of laser desorption mass spectrometry greatly increases the sensitivity of detection.

2. An aliquot of 1 ml of preterm infant urine containing 30 pmole of $^{59}$Fe-human lactoferrin is mixed with 20 µl of single-stranded DNA agarose in 0.1 M HEPES pH 7.4 at 23° C. for 15 min. The gel is washed with 500 µl of HEPES buffer two times and 500 µl of water two times. The gel is suspended in equal volume of water and 1 µl of the suspension (containing not more than 350 fmole of adsorbed lactoferrin as determined by radioactivity) is mixed with 1 µl of sinapinic acid (dissolved in 30% methanol, 0.1% trifluoroacetic acid) on a probe tip and analyzed by laser desorption time-of-flight mass spectrometry. FIG. 15 shows the mass spectrum of lactoferrin extracted from urine by surface immobilized DNA as the affinity capture device.

This example illustrates the efficiency and sensitivity of detecting minute quantities of high molecular weight analyte in biological fluid with the DNA capture device.

IV. Surface Immobilized Miscellaneous Biomolecule as the Affinity Capture Device 1. Soybean trypsin inhibitor (Sigma) is immobilized on AffiGel 10 (BioRad) according to manufacturer's instructions. An aliquot of 100 µl of human duodenal aspirate is mixed with 50 µl of surface immobilized soybean trypsin inhibitor at pH 7.0 (20 mM sodium phosphate, 0.5M sodium chloride) at 23° C. for 15 min. The gel is then washed with 500 µl of phosphate buffer three times and 500 µl of water two times. Aliquots of 1 µl of gel suspension or the original duodenal aspirate are mixed with 2 µl of sinapinic acid (dissolved in 50% acetonitrile, 0.1% trifluoroacetic acid) and analyzed by laser desorption time-of-flight mass spectrometry. FIG. 16A shows the composite mass spectra of the total duodenal aspirate (lower profile) and the proteins adsorbed by surface immobilized soybean trypsin inhibitor (upper profile). The major peak in the affinity captured sample represents trypsin. Similar results are obtained with only 1 μl of duodenal fluid deposited on a) the tip of a nylon probe element coupled to soybean trypsin inhibitor via glutaraldehyde and b) the tip of an acrylic probe element coated with polyacrylamide coupled to soybean trypsin inhibitor via either glutaraldehyde or divinyl sulfone (FIG. 16B).

These results indicate a) the unambiguity in detecting and characterizing a specific analyte in biological fluids and b) the feasibility of in situ sampling by inserting a flexible (e.g. nylon) probe element through an endoscope directly into the human body (e.g., small intestine) for diagnostic purposes.

2. Streptavidin immobilized on Dynabead (uniform, 2.8 μm, superparamagnetic, polystyrene beads) is obtained Dynal, AS, Oslo, Norway. Aliquots of 150 μl of human plasma or urine containing 18 pmole of biotinylated insulin (Sigma) are mixed with 20 μl suspension of streptavidin Dynabead at pH 7.0 (20 mM sodium phosphate, 0.5M sodium chloride) at 23° C. for 10 min. The beads are then washed with 500 μl buffer containing 3M urea three times and 500 μl water once. Aliquots of 0.5 μl of the bead suspension are mixed with 2 μl of sinapinic acid (dissolved in 30% methanol, 0.1% trifluoroacetic acid) and analyzed by laser desorption time-of-flight mass spectrometry. FIG. 17A shows the mass spectrum of biotinylated insulin affinity adsorbed from urine. The multiple peaks represent insulin derivatized with one to three biotin groups. FIG. 17B shows the mass spectrum of biotinylated insulin affinity adsorbed from plasma.

This example illustrates that laser desorption is carried out on analyte affinity adsorbed via the biotin-streptavidin binding. In view of the tight binding between biotin and avidin ($Ka=10^{15}$ $M^{-1}$), this system serves as an ideal SEAC device for proteins and nucleic acid on a probe surface where in situ sequential chemical and enzymatic modifications are performed.

3. Human estrogen receptor DNA-binding domain (84 residues) is expressed in bacteria. The plasmid expression vector pT$_7$ERDBD (J. Schwabe, MRC Laboratory of Molecular Biology, Cambridge, UK) is transformed into *E. coli* BL21(DE3)plyS cells (Novagene). Expression of the DNA binding domain is induced by 1 mm isopropylthiogalactoside (GIBCO BRL) and the bacteria are harvested after induction for 3 hr. Whole induced bacteria are analyzed directly by matrix-assisted laser desorption/ionization mass spectrometry to verify that the DNA-binding domain is the major peptide synthesized. The peptide is purified by reverse phase HPLC from the bacterial lyzate, and immobilized on AffiGel 10 (BioRad). A 30-bp DNA sequence containing the estrogen response element is synthesized by Genosys (Houston, Tex.). Interaction of surface affinity adsorbed apo-, Zn- and Cu-bound forms of DNA-binding domain with sequence specific nucleic acid (estrogen response element) are studied on glass probe elements using 3-hydroxypicolinic acid as the matrix.

This example illustrates the use of protein surface functional domain as capture device in SEAC. The effect of metal-binding on the structure and function of such protein surface domains can be investigated.

4. Different aliquots of lectins immobilized on surfaces (e.g., Con A-Sepharose, wheat germ lectin-Sepharose, Pharmacia) are used to bind the glycopeptides in human and bovine histidine-rich glycoprotein tryptic digests. After washing with buffers and water to remove unbound peptides, sequential enzyme digestion are performed in situ with FUCase I, MANase I, HEXase I, NANase III and PNGase (Glyko, Inc, Novato, Calif.). The samples are analyzed with laser desorption time-of-flight mass spectrometry to study the carbohydrate composition of the glycopeptides in the two proteins. This example illustrates the use of SEAC device to tether a glycopeptide, the carbohydrate component of which can then be sequenced in situ.

V. Surface Immobilized Dye as the Affinity Capture Device

Cibacron Blue 3GA-agarose (Type 3000, 4% beaded agarose, ligand density 2-5 pmoles/ml gel) is obtained from Sigma. An aliquot of 200 μl of human plasma is mixed with 50 μl of surface immobilized Cibacron Blue at pH 7.0 (20 mM sodium phosphate, 0.5M sodium chloride) at 23° C. for 10 min. The gel is then washed with 500 μl of buffer three times and 500 μl of water two times. An aliquot of 1 μl of gel suspension is mixed with 2 μl of sinapinic acid (dissolved in 50% acetonitrile, 0.1% trifluoroacetic acid) and analyzed by laser desorption time-of-flight mass spectrometry. FIG. 18 shows the selective adsorption of human serum albumin (doubly charged ion $[M+2H]^{2+}$, 32,000 m/z, singly charged ion $[M+H]^+$, 64,000 m/z, dimer ion, $2[M+H]^+$, 128,000 m/z) from the serum sample by surface immobilized Cibacron Blue (lower profile). Other immobilized dyes tested included Reactive Red 120-agarose, Reactive Blue-agarose, Reactive Green-agarose, Reactive Yellow-agarose (all from Sigma) and each selects different proteins from human plasma.

EXAMPLE 4

Surface Enhanced Neat Desorption (SEND)

This example describes the method for desorption and ionization of analytes in which the analyte is not dispersed in a matrix crystalline structure but is presented within, on or above an attached surface of energy absorbing molecules in a position where it is accessible and amenable to a wide variety of chemical, physical and biological modification or recognition reactions. The surface is derivatized with the appropriate density of energy absorbing molecules bonded (covalently or noncovalently) in a variety of geometries such that mono layers and multiple layers of attached energy absorbing molecules is used to facilitate the desorption of analyte molecules of varying masses.

The Examples shown below (Groups I-IV) demonstrate the combined SEND and SEAC where the adsorbed (bonded) energy absorbing molecules also act as affinity adsorption reagents to enhance the capture of analyte molecules.

I. Energy Absorbing Molecules Bound by Covalent Bond to the Surface

1. Cinnamamide (Aldrich) (not a matrix at laser wavelength of 355 nm by prior art) is dissolved in isopropanol: 0.5M sodium carbonate (3:1) and mixed with divinyl sulfone (Fluka, Ronkonkoma, N.Y.) activated Sepharose (Pharmacia) at 23° C. for 2 hr. The excess energy absorbing molecules are washed away with isopropanol. The proposed molecular structure is presented in FIG. 19. Aliquots of 2 μl of the bound or free molecules are deposited on the probe tips, 1 μl of human estrogen receptor dimerization domain in 0.1% trifluoroacetic acid is added on top and analyzed by laser desorption time-of-flight mass spectrometry. The result shows that peptide ion signals are detected only on the bound energy absorbing molecule surface (FIG. 20, top profile), the free molecules are not effective (FIG. 20, bottom profile).

2. Cinnamyl bromide (Aldrich) (not a matrix at laser wavelength of 355 nm by prior art) is dissolved in isopropanol: 0.5M sodium carbonate (3:1) and mixed with divinyl sulfone (Fluka) activated Sepharose at 23° C. for 15 hr. The excess energy absorbing molecules are washed away with isopropanol. The proposed molecular structure is presented in FIG. 21. Aliquots of 2 μl of the bound or free molecules are deposited on the probe tips, 1 µl of peptide mixtures in 0.1% trifluoroacetic acid is added on top and analyzed by laser desorption time-of-flight mass spectrometry. The result shows that peptide ion signals are detected only on the bound energy absorbing molecule surface (FIG. 22, top profile), the free molecules are not effective (FIG. 22, bottom profile).

3. Dihydroxybenzoic acid is activated by dicyclohexylcarbodiimide and mixed with Fmoc-MAP 8 branch resin (Applied Biosystems, Forster City, Calif.) at 23° C. for 15 hr. The excess energy absorbing molecules are washed away by methanol. The proposed molecular structure is presented in FIG. 23. Aliquots of 1 µl of the MAP 8 branch surface with and without bound energy absorbing molecules are deposited on the probe tips, 1 µl of peptide mixtures in 0.1% trifluoroacetic acid was added on top and analyzed by laser desorption time-of-flight mass spectrometry. The result shows that peptide ion signals are detected only on the surface with bound energy absorbing molecules (FIG. 24, bottom profile), the control surface without any energy absorbing molecules is not effective (FIG. 24, top profile).

4. α-cyano-4-hydroxycinnamic acid is dissolved in methanol and mixed with AffiGel 10 or AffiGel 15 (BioRad) at various pHs at 23° C. for 2-24 hours. The excess energy absorbing molecules are washed away by methanol. Aliquots of 2 µl of the bound molecules are deposited on the probe tips, 1 µl of peptide mixtures or myoglobin, or trypsin or carbonic anhydrase is added on top and analyzed by laser desorption time-of-flight mass spectrometry. The result shows that myoglobin ion signal is detected on the surface with bound energy absorbing molecules (FIG. 25) with very little contaminating low mass ion signals (FIG. 25).

5. A 40% polyacrylamide solution is prepared and cast into the desired shape of a probe tip. The gel is allowed to air dry until no noticeable reduction in size is observed. The tip is submerged into a 9% glutaraldehyde/buffer (v/v) solution and incubated with gentle shaking at 37° C. for 2 hours. After incubation, buffer is used to rinse off excess glutaraldehyde. The activated tip is added to a saturated buffered energy absorbing molecule solution and incubated at 37° C. (approx.) for 24 hours (approx.) with gentle shaking. Organic solvents are used to solubilize the energy absorbing molecules in situations that required it. The tip is rinsed with buffer and placed into a 9% ethanolamine/water (v/v) solution to incubate at 25° C. with gentle shaking for 30 minutes. Next, the tip is rinsed with buffer and added to a 5 mg/mL solution of sodium cyanoborohydride/buffer to incubate at 25° C. for 30 minutes. Finally, the tip is rinsed well with buffer and stored until use. The same reaction is carried out on nylon tips which is prepared by hydrolysis with 6N HCl under sonication for 2 minutes and then rinsed well with water and buffer. The same reaction is also performed on acrylic tips activated by soaking in 20% NaOH for 7 days with sonication each day for 30-60 min and then washed. The proposed general molecular structure of the surface is shown in FIG. 26.

6. A 40% polyacrylamide solution is prepared and cast into the desired shape of a probe tip. The gel is air dried until no noticeable reduction in size is observed. A 0.5M sodium carbonate buffer with a pH of 8.8 is prepared as rinsing buffer. The tip is next placed into a solution of divinyl sulfone (Fluka) and buffer at a ratio of 10:1, respectively, and incubated for 24 hours. The tip is rinsed with buffer and placed into an energy absorbing molecule buffered solution at a pH of 8 to incubate for 2 hours. The same reaction is carried out on nylon tips which is prepared by hydrolysis with 6N HCl under sonication for 2 minutes and then rinsed well with water and buffer. The same reaction is also performed on acrylic tips activated by soaking in 20% NaOH for 7 days with sonication each day for 30-60 min and then washed. The proposed general molecular structure of the surface is shown in FIG. 27.

7. A 40% polyacrylamide solution is prepared and cast into the desired shape of a probe tip. The gel is air dried until no noticeable reduction in size is observed. An energy absorbing molecule solution at 100 mg/mL in dichloromethane/NMP (2:1, respectively) and a 1M dicyclohexylcarbodiimide/NMP solution are mixed at a ratio of 1:2 (EAM:DCC), respectively. The EAM/DCC solution is next incubated at 25° C. for 1 hour while stirring. After incubation, a white precipitate is observed. The white precipitate is filtered in a sintered glass filter. The flow through is the DCC activated EAM. Next, the tip is placed into the DCC activated EAM solution and incubated at 25° C. for 2 hours (approx.). The tip is finally rinsed with a variety of solvents such as acetone, dichloromethane, methanol, NMP, and hexane. The same reaction is carried out on nylon tips which is prepared by hydrolysis with 6N HCl under sonication for 2 minutes and then rinsed well with water and buffer. The same reaction is also performed on acrylic tips activated by soaking in 20% NaOH for 7 days with sonication each day for 30-60 min and then washed. The proposed general molecular structure of the surface is shown in FIG. 28.

8. A 40% polyacrylamide solution is prepared and cast into the desired shape of a probe tip. The gel is air dried until no noticeable reduction in size is observed. A 100 mg/mL solution of N-.alpha.-Fmoc-N-.epsilon.-Fmoc-L-lysine in dichloromethane/NMP (2:1 respectively) and a 1M DCC/NMP solution are mixed at a ratio of 1:2 (lysine:DCC), respectively. The lysine/DCC solution is incubated at 25° C. for 1 hour while stirring. After incubation, a white precipitate is observed and filtered with a sintered glass filter. The flow through is DCC activated lysine. The tip is placed into the DCC activated lysine solution and incubated at 25° C. for 2 hours (approx.). The tip is next placed into 5 mL of piperidine and incubated at 25° C. for 45 minutes with gentle stirring. DCC activated lysine is repeatedly reacted in consecutive cycles with the tip until the desired lysine branching is attained. An EAM solution at 100 mg/mL in dichloromethane/NMP (2:1, respectively) and a 1M DCC/NMP solution are mixed at a ratio of 1:2 (EAM:DCC), respectively. The EAM/DCC solution is incubated at 25° C. for 1 hour while stirring. After incubation, a white precipitate is observed and filtered with a sintered glass filter. The flow through is the DCC activated EAM. The EAM contains an acid functional group that reacts with the DCC. The tip is placed into the DCC activated EAM solution and incubated at 25° C. for 2 hours (approx.) with gentle shaking. Finally, the tip is rinsed with excess dichloromethane, NMP, and methanol before use. The same reaction is carried out on nylon tips which is prepared by hydrolysis with 6N HCl under sonication for 2 minutes and then rinsed well with water and buffer. The same reaction is also performed on acrylic tips activated by soaking in 20% NaOH for 7 days with sonication each day for 30-60 min and then washed. The proposed general molecular structure of the surface is shown in FIG. 29.

II. Energy Absorbing Molecules Bound by Co-Ordinate Covalent Bond to the Surface 1. Thiosalicylic acid (Aldrich) is dissolved in either water or 50% methanol in water or methanol. These solutions are either used as such or the pH of the solutions is adjusted to 6.5 with 0.5M sodium bicarbonate or ammonium hydroxide or triethylamine. Cu(II) ion are chelated by either iminodiacetate (IDA) (Chelating Sepharose Fast Flow, Pharmacia) or tris(carboxymethyl)ethyleneidamine (TED) (synthesized as described by Yip and Hutchens, 1991) immobilized on gel surface. The solutions of energy absorbing molecule are mixed with the IDA-Cu(II) or TED-Cu(II) gel at 4° C. for 5 min to 15 hours. The excess energy absorbing molecules are washed away with either water or 50% methanol in water or methanol. The proposed molecular structure of the surface is shown in FIG. 30. Aliquots of 1 μl of the bound energy absorbing molecules are deposited on the probe tips, 1 μl of peptide mixtures or estrogen receptor dimerization domain or myoglobin in 0.1% trifluoroacetic acid is added on top and analyzed by laser desorption time-of-flight mass spectrometry. FIG. 31 shows one representative mass spectrum of estrogen receptor dimerization domain desorbed from this surface.

2. Sequential in situ reactions are readily accomplished on samples deposited on top of an EAM surface. Thiosalicylic acid co-ordinate covalently bound to IDA-Cu(II) on a probe surface is prepared as described in Section 2.1. An aliquot of 1 μl of (GHHPH)$_5$G peptide is deposited on the surface and analyzed by laser desorption time-of-flight mass spectrometry. After obtaining several spectra (each an average of 50 laser shots), the sample is removed. An aliquot of 2 μl of carboxypeptidase Y (Boehringer Mannheim) is added directly on the surface and incubated at 37° C. in a moist chamber for 5 min to 1 hr. The in situ enzyme digestion is terminated by 1 μl of 0.1% trifluoroacetic acid and the sample is reanalyzed by mass spectrometry.

3. Another illustration of sequential in situ reaction is trypsin digestion followed by C-terminal sequencing. Thiosalicylic acid co-ordinate covalently bound to IDA-Cu (II) on a probe surface is prepared as described in Section 2.1. An aliquot of 1 μl of estrogen receptor dimerization domain (6168.4 Da) is deposited on the surface and analyzed by laser desorption time-of-flight mass spectrometry. After obtaining several spectra (each an average of 20 laser shots), the sample is removed. An aliquot of 2 μl of trypsin (Sigma) in 0.1M sodium bicarbonate is added on the surface and incubated at 37° C. for 15 min. The in situ enzyme digestion is terminated by 1 μl of 0.1% trifluoroacetic acid and the sample is reanalyzed by mass spectrometry. After obtaining several spectra (each an average of 20 laser shots), the sample is removed. An aliquot of 2 μl of carboxypeptidase Y (Boehringer Mannheim) is added directly on the surface and incubated at 37° C. in a moist chamber for 1 hr. The in situ enzyme digestion is terminated by 1 μl of 0.1% trifluoroacetic acid and the sample is reanalyzed by mass spectrometry.

III. Energy Absorbing Molecules Bound by Ionic Bond to the Surface

Sinnapinic acid or α-cyano-4-hydroxycinnamic acid are suspended in water and the pH is adjusted to 6.6 with dilute sodium hydroxide. Tentacle DEAE Fractogel (EM Separations, Gibbstown, N.J.) is washed with 20 mM HEPES, pH 6.0 and suction dried. The energy absorbing molecules solution is mixed with the DEAE gel at 23° C. for 5 hours. The gel is washed with water until all excess energy absorbing molecules were removed. The proposed molecular structure of the surface is shown in FIG. 32. An aliquot of 0.5 μl of the bound energy absorbing molecules is deposited on the probe tips, 1 μl of estrogen receptor dimerization domain or myoglobin in 0.1% trifluoroacetic acid is added on top and analyzed by laser desorption time-of-flight mass spectrometry. FIGS. 33A and B show the mass spectra.

IV. Energy Absorbing Molecules Bound Hydrophobic/Van der Waals Bonds to the Surfaces 1. α-cyano-4-hydroxcinnamic acid is dissolved in 50% methanol in water and dimethylsulfoxide. This is mixed with aminomethylated polystyrene at 23° C. for 15 hours. The excess energy absorbing molecules are washed away with 50% methanol in water. The proposed molecular structure is shown in FIG. 34. An aliquot of 1 μl of the bound energy absorbing molecules is deposited on the probe tip, 1 μl of peptide is added on top and analyzed by laser desorption time-of-flight mass spectrometry.

EXAMPLE 5

Surfaces Enhanced for Photolabile Attachment and Release (SEPAR)

The linear assembly of individual building blocks (monomers) that define the structure and characteristics of biopolymers such as DNA, RNA, and protein are often unknown but are decoded or sequenced (in whole or in part) with a method that involves differential mass determinations of partially digested (i.e., chemical or enzymatic) biopolymer analytes by laser desorption/ionization time-of-flight (TOF) mass spectrometry (MS).

Given biopolymers are first coupled to the SELDI probe element surface through one or more (multiple) covalent photolytic (i.e., light sensitive) bonds. Next, various number of individual units (monomers) at the ends of the biopolymer are cleaved (i.e., removed) in a single reaction by enzymatic or chemical methods. The analytes remaining on the probe element surface consist of a variety (population) of mass-defined biopolymers with different numbers of their end monomer units missing. A small but sufficient portion of the modified biopolymers are uncoupled (untethered) from the probe element surface by laser light, that is, by cleavage of the photolytic bonds with LTV light between 260 nm and 365 nm. The uncoupled biopolymers are desorbed/ionized by time-of-flight mass spectrometry.

I. Coupling of Biopolymers to the SELDI Surface

Three components are involved: 1) a surface that is activated to react with either amine or carboxyl groups, or both; 2) photolytic compound, typically azo-based compound of the general formula $R_1$—N=N—$R_2$, e.g., 5-(4-aminophenylazo)salicylic acid (Aldrich), azodicarbonamide (Aldrich), or other mechanisms generating such photolytic bond such as the active hydrogen reactive chemistries with diazonium compounds are used; and 3) biopolymer, e.g., proteins, nucleic acids, carbohydrates.

A photolytic compound must first be attached to activated surface, e.g., azodicarbonamide to amine-reactive surfaces, aminophenylazosalicylic acid to either amine or carboxyl reactive surfaces. Then activate either photolytic compound or biopolymer by one of many conventional chemistries, e.g., amine reactive chemistries—cyanogen bromide, N-hydroxysuccinimide esters, FMP activation, EDC-mediated, divinyl sulfone; hydroxyl reactive chemistries—epoxy activation, divinyl sulfone; sulfhydryl reactive chemistries—iodoacetyl activation, maleimide, divinyl sulfone, epoxy activation; carbonyl reactive chemistries—hydrazide, reductive amination; active hydrogen reactive chemistries—diazonium, which also generate a photolytic azo bond at the same time. Finally, attach the biopolymer to photolytic compound through one or more (multiple) bonds. Wash away the excess chemicals with aqueous and organic solvents, high ionic strength and low pH solvents in multiple cycles.

II. Mass Spectrometric Analysis to Verify Structural Integrity

UV laser from 260 to 365 nm will cleave the photolytic bond. The uncoupled biopolymers are desorbed/ionized by MALDI TOF (one skilled in the art knows that SEND, SEAC and SEPAR may also be used).

III. In situ Sequencing of Biopolymer

This is accomplished by any of the well-known sequential degradation with enzymatic or chemical methods, e.g., N-terminal sequencing of proteins with aminopeptidase, C-terminal sequencing of proteins with carboxypeptidase, N-terminal sequencing of proteins with Edman degradation; sequencing of nucleic acids with exonuclease, sequencing of nucleic acids with Sanger's method; sequencing of carbohydrate with specific enzymes such as neuraminidase, mannase, fucase, galactosidase, glucosidase, O- or N-glycanase. After washing to remove excess reagent and reaction products, the analytes remaining tethered on the surface via multiple photolytic bonds consisting of a population of mass-defined biopolymers with different numbers of their end monomer missing are analyzed by MALDI TOF MS (one skilled in the art knows that SEND, SEAC and SEPAR may also be used).

Multiple internal sequencing with enzymatic or chemical methods, e.g., cleavage of proteins with endoprotease or cyanogen bromide followed by sequential degradation of N- and/or C-terminal; cleavage of nucleic acids with endonuclease followed by sequential degradation with exonuclease or chemical method; cleavage of polysaccharide chains with endoglycosidase H or endoglycosidase F followed by sequential cleavage with specific enzymes. After washing to remove excess reagent and reaction products, the analytes remaining on the surface consisting of multiple populations of mass-defined biopolymers with different numbers of their end monomer missing are analyzed by MALDI TOF MS (one skilled in the art knows).

IV. Specific Examples of Sequencing

A demonstration of this principle is provided by the actual amino acid sequence determination of a 26-residue peptide:

GHHPHGHHPHGHHPHGHHPHGHHPHGHHPHG.

This peptide $(GHHPH)_5G$ defines the metal-binding domain within the intact sequence of the 80-kDa protein known as histidine-rich glycoprotein (HRG).

Glass beads with surface arylamine groups as coupling ligands (Sigma) are washed with and suspended in cold 0.3M HCl. A 50 mg/mL aqueous solution of $NaNO_2$ is added to the beads at a ratio of 1:5 (v/v) ($NaNO_2$:HCl) and incubated at 4° C. for 15 minutes with gentle shaking. After incubation, the beads are washed with cold 0.3M HCl and 50 mm sodium phosphate buffer pH 8.0. The peptide to be sequenced is added to the beads in sodium phosphate buffer at pH 8.0 and incubated for 24 hrs. at 40° C. with gentle shaking. The beads with coupled peptides are washed with sodium phosphate buffer, sodium phosphate buffer with high concentration of salt (e.g., 1.0 M), dilute acid and organic solvent (e.g., methanol) until no peptide signal is detected in the supernate by MALDIT-OF mass spectrometry (one skilled in the art knows SEND, SEAC, and SEPAR may also be used) or by absorbance at 220 nm. An aliquot of 1 µl of the beads is then deposited on the probe tip, 1 µl of sinapinic acid (dissolved in 50% methanol/0.1% trifluoroacetic acid) is mixed with the beads and the sample was analyzed by laser desorption time-of-flight mass spectrometry. After obtaining several spectra (each an average of 50 laser shots), the remaining peptides on the surface are washed free of sinapinic acid with methanol and then digested with carboxypeptidase Y (Boehringer Mannheim) at 23° C. in a moist chamber. The digested peptides are next washed with phosphate buffered saline (PBS) pH 8.0. An aliquot of 1 µl of sinapinic acid is added to the surface and analyzed again by laser desorption time-of-flight mass spectrometry. The result of the C-terminal sequence analysis of the GHHPHG sequence is shown in FIG. 35. A nascent sequence of the peptide is observed. The sequence is deduced by the differences in the mass between two peaks.

The second example is the simultaneous sequencing of multiple peptides covalently bound by photolytic bonds to a surface. Human estrogen receptor dimerization domain (6168.4 Da) is tethered to the surface via multiple photolytic bonds. The peptide has three methionine residues in its sequence and are cleaved specifically by cyanogen bromide to generate peptides of masses 2170.58 Da (D1-M18), 3118.77 Da (A19-M45), 535.62 Da (S46-M50) and 397.62 Da (E51-L53). All these peptides are bound to the surface via the photolytic bonds. Each of these are subsequently digested in situ with carboxypeptidase Y to generate a nascent sequence that is completely resolved from the other.

Another approach to protein structure determination is simultaneous N-terminal sequencing of multiple peptides generated by tryptic digest of a protein coupled to a surface by multiple photolytic bonds. Insulin B chain is tethered to the surface via multiple photolytic bonds. The peptide has two lysine/arginine residues in its sequence that are cleaved specifically by trypsin to generate peptides of masses 2585.9 Da (F1-R22) and 859.0 Da (G23-K29), both of which are bound to the surface via the photolytic bonds. Each of these are subsequently subjected in situ to either aminopeptidase digestion or multiple cycles of Edman degradation to generate a nascent sequence that is completely resolved from the other.

Coupling and sequencing of nucleic acids is performed with similar procedure. Glass beads with surface arylamine groups as coupling ligands (Sigma) are washed with and suspended in cold 0.3M HCl. A 50 mg/mL aqueous solution of $NaNO_2$ is added to the beads at a ratio of 1:5 (v/v) ($NaNO_2$: HCl) and incubated at 4° C. for 15 minutes with gentle shaking. After incubation, the beads are washed with cold 0.3M HCl and 50 mm sodium phosphate buffer pH 8.0. The DNA (e.g., estrogen receptor responsive element, a 30-base pair oligonucleotide) to be sequenced is added to the beads in sodium phosphate buffer at pH 8.0 and incubated for 24 hrs. at 4° C. with gentle shaking. The beads with coupled DNA are washed with sodium phosphate buffer, sodium phosphate buffer with high concentration of salt (e.g., 1.0 M), dilute acid and organic solvent (e.g., methanol) until no DNA signal is detected in the supernate by MALDIT-OF mass spectrometry (one skilled in the art knows that SEND, SEAC and SEPAR may also be used) or by absorbance at 260 nm. An aliquot of 1 µl of the beads is then deposited on the probe tip, 1 µl of 3-hydroxypicolinic acid (dissolved in 50% methanol/0.1% trifluoroacetic acid) is mixed with the beads and the sample is analyzed by laser desorption time-of-flight mass spectrometry. After obtaining several mass spectra (each an average of 50 laser shots), the remaining DNA bound on the surface are washed free of 3-hydroxypicolinic acid with methanol and digested with exonuclease (Boehringer Mannheim) at 23° C. in a moist chamber. The digested DNA on the surface are next washed with phosphate buffered saline (PBS) pH 8.0 to remove excess reagent and reaction products. An aliquot of 1 µl of 3-hydroxypicolinic acid is added to the surface and analyzed again by laser desorption time-of-flight mass spectrometry. A nascent sequence of the DNA is generated. The sequence is deduced by the differences in the mass between two peaks.

Carbohydrate chains are oxidized by periodate and activated to be specifically coupled to a photolytic compound on a surface. Sequencing of the tethered carbohydrate with specific enzymes such as neuraminidase, mannase, fucase, galactosidase, glucosidase, O— or N-glycanase is carried out and determined by laser desorption time-of-flight mass spectrometry. 5-(4-aminophenylazo)salicylic acid (Aldrich) is coupled to a carboxyl reactive surface such as arylamine on controlled pore glass beads. The carbohydrate moieties of human and bovine histidine rich glycoprotein are oxidized by low concentration (0.2 M) of sodium meta-periodate in water at 23° C. for 90 min. The excess reagents are washed away with water. Add the proteins to the 5-(4-aminophenylazo) salicylic acid coupled to controlled pore glass beads in phosphate buffer, pH 8.0. Then add sodium cyanoborohydride (0.6 mg/100 µl) and stir in a fume hood at 23° C. for 18 hr. Wash extensively with water, 1 M NaCl, and then water again to remove excess reagents and unreacted proteins. An aliquot of 1 µl of the beads is then deposited on the probe tip, 1 µl of sinapinic acid (dissolved in 50% methanol/0.1% trifluoroacetic acid) is mixed with the beads and the sample is analyzed by laser desorption time-of-flight mass spectrometry. The remaining proteins bound on the surface are washed free of sinapinic acid with methanol and incubated with 2 µl of trypsin in phosphate buffer pH 8.0 at 37° C. for 30 min. The surface with bound glycopeptides is washed thoroughly with phosphate buffered saline and water to remove excess reagent and unbound peptides. An aliquot of 1 µl of sinapinic acid is mixed with the beads and the sample is analyzed by laser desorption time-of-flight mass spectrometry. After obtaining several mass spectra (each an average of 50 laser shots), the remaining glycopeptides on the probe surface are washed free of sinapinic acid with methanol and digested in sequence or in combination with N-acetylneuraminidase (NANase III, Glyko, 50 mm sodium phosphate buffer, pH 6.0, 37° C. 1 hr), mannosidase (MANase I, -Glyko, 50 mm sodium phosphate, pH 6.0, 37° C. 18 hr), fucosidase (FUCase I, Glyko, 50 mm sodium phosphate, pH 5.0, 37° C. 18 hr), N-acetylglucosaminidase (HEXase I, Glyko, 50 mm sodium phosphate, pH 5.0, 37° C. 4 hr), O-glycosidase (Glyko, 50 mm sodium phosphate, pH 5.0, 37° C. 18 hr) or N-glycanase (PNGase F, Glyko, 100 mm sodium phosphate, pH 8.6, 37° C., 18 hr). The fragmented glycopeptides on the surface are finally washed with phosphate buffered saline and water to remove the reagents and reaction products. An aliquot of 1 µl of sinapinic acid is added to the surface and analyzed again by laser desorption time-of-flight mass spectrometry. Nascent sequences of the glycopeptides are observed. The sequences are deduced by the differences in the mass between two peaks.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The oligonucleotides, compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

What is claimed:

1. A solid support, comprising:
   a plurality of single-stranded oligonucleotides immobilized thereon by a linker photocleavable under conditions of matrix-assisted laser desorption/ionization (MALDI) mass spectrometry, wherein the photocleavable linker is selected from the group consisting of 5-(4-aminophenylazo)salicylic acid and azodicarbonamide; and
   matrix for performing MALDI mass spectrometry, wherein the support comprises a flat surface.
2. The solid support of claim 1, wherein the oligonucleotides comprise an array.
3. The solid support of claim 1 that is selected from the group consisting of glass fiber filters, glass surfaces and metal surfaces.
4. The solid support of claim 1 that is selected from the group consisting of steel, gold, silver, aluminum, copper and silicon.
5. The solid support of claim 1 that is a silicon.
6. The solid support of claim 1 that is a silicon wafer.
7. The solid support of claim 1, wherein the oligonucleotides comprise oligoribonucleotides, oligodeoxyribonucleotides, nucleotide analogs, or peptide nucleic acids (PNA).
8. The solid support of claim 7, wherein the nucleotide analogs comprise a thio-modified phosphodiester or phosphotriester backbone.
9. The solid support of claim 1, wherein an oligonucleotide spacer separates each oligonucleotide strand from the support.
10. The solid support of claim 9, wherein the oligonucleotide spacer is at least about five nucleotides in length.

* * * * *